(12) United States Patent
Poltorak

(10) Patent No.: US 10,841,104 B2
(45) Date of Patent: Nov. 17, 2020

(54) SYSTEM AND METHOD FOR SECURE RELAYED COMMUNICATIONS FROM AN IMPLANTABLE MEDICAL DEVICE

(71) Applicant: Poltorak Technologies LLC, Suffern, NY (US)

(72) Inventor: Alexander I Poltorak, Monsey, NY (US)

(73) Assignee: Poltorak Technologies LLC, Suffern, NY (US)

(*) Notice: Subject to any disclaimer, the term of this patent is extended or adjusted under 35 U.S.C. 154(b) by 38 days.

(21) Appl. No.: 16/422,175

(22) Filed: May 24, 2019

(65) Prior Publication Data

US 2019/0288860 A1   Sep. 19, 2019

Related U.S. Application Data

(63) Continuation of application No. 15/948,667, filed on Apr. 9, 2018, now Pat. No. 10,305,695, which is a
(Continued)

(51) Int. Cl.
*H04L 9/32* (2006.01)
*H04L 9/00* (2006.01)
(Continued)

(52) U.S. Cl.
CPC ........ *H04L 9/3268* (2013.01); *G06F 19/3418* (2013.01); *H04L 9/006* (2013.01);
(Continued)

(58) Field of Classification Search
CPC ... H04L 9/3268; H04L 9/006; H04L 63/0428; H04L 63/04; H04L 63/0823;
(Continued)

(56) References Cited

U.S. PATENT DOCUMENTS 5,246,008 A   9/1993 Mueller
6,292,659 B1  9/2001 Olds et al.
(Continued)

OTHER PUBLICATIONS

Oyvind Borthus and Tomas Mikael Engh, "Privacy protection in a mobile Biomedical Information Collection Service", (Master's Thesis), Agder University College, Grimstad Norway (May 2005).
(Continued)

*Primary Examiner* — Darren B Schwartz
(74) *Attorney, Agent, or Firm* — Hoffberg & Associates; Steven M. Hoffberg

(57) ABSTRACT

The present invention provides systems and methods for supporting encrypted communications with a medical device, such as an implantable device, through a relay device to a remote server, and may employ cloud computing technologies. An implantable medical device is generally constrained to employ a low power transceiver, which supports short distance digital communications. A relay device, such as a smartphone or WiFi access point, acts as a conduit for the communications to the internet or other network, which need not be private or secure. The medical device supports encrypted secure communications, such as a virtual private network technology. The medical device negotiates a secure channel through a smartphone or router, for example, which provides application support for the communication, but may be isolated from the content.

20 Claims, 3 Drawing Sheets

Related U.S. Application Data continuation of application No. 14/968,336, filed on Dec. 14, 2015, now Pat. No. 9,942,051, which is a continuation of application No. 14/214,077, filed on Mar. 14, 2014, now Pat. No. 9,215,075.

(60) Provisional application No. 61/799,720, filed on Mar. 15, 2013.

(51) Int. Cl.

| | | |
|---|---|---|
| *H04W 12/00* | (2009.01) | |
| *H04L 29/06* | (2006.01) | |
| *H04W 12/02* | (2009.01) | |
| *A61B 5/00* | (2006.01) | |
| *G16H 40/67* | (2018.01) | |
| *G16H 20/30* | (2018.01) | |
| *G16H 20/17* | (2018.01) | |
| *G06F 19/00* | (2018.01) | |

(52) U.S. Cl.
CPC .......... *H04L 63/0272* (2013.01); *H04L 63/04* (2013.01); *H04L 63/0428* (2013.01); *H04L 63/0823* (2013.01); *H04W 12/0013* (2019.01); *H04W 12/02* (2013.01); *A61B 5/0006* (2013.01); *H04L 2209/80* (2013.01); *H04L 2209/88* (2013.01); *H04W 12/00403* (2019.01); *Y02D 30/70* (2020.08)

(58) Field of Classification Search
CPC ............. H04L 63/0272; H04L 2209/80; H04L 2209/88; G06F 19/3418; H04W 12/0013; H04W 12/02; H04W 12/00403; Y02D 30/70; A61B 5/0006; G16H 40/67; G16H 20/30; G16H 20/17
See application file for complete search history.

(56) References Cited

U.S. PATENT DOCUMENTS

| | | |
|---|---|---|
| 6,424,867 B1 | 7/2002 | Snell et al. |
| 6,564,102 B1 | 5/2003 | Boveja |
| 6,600,952 B1 | 7/2003 | Snell et al. |
| 6,611,715 B1 | 8/2003 | Boveja |
| 6,615,081 B1 | 9/2003 | Boveja |
| 6,643,650 B1 | 11/2003 | Slaughter et al. |
| 6,662,052 B1 | 12/2003 | Sarwal et al. |
| 6,668,191 B1 | 12/2003 | Boveja |
| 6,700,535 B2 | 3/2004 | Gilkes et al. |
| 6,721,542 B1 | 4/2004 | Anttila et al. |
| 6,744,753 B2 | 6/2004 | Heinonen et al. |
| 6,772,331 B1 | 8/2004 | Hind et al. |
| 6,789,077 B1 | 9/2004 | Slaughter et al. |
| 6,789,126 B1 | 9/2004 | Saulpaugh et al. |
| 6,792,466 B1 | 9/2004 | Saulpaugh et al. |
| 6,801,807 B2 | 10/2004 | Abrahamson |
| 6,810,363 B2 | 10/2004 | Newman et al. |
| 6,813,501 B2 | 11/2004 | Kinnunen et al. |
| 6,845,097 B2 | 1/2005 | Haller et al. |
| 6,850,252 B1 | 2/2005 | Hoffberg |
| 6,850,979 B1 | 2/2005 | Saulpaugh et al. |
| 6,862,594 B1 | 3/2005 | Saulpaugh et al. |
| 6,868,447 B1 | 3/2005 | Slaughter et al. |
| 6,879,574 B2 | 4/2005 | Naghian et al. |
| 6,885,388 B2 | 4/2005 | Gunter et al. |
| 6,886,095 B1 | 4/2005 | Hind et al. |
| 6,898,445 B2 | 5/2005 | Slettengren et al. |
| 6,898,618 B1 | 5/2005 | Slaughter et al. |
| 6,907,291 B1 | 6/2005 | Snell et al. |
| 6,908,391 B2 | 6/2005 | Gatto et al. |
| 6,912,657 B2 | 6/2005 | Gehrmann |
| 6,916,247 B2 | 7/2005 | Gatto et al. |
| 6,917,976 B1 | 7/2005 | Slaughter et al. |
| 6,918,084 B1 | 7/2005 | Slaughter et al. |
| 6,922,725 B2 | 7/2005 | Lamming et al. |
| 6,925,562 B2 | 8/2005 | Gulcu et al. |
| 6,945,870 B2 | 9/2005 | Gatto et al. |
| 6,947,995 B2 | 9/2005 | Chang et al. |
| 6,948,066 B2 | 9/2005 | Hind et al. |
| 6,950,875 B1 | 9/2005 | Slaughter et al. |
| 6,950,946 B1 | 9/2005 | Droz et al. |
| 6,961,541 B2 | 11/2005 | Overy et al. |
| 6,965,868 B1 | 11/2005 | Bednarek |
| 6,968,453 B2 | 11/2005 | Doyle et al. |
| 6,970,869 B1 | 11/2005 | Slaughter et al. |
| 6,973,493 B1 | 12/2005 | Slaughter et al. |
| 6,975,205 B1 | 12/2005 | French et al. |
| 6,980,660 B1 | 12/2005 | Hind et al. |
| 6,990,444 B2 | 1/2006 | Hind et al. |
| 7,010,573 B1 | 3/2006 | Saulpaugh et al. |
| 7,016,966 B1 | 3/2006 | Saulpaugh et al. |
| 7,028,182 B1 | 4/2006 | Killcommons |
| 7,028,184 B2 | 4/2006 | Hind et al. |
| 7,031,945 B1 | 4/2006 | Donner |
| 7,039,810 B1 | 5/2006 | Nichols |
| 7,042,988 B2 | 5/2006 | Juitt et al. |
| 7,065,574 B1 | 6/2006 | Saulpaugh et al. |
| 7,065,579 B2 | 6/2006 | Traversat et al. |
| 7,072,967 B1 | 7/2006 | Saulpaugh et al. |
| 7,080,078 B1 | 7/2006 | Slaughter et al. |
| 7,082,200 B2 | 7/2006 | Aboba et al. |
| 7,084,736 B2 | 8/2006 | Ritter |
| 7,088,233 B2 | 8/2006 | Menard |
| 7,089,089 B2 | 8/2006 | Cumming et al. |
| 7,089,298 B2 | 8/2006 | Nyman et al. |
| 7,096,137 B2 | 8/2006 | Shipton et al. |
| 7,103,313 B2 | 9/2006 | Heinonen et al. |
| 7,110,372 B2 | 9/2006 | Kovacs et al. |
| 7,116,661 B2 | 10/2006 | Patton |
| 7,120,667 B2 | 10/2006 | Derocher et al. |
| 7,121,639 B2 | 10/2006 | Plunkett |
| 7,136,927 B2 | 11/2006 | Traversat et al. |
| 7,138,902 B2 | 11/2006 | Menard |
| 7,146,307 B2 | 12/2006 | Mocek |
| 7,152,942 B2 | 12/2006 | Walmsley et al. |
| 7,155,518 B2 | 12/2006 | Forslow |
| 7,162,454 B1 | 1/2007 | Donner et al. |
| 7,165,107 B2 | 1/2007 | Pouyoul et al. |
| 7,165,824 B2 | 1/2007 | Walmsley et al. |
| 7,167,892 B2 | 1/2007 | Defosse et al. |
| 7,167,920 B2 | 1/2007 | Traversat et al. |
| 7,171,323 B2 | 1/2007 | Shipton et al. |
| 7,171,331 B2 | 1/2007 | Vock et al. |
| 7,174,277 B2 | 2/2007 | Vock et al. |
| 7,177,703 B2 | 2/2007 | Boveja et al. |
| 7,181,017 B1 | 2/2007 | Nagel et al. |
| 7,181,572 B2 | 2/2007 | Walmsley |
| 7,181,614 B1 | 2/2007 | Gehrmann et al. |
| 7,185,199 B2 | 2/2007 | Balfanz et al. |
| 7,188,251 B1 | 3/2007 | Slaughter et al. |
| 7,188,282 B2 | 3/2007 | Walmsley |
| 7,191,012 B2 | 3/2007 | Boveja et al. |
| 7,197,565 B2 | 3/2007 | Abdelaziz et al. |
| 7,200,848 B1 | 4/2007 | Slaughter et al. |
| 7,203,665 B2 | 4/2007 | Donner |
| 7,203,753 B2 | 4/2007 | Yeager et al. |
| 7,206,841 B2 | 4/2007 | Traversat et al. |
| 7,206,934 B2 | 4/2007 | Pabla et al. |
| 7,213,047 B2 | 5/2007 | Yeager et al. |
| 7,215,775 B2 | 5/2007 | Noguchi et al. |
| 7,216,109 B1 | 5/2007 | Donner |
| 7,216,231 B2 | 5/2007 | Gehrmann |
| 7,216,365 B2 | 5/2007 | Bhagwat et al. |
| 7,222,187 B2 | 5/2007 | Yeager et al. |
| 7,228,182 B2 | 6/2007 | Healy et al. |
| 7,243,356 B1 | 7/2007 | Saulpaugh et al. |
| 7,249,182 B1 | 7/2007 | Heinonen et al. |
| 7,251,331 B2 | 7/2007 | Kansala et al. |
| 7,252,230 B1 | 8/2007 | Sheikh et al. |
| 7,254,608 B2 | 8/2007 | Yeager et al. |
| 7,260,538 B2 | 8/2007 | Calderone et al. |
| 7,260,543 B1 | 8/2007 | Saulpaugh et al. |
| 7,262,709 B2 | 8/2007 | Borleske et al. |

(56) References Cited

U.S. PATENT DOCUMENTS

| | | |
|---|---|---|
| 7,263,405 B2 | 8/2007 | Boveja et al. |
| 7,263,560 B2 | 8/2007 | Abdelaziz et al. |
| 7,263,612 B2 | 8/2007 | Yamazaki et al. |
| 7,270,633 B1 | 9/2007 | Goscha et al. |
| 7,275,102 B2 | 9/2007 | Yeager et al. |
| 7,275,156 B2 | 9/2007 | Balfanz et al. |
| 7,278,034 B2 | 10/2007 | Shipton |
| 7,278,697 B2 | 10/2007 | Plunkett |
| 7,280,975 B1 | 10/2007 | Donner |
| 7,283,803 B2 | 10/2007 | Karaoguz et al. |
| 7,290,132 B2 | 10/2007 | Aboba et al. |
| 7,293,047 B2 | 11/2007 | Dunn et al. |
| 7,295,119 B2 | 11/2007 | Rappaport et al. |
| 7,297,062 B2 | 11/2007 | Gatto et al. |
| 7,299,007 B2 | 11/2007 | Eskin |
| 7,302,592 B2 | 11/2007 | Shipton et al. |
| 7,308,496 B2 | 12/2007 | Yeager et al. |
| 7,312,721 B2 | 12/2007 | Mason, Jr. et al. |
| 7,318,049 B2 | 1/2008 | Iannacci |
| 7,318,086 B2 | 1/2008 | Chang et al. |
| 7,328,243 B2 | 2/2008 | Yeager et al. |
| 7,339,914 B2 | 3/2008 | Bhagwat et al. |
| 7,340,214 B1 | 3/2008 | Hamberg |
| 7,340,438 B2 | 3/2008 | Nordman et al. |
| 7,340,500 B2 | 3/2008 | Traversat et al. |
| 7,340,770 B2 | 3/2008 | Freund |
| 7,343,350 B1 | 3/2008 | Donner |
| 7,346,167 B2 | 3/2008 | Billhartz et al. |
| 7,348,895 B2 | 3/2008 | Lagassey |
| 7,353,136 B2 | 4/2008 | Vock et al. |
| 7,353,137 B2 | 4/2008 | Vock et al. |
| 7,356,329 B2 | 4/2008 | Willey et al. |
| 7,366,901 B2 | 4/2008 | Hapamas et al. |
| 7,369,897 B2 | 5/2008 | Boveja et al. |
| 7,370,091 B1 | 5/2008 | Slaughter et al. |
| 7,377,608 B2 | 5/2008 | Walmsley et al. |
| 7,379,891 B1 | 5/2008 | Donner et al. |
| 7,379,913 B2 | 5/2008 | Steele et al. |
| 7,383,433 B2 | 6/2008 | Yeager et al. |
| 7,386,517 B1 | 6/2008 | Donner |
| 7,392,375 B2 | 6/2008 | Bartram et al. |
| 7,392,387 B2 | 6/2008 | Balfanz et al. |
| 7,395,333 B1 | 7/2008 | Saulpaugh et al. |
| 7,395,536 B2 | 7/2008 | Verbeke et al. |
| 7,398,533 B1 | 7/2008 | Slaughter et al. |
| 7,399,043 B2 | 7/2008 | Walmsley et al. |
| 7,401,152 B2 | 7/2008 | Traversat et al. |
| 7,401,153 B2 | 7/2008 | Traversat et al. |
| 7,409,434 B2 | 8/2008 | Lamming et al. |
| 7,409,569 B2 | 8/2008 | Illowsky et al. |
| 7,412,518 B1 | 8/2008 | Duigou et al. |
| 7,415,424 B1 | 8/2008 | Donner |
| 7,415,439 B2 | 8/2008 | Kontio et al. |
| 7,415,537 B1 | 8/2008 | Maes |
| 7,418,593 B2 | 8/2008 | Paatero et al. |
| 7,420,956 B2 | 9/2008 | Karaoguz et al. |
| 7,421,411 B2 | 9/2008 | Kontio et al. |
| 7,424,285 B2 | 9/2008 | Jei |
| 7,426,271 B2 | 9/2008 | Conley et al. |
| 7,426,721 B1 | 9/2008 | Saulpaugh et al. |
| 7,433,649 B2 | 10/2008 | Toulis et al. |
| 7,433,773 B2 | 10/2008 | Tengler et al. |
| 7,444,644 B1 | 10/2008 | Slaughter et al. |
| 7,454,542 B2 | 11/2008 | Illowsky et al. |
| 7,454,619 B2 | 11/2008 | Smetters et al. |
| 7,458,082 B1 | 11/2008 | Slaughter et al. |
| 7,461,172 B2 | 12/2008 | Newman et al. |
| 7,475,244 B2 | 1/2009 | Sugikawa |
| 7,477,873 B2 | 1/2009 | Tanaka et al. |
| 7,484,225 B2 | 1/2009 | Hugly et al. |
| 7,487,509 B2 | 2/2009 | Hugly et al. |
| 7,500,104 B2 | 3/2009 | Goland |
| 7,509,387 B2 | 3/2009 | Hirsch |
| 7,512,649 B2 | 3/2009 | Faybishenko et al. |
| 7,516,325 B2 | 4/2009 | Willey |
| 7,522,549 B2 | 4/2009 | Karaoguz et al. |
| 7,523,111 B2 | 4/2009 | Walmsley |
| 7,529,713 B1 | 5/2009 | Donner |
| 7,533,141 B2 | 5/2009 | Nadgir et al. |
| 7,533,161 B2 | 5/2009 | Hugly et al. |
| 7,533,172 B2 | 5/2009 | Traversat et al. |
| 7,536,177 B2 | 5/2009 | Karaoguz et al. |
| 7,536,723 B1 | 5/2009 | Bhagwat et al. |
| 7,539,532 B2 | 5/2009 | Tran |
| 7,539,533 B2 | 5/2009 | Tran |
| 7,545,941 B2 | 6/2009 | Sovio et al. |
| 7,546,254 B2 | 6/2009 | Bednarek |
| 7,548,946 B1 | 6/2009 | Saulpaugh et al. |
| 7,549,056 B2 | 6/2009 | Can |
| 7,552,031 B2 | 6/2009 | Vock et al. |
| 7,558,622 B2 | 7/2009 | Tran |
| 7,562,028 B1 | 7/2009 | Donner |
| 7,562,051 B1 | 7/2009 | Donner |
| 7,565,328 B1 | 7/2009 | Donner |
| 7,565,529 B2 | 7/2009 | Beck et al. |
| 7,570,943 B2 | 8/2009 | Sorvari et al. |
| 7,571,346 B2 | 8/2009 | Illowsky et al. |
| 7,573,855 B2 | 8/2009 | Hohl et al. |
| 7,574,523 B2 | 8/2009 | Traversat et al. |
| 7,577,575 B1 | 8/2009 | Donner et al. |
| 7,577,619 B1 | 8/2009 | Donner et al. |
| 7,577,620 B1 | 8/2009 | Donner |
| 7,577,834 B1 | 8/2009 | Traversat et al. |
| 7,581,096 B2 | 8/2009 | Balfanz et al. |
| 7,584,360 B2 | 9/2009 | Kasaura et al. |
| 7,587,196 B2 | 9/2009 | Hansen |
| 7,587,368 B2 | 9/2009 | Felsher |
| 7,590,589 B2 | 9/2009 | Hoffberg |
| 7,592,829 B2 | 9/2009 | Walmsley et al. |
| 7,596,227 B2 | 9/2009 | Illowsky et al. |
| 7,597,250 B2 | 10/2009 | Finn |
| 7,599,305 B2 | 10/2009 | Bui |
| 7,600,252 B2 | 10/2009 | Illowsky et al. |
| 7,606,242 B2 | 10/2009 | Whelan et al. |
| 7,606,570 B2 | 10/2009 | Karaoguz et al. |
| 7,607,012 B2 | 10/2009 | Nyberg |
| 7,613,881 B2 | 11/2009 | Illowsky et al. |
| 7,617,159 B1 | 11/2009 | Donner |
| 7,620,520 B2 | 11/2009 | Vock et al. |
| 7,623,295 B2 | 11/2009 | Sabeta |
| 7,624,143 B2 | 11/2009 | Newman et al. |
| 7,627,451 B2 | 12/2009 | Vock et al. |
| 7,630,941 B2 | 12/2009 | Berstis |
| 7,634,230 B2 | 12/2009 | Ji et al. |
| 7,649,872 B2 | 1/2010 | Naghian et al. |
| 7,657,255 B2 | 2/2010 | Abel et al. |
| 7,657,597 B2 | 2/2010 | Arora et al. |
| 7,660,990 B1 | 2/2010 | Thomsen et al. |
| 7,660,998 B2 | 2/2010 | Walmsley |
| 7,672,662 B2 | 3/2010 | Hamberg |
| 7,680,133 B2 | 3/2010 | Karaoguz et al. |
| 7,684,374 B2 | 3/2010 | Karaoguz et al. |
| 7,689,508 B2 | 3/2010 | Davis et al. |
| 7,697,894 B2 | 4/2010 | Zilliacus et al. |
| 7,698,393 B2 | 4/2010 | Milstein et al. |
| 7,701,912 B2 | 4/2010 | Thompson et al. |
| 7,702,821 B2 | 4/2010 | Feinberg et al. |
| 7,703,073 B2 | 4/2010 | Illowsky et al. |
| 7,707,415 B2 | 4/2010 | Braskich et al. |
| 7,707,621 B2 | 4/2010 | Walmsley |
| 7,708,194 B2 | 5/2010 | Vawter |
| 7,712,111 B2 | 5/2010 | Illowsky et al. |
| 7,712,777 B2 | 5/2010 | Breed |
| 7,715,351 B2 | 5/2010 | Karaoguz et al. |
| 7,716,492 B1 | 5/2010 | Saulpaugh et al. |
| 7,724,717 B2 | 5/2010 | Porras et al. |
| 7,729,929 B2 | 6/2010 | Heidenreich et al. |
| 7,730,482 B2 | 6/2010 | Illowsky et al. |
| 7,733,804 B2 | 6/2010 | Hardjono et al. |
| 7,743,074 B1 | 6/2010 | Parupudi et al. |
| 7,747,980 B2 | 6/2010 | Illowsky et al. |
| 7,748,618 B2 | 7/2010 | Vawter |
| 7,756,509 B2 | 7/2010 | Rajagopalan et al. |
| 7,757,076 B2 | 7/2010 | Stewart et al. |

(56) References Cited

U.S. PATENT DOCUMENTS

| | | |
|---|---|---|
| 7,760,654 B2 | 7/2010 | Adya et al. |
| 7,761,863 B2 | 7/2010 | Illowsky et al. |
| 7,761,885 B2 | 7/2010 | Labrou et al. |
| 7,761,910 B2 | 7/2010 | Ransom et al. |
| 7,762,470 B2 | 7/2010 | Finn et al. |
| 7,770,008 B2 | 8/2010 | Walmsley |
| 7,772,965 B2 | 8/2010 | Farhan et al. |
| 7,774,495 B2 | 8/2010 | Pabla et al. |
| 7,777,622 B2 | 8/2010 | Baldus et al. |
| 7,778,927 B2 | 8/2010 | Kawakami |
| 7,783,041 B2 | 8/2010 | Asokan et al. |
| 7,783,777 B1 | 8/2010 | Pabla et al. |
| 7,783,886 B2 | 8/2010 | Walmsley |
| 7,787,865 B2 | 8/2010 | Willey et al. |
| 7,788,343 B2 | 8/2010 | Haselhurst et al. |
| 7,788,369 B2 | 8/2010 | McAllen et al. |
| 7,788,663 B2 | 8/2010 | Illowsky et al. |
| 7,801,058 B2 | 9/2010 | Wang |
| 7,801,781 B2 | 9/2010 | Olin et al. |
| 7,804,807 B2 | 9/2010 | Korus et al. |
| 7,805,377 B2 | 9/2010 | Felsher |
| 7,813,822 B1 | 10/2010 | Hoffberg |
| 7,818,067 B2 | 10/2010 | Healy et al. |
| 7,818,519 B2 | 10/2010 | Plunkett |
| 7,818,811 B2 | 10/2010 | Kirovski et al. |
| 7,822,863 B2 | 10/2010 | Balfanz et al. |
| 7,823,772 B2 | 11/2010 | Vawter |
| 7,831,238 B2 | 11/2010 | Hamberg |
| 7,831,752 B2 | 11/2010 | Illowsky et al. |
| 7,831,827 B2 | 11/2010 | Walmsley |
| 7,844,834 B2 | 11/2010 | Leone et al. |
| 7,846,150 B2 | 12/2010 | Hamel et al. |
| 7,848,746 B2 | 12/2010 | Juels |
| 7,849,140 B2 | 12/2010 | Abdel-Aziz et al. |
| 7,853,255 B2 | 12/2010 | Karaoguz et al. |
| 7,853,780 B2 | 12/2010 | Rotondo et al. |
| 7,853,782 B1 * | 12/2010 | Geddes ............... H04L 63/029 713/151 |
| 7,856,339 B2 | 12/2010 | Vock et al. |
| 7,860,922 B2 | 12/2010 | Singer et al. |
| 7,860,923 B2 | 12/2010 | Singer et al. |
| 7,864,673 B2 | 1/2011 | Bonner |
| 7,869,601 B2 | 1/2011 | Ando et al. |
| 7,870,097 B2 | 1/2011 | Dunn et al. |
| 7,881,667 B2 | 2/2011 | Ji et al. |
| 7,886,335 B1 | 2/2011 | Chickering et al. |
| 7,886,962 B2 | 2/2011 | Vawter |
| 7,894,476 B2 | 2/2011 | Doerr et al. |
| 7,899,187 B2 | 3/2011 | Messerges et al. |
| 7,899,915 B2 | 3/2011 | Reisman |
| 7,904,074 B2 | 3/2011 | Karaoguz et al. |
| 7,907,935 B2 | 3/2011 | Le Saint et al. |
| 7,916,861 B2 | 3/2011 | Conley et al. |
| 7,920,518 B2 | 4/2011 | Thompson et al. |
| 7,920,534 B2 | 4/2011 | Nakayama |
| 7,920,851 B2 | 4/2011 | Moshir et al. |
| 7,937,089 B2 | 5/2011 | Smetters et al. |
| 7,944,577 B2 | 5/2011 | Chang et al. |
| 7,945,959 B2 | 5/2011 | Ilechko |
| 7,950,047 B2 | 5/2011 | Risher et al. |
| 7,953,818 B2 | 5/2011 | Chang et al. |
| 7,955,258 B2 | 6/2011 | Goscha et al. |
| 7,962,164 B2 | 6/2011 | Karaoguz et al. |
| 7,967,751 B2 | 6/2011 | Goscha et al. |
| 7,970,894 B1 | 6/2011 | Patwardhan |
| 7,974,234 B2 | 7/2011 | Gustave et al. |
| 7,974,296 B2 | 7/2011 | Karaoguz et al. |
| 7,974,714 B2 | 7/2011 | Hoffberg |
| 7,974,924 B2 | 7/2011 | Holla et al. |
| 7,975,002 B2 | 7/2011 | Newman et al. |
| 7,975,051 B2 | 7/2011 | Saint Clair et al. |
| 7,978,062 B2 | 7/2011 | LaLonde et al. |
| 7,979,692 B1 | 7/2011 | Washington et al. |
| 7,983,615 B2 | 7/2011 | Bryce et al. |
| 7,983,835 B2 | 7/2011 | Lagassey |
| 7,986,704 B2 | 7/2011 | Karaoguz et al. |
| 7,987,491 B2 | 7/2011 | Reisman |
| 7,990,947 B2 | 8/2011 | Twitchell, Jr. et al. |
| 7,991,764 B2 | 8/2011 | Rathod |
| 8,000,314 B2 | 8/2011 | Brownrigg et al. |
| 8,001,232 B1 | 8/2011 | Saulpaugh et al. |
| 8,005,476 B2 | 8/2011 | Karaoguz et al. |
| 8,009,608 B2 | 8/2011 | Karaoguz et al. |
| RE42,725 E | 9/2011 | Chang et al. |
| 8,013,732 B2 | 9/2011 | Petite et al. |
| 8,014,722 B2 | 9/2011 | Abel et al. |
| 8,019,352 B2 | 9/2011 | Rappaport et al. |
| 8,023,425 B2 | 9/2011 | Raleigh |
| 8,028,329 B2 | 9/2011 | Whitcomb |
| RE42,871 E | 10/2011 | Forslow |
| 8,031,650 B2 | 10/2011 | Petite et al. |
| 8,032,939 B2 | 10/2011 | Palnitkar et al. |
| 8,036,195 B2 | 10/2011 | Thompson et al. |
| 8,037,202 B2 | 10/2011 | Yeager et al. |
| 8,038,239 B2 | 10/2011 | Walmsley et al. |
| 8,038,593 B2 | 10/2011 | Friedman et al. |
| 8,041,032 B2 | 10/2011 | Katoozi et al. |
| 8,046,328 B2 | 10/2011 | Rhodes et al. |
| 8,046,504 B2 | 10/2011 | Feinberg et al. |
| 8,050,405 B2 | 11/2011 | Camp, Jr. et al. |
| 8,064,412 B2 | 11/2011 | Petite |
| 8,064,879 B2 | 11/2011 | Willey et al. |
| 8,064,926 B2 | 11/2011 | Howarter et al. |
| 8,068,831 B2 | 11/2011 | Karaoguz et al. |
| 8,073,839 B2 | 12/2011 | Rathod |
| 8,082,491 B1 | 12/2011 | Abdelaziz et al. |
| 8,090,399 B2 | 1/2012 | Howarter et al. |
| 8,090,592 B1 | 1/2012 | Goodall et al. |
| 8,103,333 B2 | 1/2012 | Tran |
| 8,103,691 B2 | 1/2012 | Chunilal |
| 8,103,718 B2 | 1/2012 | O'Shea et al. |
| 8,108,036 B2 | 1/2012 | Tran |
| 8,108,455 B2 | 1/2012 | Yeager et al. |
| 8,116,734 B2 | 2/2012 | Vawter |
| 8,117,547 B2 | 2/2012 | Parupudi et al. |
| 8,121,673 B2 | 2/2012 | Tran |
| 8,126,675 B2 | 2/2012 | Vock et al. |
| 8,127,039 B2 | 2/2012 | Patton et al. |
| 8,130,146 B2 | 3/2012 | Belcea et al. |
| 8,131,645 B2 | 3/2012 | Lin et al. |
| 8,135,796 B1 | 3/2012 | Slaughter et al. |
| 8,136,149 B2 | 3/2012 | Freund |
| 8,139,588 B2 | 3/2012 | Hardjono et al. |
| 8,144,725 B2 | 3/2012 | Bienas et al. |
| 8,144,948 B2 | 3/2012 | Krachman |
| 8,145,219 B2 | 3/2012 | Karaoguz et al. |
| 8,146,149 B2 | 3/2012 | Steinkogler et al. |
| 8,149,848 B2 | 4/2012 | Karaoguz et al. |
| 8,150,312 B2 | 4/2012 | Bappu et al. |
| 8,150,372 B2 | 4/2012 | Orlassino |
| 8,150,416 B2 | 4/2012 | Ribaudo et al. |
| 8,150,750 B2 | 4/2012 | Ray |
| 8,151,336 B2 | 4/2012 | Savoor |
| 8,156,337 B2 | 4/2012 | Balfanz et al. |
| 8,159,985 B2 | 4/2012 | Karaoguz et al. |
| 8,160,077 B2 | 4/2012 | Traversat et al. |
| 8,161,172 B2 | 4/2012 | Reisman |
| 8,165,142 B2 | 4/2012 | Karaoguz et al. |
| 8,166,296 B2 | 4/2012 | Buer et al. |
| 8,166,551 B2 | 4/2012 | King |
| 8,171,136 B2 | 5/2012 | Petite |
| 8,171,292 B2 | 5/2012 | Brown et al. |
| 8,175,528 B2 | 5/2012 | He et al. |
| 8,179,911 B2 | 5/2012 | Karaoguz et al. |
| 8,182,340 B2 | 5/2012 | Korp |
| 8,183,998 B2 | 5/2012 | Rao et al. |
| 8,185,119 B2 | 5/2012 | Karaoguz et al. |
| 8,193,930 B2 | 6/2012 | Petite et al. |
| 8,195,233 B2 | 6/2012 | Morikuni et al. |
| 8,195,478 B2 | 6/2012 | Petersen et al. |
| 8,195,934 B1 | 6/2012 | Lawrence |
| 8,200,195 B2 | 6/2012 | Le Saint et al. |
| 8,200,700 B2 | 6/2012 | Moore et al. |
| 8,204,522 B2 | 6/2012 | Karaoguz et al. |

(56) References Cited

U.S. PATENT DOCUMENTS

| | | |
|---|---|---|
| 8,204,588 B2 | 6/2012 | Severin et al. |
| 8,204,992 B2 | 6/2012 | Arora et al. |
| 8,212,667 B2 | 7/2012 | Petite et al. |
| 8,213,907 B2 | 7/2012 | Etchegoyen |
| 8,214,228 B2 | 7/2012 | Butler et al. |
| 8,214,645 B2 | 7/2012 | Brown et al. |
| 8,216,135 B2 | 7/2012 | Goscha et al. |
| 8,223,010 B2 | 7/2012 | Petite et al. |
| 8,224,893 B2 | 7/2012 | Newman et al. |
| 8,225,094 B2 | 7/2012 | Willey |
| 8,225,380 B2 | 7/2012 | Moshir et al. |
| 8,226,474 B2 | 7/2012 | Nguyen et al. |
| 8,228,861 B1 | 7/2012 | Nix |
| 8,229,785 B2 | 7/2012 | Fung et al. |
| 8,229,812 B2 | 7/2012 | Raleigh |
| 8,229,813 B2 | 7/2012 | Olin et al. |
| 8,229,888 B1 | 7/2012 | Roskind et al. |
| 8,233,471 B2 | 7/2012 | Brownrigg et al. |
| 8,234,128 B2 | 7/2012 | Martucci et al. |
| 8,234,387 B2 | 7/2012 | Bradley et al. |
| 8,242,907 B2 | 8/2012 | Butler et al. |
| 8,242,908 B2 | 8/2012 | Butler et al. |
| 8,242,911 B2 | 8/2012 | Moore et al. |
| 8,245,315 B2 | 8/2012 | Cassett et al. |
| 8,248,238 B2 | 8/2012 | Butler et al. |
| 8,248,239 B2 | 8/2012 | Butler et al. |
| 8,249,028 B2 | 8/2012 | Porras et al. |
| 8,249,559 B1 | 8/2012 | Meiss et al. |
| 8,250,207 B2 | 8/2012 | Raleigh |
| 8,250,628 B2 | 8/2012 | Brodfuehrer et al. |
| 8,253,567 B2 | 8/2012 | Butler et al. |
| 8,260,274 B2 | 9/2012 | Moshir et al. |
| 8,260,320 B2 | 9/2012 | Herz |
| 8,260,709 B2 | 9/2012 | Holla et al. |
| 8,261,338 B2 | 9/2012 | Brown et al. |
| 8,266,212 B2 | 9/2012 | Brunet de Courssou |
| 8,266,438 B2 | 9/2012 | Orsini et al. |
| 8,266,676 B2 | 9/2012 | Hardjono et al. |
| 8,269,630 B2 | 9/2012 | Butler et al. |
| 8,270,310 B2 | 9/2012 | Raleigh |
| 8,270,952 B2 | 9/2012 | Raleigh |
| 8,271,800 B2 | 9/2012 | Can |
| 8,271,802 B2 | 9/2012 | Orsini et al. |
| 8,275,395 B2 | 9/2012 | Howarter et al. |
| 8,275,672 B1 | 9/2012 | Nguyen et al. |
| 8,279,065 B2 | 10/2012 | Butler et al. |
| 8,279,067 B2 | 10/2012 | Berger et al. |
| 8,280,359 B2 | 10/2012 | Moshir et al. |
| 8,280,681 B2 | 10/2012 | Vock et al. |
| 8,280,682 B2 | 10/2012 | Vock et al. |
| 8,281,169 B2 | 10/2012 | Borras et al. |
| 8,284,055 B2 | 10/2012 | Butler et al. |
| 8,284,748 B2 | 10/2012 | Borghei |
| 8,289,886 B2 | 10/2012 | McDonald et al. |
| 8,290,498 B2 | 10/2012 | Karaoguz et al. |
| 8,294,579 B2 | 10/2012 | Butler et al. |
| 8,296,825 B2 | 10/2012 | Leone et al. |
| 8,301,784 B2 | 10/2012 | Hascalovici et al. |
| 8,302,167 B2 | 10/2012 | Mennes et al. |
| 8,305,935 B2 | 11/2012 | Wang |
| 8,305,936 B2 | 11/2012 | Wang |
| 8,305,980 B1 | 11/2012 | Nix |
| 8,311,214 B2 | 11/2012 | Buskey et al. |
| 8,311,939 B1 | 11/2012 | Bent et al. |
| 8,316,091 B2 | 11/2012 | Hirvela et al. |
| 8,316,237 B1 | 11/2012 | Felsher et al. |
| 8,316,438 B1 | 11/2012 | Bush et al. |
| 8,320,879 B2 | 11/2012 | Willey et al. |
| 8,321,330 B2 | 11/2012 | Kerschner et al. |
| 8,321,526 B2 | 11/2012 | Raleigh |
| 8,321,534 B1 | 11/2012 | Roskind et al. |
| 8,322,607 B2 | 12/2012 | Lapstun et al. |
| 8,323,188 B2 | 12/2012 | Tran |
| 8,323,189 B2 | 12/2012 | Tran et al. |
| 8,325,011 B2 | 12/2012 | Butler et al. |
| 8,325,031 B1 | 12/2012 | Rao et al. |
| 8,326,958 B1 | 12/2012 | Raleigh |
| 8,327,131 B1 | 12/2012 | Hardjono et al. |
| 8,328,718 B2 | 12/2012 | Tran |
| 8,331,563 B2 | 12/2012 | Healy et al. |
| 8,331,901 B2 | 12/2012 | Raleigh |
| 8,335,222 B2 | 12/2012 | Karaoguz et al. |
| 8,335,304 B2 | 12/2012 | Petite |
| 8,341,141 B2 | 12/2012 | Krislov |
| 8,341,291 B2 | 12/2012 | Twitchell, Jr. |
| 8,341,292 B2 | 12/2012 | Twitchell, Jr. |
| 8,345,881 B2 | 1/2013 | Rekimoto |
| 8,346,248 B2 | 1/2013 | Howarter et al. |
| 8,347,088 B2 | 1/2013 | Moore et al. |
| 8,347,093 B1 | 1/2013 | Ahmed |
| 8,351,898 B2 | 1/2013 | Raleigh |
| 8,352,342 B1 | 1/2013 | Bent, II et al. |
| 8,352,636 B2 | 1/2013 | Twitchell, Jr. |
| 8,353,052 B2 | 1/2013 | Larsson et al. |
| 8,355,337 B2 | 1/2013 | Raleigh |
| 8,356,180 B2 | 1/2013 | Garcia Morchon et al. |
| 8,359,016 B2 | 1/2013 | Lindeman et al. |
| 8,359,397 B2 | 1/2013 | Traversat et al. |
| 8,364,961 B2 | 1/2013 | Tanaka et al. |
| 8,368,541 B2 | 2/2013 | Moore et al. |
| 8,369,830 B2 | 2/2013 | Sperti et al. |
| 8,370,236 B1 | 2/2013 | Bent et al. |
| 8,373,556 B2 | 2/2013 | LaLonde et al. |
| 8,374,825 B2 | 2/2013 | Vock et al. |
| 8,375,202 B2 | 2/2013 | Moore et al. |
| 8,379,564 B2 | 2/2013 | Petite et al. |
| 8,380,630 B2 | 2/2013 | Felsher |
| 8,380,631 B2 | 2/2013 | Dala et al. |
| 8,380,982 B2 | 2/2013 | Miyabayashi et al. |
| 8,381,262 B2 | 2/2013 | Risher et al. |
| 8,385,240 B2 | 2/2013 | Krishnaswamy |
| 8,385,916 B2 | 2/2013 | Raleigh |
| 8,386,394 B1 | 2/2013 | Nguyen et al. |
| 8,390,456 B2 | 3/2013 | Puleston et al. |
| 8,392,289 B1 | 3/2013 | Nguyen |
| 8,395,498 B2 | 3/2013 | Gaskill et al. |
| 8,396,458 B2 | 3/2013 | Raleigh |
| 8,396,687 B2 | 3/2013 | Vock et al. |
| 8,396,801 B1 | 3/2013 | Dala et al. |
| 8,396,802 B2 | 3/2013 | Dala et al. |
| 8,396,803 B1 | 3/2013 | Dala et al. |
| 8,406,890 B2 | 3/2013 | Goetz |
| 8,421,630 B2 | 4/2013 | Butler et al. |
| 8,424,064 B2 | 4/2013 | Gardcia et al. |
| 8,425,415 B2 | 4/2013 | Tran |
| 8,428,733 B2 | 4/2013 | Carlson et al. |
| 8,428,904 B2 | 4/2013 | Vock et al. |
| 8,449,471 B2 | 5/2013 | Tran |
| 8,452,956 B1 * | 5/2013 | Kersey .............. H04L 63/10 713/153 |
| 8,454,554 B2 | 6/2013 | Reinke et al. |
| 8,456,301 B2 | 6/2013 | Fennell et al. |
| 8,461,985 B2 | 6/2013 | Fennell et al. |
| 8,472,630 B2 | 6/2013 | Konrad et al. |
| 8,475,368 B2 | 7/2013 | Tran et al. |
| 8,498,941 B2 | 7/2013 | Felsher |
| 8,500,636 B2 | 8/2013 | Tran |
| 8,508,336 B2 | 8/2013 | Giobbi et al. |
| 8,515,547 B2 | 8/2013 | Mass et al. |
| 8,522,019 B2 | 8/2013 | Michaelis |
| 8,532,757 B2 | 9/2013 | Molnar et al. |
| 8,533,475 B2 | 9/2013 | Frikart et al. |
| 8,538,513 B2 | 9/2013 | Molnar et al. |
| 8,549,600 B2 | 10/2013 | Shedrinsky |
| 8,555,063 B2 | 10/2013 | Xiao et al. |
| 8,558,699 B2 | 10/2013 | Butler et al. |
| 8,565,886 B2 | 10/2013 | Nelson et al. |
| 8,587,427 B2 | 11/2013 | LaLonde et al. |
| 8,593,287 B2 | 11/2013 | Hayter et al. |
| 8,600,895 B2 | 12/2013 | Felsher |
| 8,630,416 B2 | 1/2014 | Qi et al. |
| 8,645,531 B2 | 2/2014 | Adams et al. |
| 8,652,038 B2 | 2/2014 | Tran et al. |
| 8,653,966 B2 | 2/2014 | Rao et al. |

(56) References Cited

U.S. PATENT DOCUMENTS

| | | |
|---|---|---|
| 8,654,974 B2 | 2/2014 | Anderson et al. |
| 8,660,814 B2 | 2/2014 | Vock et al. |
| 8,667,156 B2 | 3/2014 | Soliman et al. |
| 8,667,293 B2 | 3/2014 | Birtwhistle et al. |
| 8,670,830 B2 | 3/2014 | Carlson et al. |
| 8,679,014 B2 | 3/2014 | Bennett et al. |
| 8,682,437 B2 | 3/2014 | Kalpin et al. |
| 8,684,900 B2 | 4/2014 | Tran |
| 8,684,922 B2 | 4/2014 | Tran |
| 8,688,147 B2 | 4/2014 | Nguyen et al. |
| 8,688,406 B2 | 4/2014 | Vock et al. |
| 8,688,981 B2 | 4/2014 | Gim et al. |
| 8,701,167 B2 | 4/2014 | Kovalan |
| 8,706,181 B2 | 4/2014 | Stypulkowski et al. |
| 8,707,040 B2 | 4/2014 | Andersen |
| 8,707,392 B2 | 4/2014 | Birtwhistle et al. |
| 8,708,903 B2 | 4/2014 | Tran |
| 8,727,978 B2 | 5/2014 | Tran et al. |
| 8,736,441 B2 | 5/2014 | Rao et al. |
| 8,747,313 B2 | 6/2014 | Tran et al. |
| 8,761,890 B2 | 6/2014 | Gupta et al. |
| 8,764,651 B2 | 7/2014 | Tran |
| 8,768,323 B2 | 7/2014 | Liu et al. |
| 8,775,196 B2 | 7/2014 | Simpson et al. |
| 8,776,246 B2 | 7/2014 | Allegri et al. |
| 8,793,142 B2 | 7/2014 | Fishman et al. |
| 8,798,764 B2 | 8/2014 | Molnar et al. |
| 8,799,022 B1 | 8/2014 | O'Brien et al. |
| 8,812,098 B2 | 8/2014 | Giftakis et al. |
| 8,818,522 B2 | 8/2014 | Mass et al. |
| 8,849,718 B2 | 9/2014 | Dala et al. |
| 8,868,201 B2 | 10/2014 | Roberts et al. |
| 8,886,125 B2 | 11/2014 | Agrawal et al. |
| 8,886,332 B2 | 11/2014 | Molnar et al. |
| 8,892,886 B2 | 11/2014 | Konrad et al. |
| 8,904,181 B1 | 12/2014 | Felsher et al. |
| 8,907,909 B2 | 12/2014 | Bello et al. |
| 8,912,687 B2 | 12/2014 | Kesler et al. |
| 8,914,115 B2 | 12/2014 | Giftakis et al. |
| 8,918,854 B1 | 12/2014 | Giobbi |
| 8,929,986 B2 | 1/2015 | Parker et al. |
| 8,934,986 B2 | 1/2015 | Goetz |
| 8,937,930 B2 | 1/2015 | Sprigg et al. |
| 8,941,470 B2 | 1/2015 | Butler et al. |
| 8,947,233 B2 | 2/2015 | Butler et al. |
| 8,959,348 B2 | 2/2015 | Tsouri |
| 8,968,195 B2 | 3/2015 | Tran |
| 8,970,392 B2 | 3/2015 | LaLonde et al. |
| 8,971,958 B2 | 3/2015 | Frikart et al. |
| 8,976,021 B2 | 3/2015 | Ozgul et al. |
| 8,978,026 B2 | 3/2015 | Charlton et al. |
| 8,988,223 B2 | 3/2015 | Puleston et al. |
| 9,000,929 B2 | 4/2015 | Hayter et al. |
| 9,026,792 B2 | 5/2015 | Andersen |
| 9,035,767 B2 | 5/2015 | Fennell et al. |
| 9,042,613 B2 | 5/2015 | Spilker et al. |
| 9,042,989 B2 | 5/2015 | Carlson et al. |
| 9,042,990 B2 | 5/2015 | Carlson et al. |
| 9,053,317 B2 | 6/2015 | Shieh et al. |
| 9,055,924 B2 | 6/2015 | Roth |
| 9,055,974 B2 | 6/2015 | Goetz |
| 9,060,683 B2 | 6/2015 | Tran |
| 9,072,870 B2 | 7/2015 | Wu et al. |
| 9,079,039 B2 | 7/2015 | Carlson et al. |
| 9,094,383 B2 | 7/2015 | Garcia Morchon et al. |
| 9,101,306 B2 | 8/2015 | Bernini et al. |
| 9,106,203 B2 | 8/2015 | Kesler et al. |
| 9,106,609 B2 | 8/2015 | Kovalan |
| 9,107,586 B2 | 8/2015 | Tran |
| 9,112,918 B2 | 8/2015 | Schultz et al. |
| 9,117,128 B2 | 8/2015 | Mats et al. |
| 9,124,640 B2 | 9/2015 | Sweet et al. |
| 9,125,627 B2 | 9/2015 | Stein |
| 9,149,635 B2 | 10/2015 | Denison et al. |
| 9,168,006 B2 | 10/2015 | Georgiev et al. |
| 9,172,679 B1* | 10/2015 | Geddes ............... H04L 63/0884 |
| 9,177,456 B2 | 11/2015 | Fennell et al. |
| 9,185,087 B2 | 11/2015 | Carlson et al. |
| 9,189,600 B2 | 11/2015 | Spilker et al. |
| 9,211,411 B2 | 12/2015 | Wu et al. |
| 9,215,075 B1 | 12/2015 | Poltorak |
| 9,215,581 B2 | 12/2015 | Julian et al. |
| 9,215,980 B2 | 12/2015 | Tran et al. |
| 9,237,012 B2 | 1/2016 | Andersen |
| 9,565,180 B2* | 2/2017 | Yerra .................... H04L 9/3271 |
| 9,942,051 B1 | 4/2018 | Poltorak |
| 10,255,445 B1* | 4/2019 | Brinskelle ........... H04L 63/0428 |
| 2001/0050990 A1 | 12/2001 | Sudia |
| 2001/0051787 A1 | 12/2001 | Haller et al. |
| 2002/0069278 A1 | 6/2002 | Forslow |
| 2002/0072975 A1 | 6/2002 | Steele et al. |
| 2002/0075844 A1 | 6/2002 | Hagen |
| 2002/0116637 A1 | 8/2002 | Deitsch et al. |
| 2002/0133534 A1 | 9/2002 | Forslow |
| 2002/0143655 A1 | 10/2002 | Elston et al. |
| 2002/0143855 A1 | 10/2002 | Traversat et al. |
| 2002/0143944 A1 | 10/2002 | Traversat et al. |
| 2002/0147771 A1 | 10/2002 | Traversat et al. |
| 2002/0147810 A1 | 10/2002 | Traversat et al. |
| 2002/0152299 A1 | 10/2002 | Traversat et al. |
| 2002/0161476 A1 | 10/2002 | Panofsky et al. |
| 2002/0178361 A1* | 11/2002 | Genty ................ H04L 63/0272 |
| | | 713/175 |
| 2002/0184310 A1 | 12/2002 | Traversat et al. |
| 2002/0184311 A1 | 12/2002 | Traversat et al. |
| 2002/0184357 A1 | 12/2002 | Traversat et al. |
| 2002/0184358 A1 | 12/2002 | Traversat et al. |
| 2002/0188657 A1 | 12/2002 | Traversat et al. |
| 2003/0002521 A1 | 1/2003 | Traversat et al. |
| 2003/0041141 A1 | 2/2003 | Abdelaziz et al. |
| 2003/0065525 A1 | 4/2003 | Giacchetti et al. |
| 2003/0081783 A1* | 5/2003 | Adusumilli ......... H04W 12/001 |
| | | 380/270 |
| 2003/0087629 A1 | 5/2003 | Juitt et al. |
| 2003/0093691 A1 | 5/2003 | Simon et al. |
| 2003/0100369 A1 | 5/2003 | Gatto et al. |
| 2003/0100370 A1 | 5/2003 | Gatto et al. |
| 2003/0100371 A1 | 5/2003 | Gatto et al. |
| 2003/0100372 A1 | 5/2003 | Gatto et al. |
| 2003/0130708 A1 | 7/2003 | Von Arx et al. |
| 2003/0229900 A1 | 12/2003 | Reisman |
| 2003/0237004 A1* | 12/2003 | Okamura ............ H04L 63/0272 |
| | | 726/15 |
| 2004/0019807 A1 | 1/2004 | Freund |
| 2004/0030743 A1 | 2/2004 | Hugly et al. |
| 2004/0030794 A1 | 2/2004 | Hugly et al. |
| 2004/0031038 A1 | 2/2004 | Hugly et al. |
| 2004/0031058 A1 | 2/2004 | Reisman |
| 2004/0044727 A1 | 3/2004 | Abdelaziz et al. |
| 2004/0064512 A1 | 4/2004 | Arora et al. |
| 2004/0064568 A1 | 4/2004 | Arora et al. |
| 2004/0064693 A1 | 4/2004 | Pabla et al. |
| 2004/0073795 A1 | 4/2004 | Jablon |
| 2004/0078573 A1 | 4/2004 | Matsuyama |
| 2004/0088347 A1 | 5/2004 | Yeager et al. |
| 2004/0088348 A1 | 5/2004 | Yeager et al. |
| 2004/0088369 A1 | 5/2004 | Yeager et al. |
| 2004/0088646 A1 | 5/2004 | Yeager et al. |
| 2004/0098447 A1 | 5/2004 | Verbeke et al. |
| 2004/0133640 A1 | 7/2004 | Yeager et al. |
| 2004/0148326 A1 | 7/2004 | Nadgir et al. |
| 2004/0162871 A1 | 8/2004 | Pabla et al. |
| 2004/0167465 A1 | 8/2004 | Mihai et al. |
| 2004/0171369 A1 | 9/2004 | Little et al. |
| 2004/0198220 A1 | 10/2004 | Whelan et al. |
| 2004/0266449 A1 | 12/2004 | Smetters et al. |
| 2005/0010786 A1* | 1/2005 | Michener ................ G06F 21/34 |
| | | 713/185 |
| 2005/0021969 A1* | 1/2005 | Williams ............... H04L 9/3268 |
| | | 713/176 |
| 2005/0086300 A1 | 4/2005 | Yeager et al. |
| 2005/0109841 A1 | 5/2005 | Ryan et al. |
| 2005/0120232 A1* | 6/2005 | Hori ........................ G06Q 30/06 |
| | | 713/193 |

(56) References Cited

U.S. PATENT DOCUMENTS

| | | |
|---|---|---|
| 2005/0129240 A1 | 6/2005 | Balfanz et al. |
| 2005/0138351 A1* | 6/2005 | Lee .................. H04L 63/162 |
| | | 713/151 |
| 2005/0141706 A1 | 6/2005 | Regli et al. |
| 2005/0144437 A1 | 6/2005 | Ransom et al. |
| 2005/0204134 A1 | 9/2005 | Von Arx et al. |
| 2005/0228998 A1* | 10/2005 | Chan .................. H04L 9/3268 |
| | | 713/175 |
| 2005/0233811 A1 | 10/2005 | Gatto et al. |
| 2005/0259611 A1 | 11/2005 | Bhagwat et al. |
| 2005/0261970 A1 | 11/2005 | Vucina et al. |
| 2005/0273850 A1 | 12/2005 | Freund |
| 2005/0278534 A1* | 12/2005 | Nadalin ............... H04L 9/3263 |
| | | 713/175 |
| 2005/0288736 A1 | 12/2005 | Persen et al. |
| 2006/0002331 A1 | 1/2006 | Bhagwat et al. |
| 2006/0010251 A1 | 1/2006 | Mrsic-Flogel et al. |
| 2006/0010485 A1 | 1/2006 | Gorman |
| 2006/0040248 A1 | 2/2006 | Aaron |
| 2006/0041445 A1 | 2/2006 | Aaron |
| 2006/0041446 A1 | 2/2006 | Aaron |
| 2006/0041460 A1 | 2/2006 | Aaron |
| 2006/0041891 A1 | 2/2006 | Aaron |
| 2006/0062206 A1 | 3/2006 | Krishnaswamy |
| 2006/0080534 A1* | 4/2006 | Yeap .................. H04W 12/0804 |
| | | 713/176 |
| 2006/0092043 A1 | 5/2006 | Lagassey |
| 2006/0095199 A1 | 5/2006 | Lagassey |
| 2006/0156054 A1 | 7/2006 | Brown et al. |
| 2006/0167784 A1 | 7/2006 | Hoffberg |
| 2006/0174017 A1 | 8/2006 | Robertson |
| 2006/0208066 A1 | 9/2006 | Finn et al. |
| 2006/0219776 A1 | 10/2006 | Finn |
| 2006/0234678 A1 | 10/2006 | Juitt et al. |
| 2006/0282662 A1 | 12/2006 | Whitcomb |
| 2006/0291455 A1 | 12/2006 | Katz et al. |
| 2007/0004436 A1 | 1/2007 | Stirbu |
| 2007/0022474 A1 | 1/2007 | Rowett et al. |
| 2007/0022479 A1 | 1/2007 | Sikdar et al. |
| 2007/0025245 A1 | 2/2007 | Porras et al. |
| 2007/0025265 A1 | 2/2007 | Porras et al. |
| 2007/0060099 A1 | 3/2007 | Ramer et al. |
| 2007/0060109 A1 | 3/2007 | Ramer et al. |
| 2007/0060114 A1 | 3/2007 | Ramer et al. |
| 2007/0060129 A1 | 3/2007 | Ramer et al. |
| 2007/0060136 A1 | 3/2007 | Ramer et al. |
| 2007/0060173 A1 | 3/2007 | Ramer et al. |
| 2007/0061197 A1 | 3/2007 | Ramer et al. |
| 2007/0061198 A1 | 3/2007 | Ramer et al. |
| 2007/0061211 A1 | 3/2007 | Ramer et al. |
| 2007/0061229 A1 | 3/2007 | Ramer et al. |
| 2007/0061242 A1 | 3/2007 | Ramer et al. |
| 2007/0061243 A1 | 3/2007 | Ramer et al. |
| 2007/0061244 A1 | 3/2007 | Ramer et al. |
| 2007/0061245 A1 | 3/2007 | Ramer et al. |
| 2007/0061246 A1 | 3/2007 | Ramer et al. |
| 2007/0061247 A1 | 3/2007 | Ramer et al. |
| 2007/0061300 A1 | 3/2007 | Ramer et al. |
| 2007/0061301 A1 | 3/2007 | Ramer et al. |
| 2007/0061302 A1 | 3/2007 | Ramer et al. |
| 2007/0061303 A1 | 3/2007 | Ramer et al. |
| 2007/0061317 A1 | 3/2007 | Ramer et al. |
| 2007/0061328 A1 | 3/2007 | Ramer et al. |
| 2007/0061331 A1 | 3/2007 | Ramer et al. |
| 2007/0061332 A1 | 3/2007 | Ramer et al. |
| 2007/0061333 A1 | 3/2007 | Ramer et al. |
| 2007/0061334 A1 | 3/2007 | Ramer et al. |
| 2007/0061335 A1 | 3/2007 | Ramer et al. |
| 2007/0061336 A1 | 3/2007 | Ramer et al. |
| 2007/0061363 A1 | 3/2007 | Ramer et al. |
| 2007/0073717 A1 | 3/2007 | Ramer et al. |
| 2007/0073718 A1 | 3/2007 | Ramer et al. |
| 2007/0073719 A1 | 3/2007 | Ramer et al. |
| 2007/0073722 A1 | 3/2007 | Ramer et al. |
| 2007/0073723 A1 | 3/2007 | Ramer et al. |
| 2007/0087756 A1 | 4/2007 | Hoffberg |
| 2007/0094042 A1 | 4/2007 | Ramer et al. |
| 2007/0097885 A1 | 5/2007 | Traversat et al. |
| 2007/0100650 A1 | 5/2007 | Ramer et al. |
| 2007/0100651 A1 | 5/2007 | Ramer et al. |
| 2007/0100652 A1 | 5/2007 | Ramer et al. |
| 2007/0100653 A1 | 5/2007 | Ramer et al. |
| 2007/0100805 A1 | 5/2007 | Ramer et al. |
| 2007/0100806 A1 | 5/2007 | Ramer et al. |
| 2007/0118533 A1 | 5/2007 | Ramer et al. |
| 2007/0136817 A1* | 6/2007 | Nguyen ................. G07F 17/32 |
| | | 726/26 |
| 2007/0143629 A1 | 6/2007 | Hardjono et al. |
| 2007/0143827 A1 | 6/2007 | Nicodemus et al. |
| 2007/0143851 A1 | 6/2007 | Nicodemus et al. |
| 2007/0156895 A1 | 7/2007 | Vuong |
| 2007/0168354 A1 | 7/2007 | Ramer et al. |
| 2007/0169184 A1 | 7/2007 | Krywaniuk |
| 2007/0171885 A1 | 7/2007 | Bhagwat et al. |
| 2007/0192294 A1 | 8/2007 | Ramer et al. |
| 2007/0192318 A1 | 8/2007 | Ramer et al. |
| 2007/0198432 A1 | 8/2007 | Pitroda et al. |
| 2007/0198485 A1 | 8/2007 | Ramer et al. |
| 2007/0220259 A1 | 9/2007 | Pavlicic |
| 2007/0239724 A1 | 10/2007 | Ramer et al. |
| 2007/0260635 A1 | 11/2007 | Ramer et al. |
| 2007/0263783 A1 | 11/2007 | Speranza |
| 2007/0288427 A1 | 12/2007 | Ramer et al. |
| 2007/0293323 A1 | 12/2007 | Gatto et al. |
| 2008/0009268 A1 | 1/2008 | Ramer et al. |
| 2008/0032801 A1 | 2/2008 | Brunet de Courssou |
| 2008/0033869 A1 | 2/2008 | Steele et al. |
| 2008/0041937 A1 | 2/2008 | Vawter |
| 2008/0044014 A1 | 2/2008 | Corndorf |
| 2008/0052769 A1 | 2/2008 | Leone et al. |
| 2008/0063201 A1 | 3/2008 | Wormald et al. |
| 2008/0076572 A1 | 3/2008 | Nguyen et al. |
| 2008/0092181 A1 | 4/2008 | Britt |
| 2008/0095180 A1 | 4/2008 | Vucina et al. |
| 2008/0097858 A1 | 4/2008 | Vucina et al. |
| 2008/0098212 A1 | 4/2008 | Helms et al. |
| 2008/0109879 A1 | 5/2008 | Bhagwat et al. |
| 2008/0126794 A1 | 5/2008 | Wang et al. |
| 2008/0141360 A1 | 6/2008 | Hicks et al. |
| 2008/0167954 A1 | 7/2008 | Kawakami |
| 2008/0183853 A1 | 7/2008 | Manion et al. |
| 2008/0222711 A1 | 9/2008 | Michaelis |
| 2008/0222715 A1 | 9/2008 | Bansal et al. |
| 2008/0229402 A1 | 9/2008 | Smetters et al. |
| 2008/0234047 A1 | 9/2008 | Nguyen |
| 2008/0242279 A1 | 10/2008 | Ramer et al. |
| 2008/0244717 A1 | 10/2008 | Jelatis et al. |
| 2008/0252485 A1 | 10/2008 | Lagassey |
| 2008/0256618 A1 | 10/2008 | Bansal et al. |
| 2009/0013380 A1 | 1/2009 | Chandrasiri et al. |
| 2009/0016529 A1 | 1/2009 | Gopinath et al. |
| 2009/0036111 A1 | 2/2009 | Danford et al. |
| 2009/0046591 A1 | 2/2009 | Krishnaswamy et al. |
| 2009/0046598 A1 | 2/2009 | Krishnaswamy et al. |
| 2009/0046644 A1 | 2/2009 | Krishnaswamy et al. |
| 2009/0046676 A1 | 2/2009 | Krishnaswamy et al. |
| 2009/0046861 A1 | 2/2009 | Krishnaswamy |
| 2009/0047930 A1 | 2/2009 | Krishnaswamy et al. |
| 2009/0047966 A1 | 2/2009 | Krishnaswamy et al. |
| 2009/0049158 A1 | 2/2009 | Krishnaswamy et al. |
| 2009/0058635 A1 | 3/2009 | LaLonde et al. |
| 2009/0060201 A1 | 3/2009 | Rhodes et al. |
| 2009/0073943 A1 | 3/2009 | Krishnaswamy et al. |
| 2009/0088133 A1 | 4/2009 | Orlassino |
| 2009/0119741 A1 | 5/2009 | Palnitkar et al. |
| 2009/0119776 A1 | 5/2009 | Palnitkar et al. |
| 2009/0144541 A1 | 6/2009 | Kim et al. |
| 2009/0168990 A1 | 7/2009 | Makagon et al. |
| 2009/0199009 A1 | 8/2009 | Chia et al. |
| 2009/0204805 A1 | 8/2009 | Robba et al. |
| 2009/0204964 A1 | 8/2009 | Foley et al. |
| 2009/0227876 A1 | 9/2009 | Tran |
| 2009/0227877 A1 | 9/2009 | Tran |
| 2009/0254572 A1 | 10/2009 | Redlich et al. |

(56) References Cited

U.S. PATENT DOCUMENTS

| | | |
|---|---|---|
| 2009/0254646 A1 | 10/2009 | Brown et al. |
| 2009/0260070 A1 | 10/2009 | Soliman |
| 2009/0270949 A1 | 10/2009 | Kalpin et al. |
| 2009/0271221 A1 | 10/2009 | Aridi et al. |
| 2009/0275403 A1 | 11/2009 | Proctor |
| 2009/0281872 A1 | 11/2009 | Kalaboukis |
| 2009/0287837 A1 | 11/2009 | Felsher |
| 2009/0289776 A1 | 11/2009 | Moore et al. |
| 2009/0299812 A1 | 12/2009 | Ray |
| 2009/0318779 A1 | 12/2009 | Tran |
| 2009/0319672 A1 | 12/2009 | Reisman |
| 2009/0320073 A1 | 12/2009 | Reisman |
| 2009/0322510 A1 | 12/2009 | Berger et al. |
| 2009/0327729 A1 | 12/2009 | Rhodes et al. |
| 2010/0031318 A1 | 2/2010 | Gardcia et al. |
| 2010/0037293 A1 * | 2/2010 | StJohns ................. H04L 63/20 726/2 |
| 2010/0057801 A1 | 3/2010 | Ramer et al. |
| 2010/0058480 A1 | 3/2010 | Hedberg et al. |
| 2010/0065625 A1 | 3/2010 | Sabeta |
| 2010/0070417 A1 | 3/2010 | Flynn et al. |
| 2010/0076845 A1 | 3/2010 | Ramer et al. |
| 2010/0082430 A1 | 4/2010 | Ramer et al. |
| 2010/0082431 A1 | 4/2010 | Ramer et al. |
| 2010/0085160 A1 | 4/2010 | Fu |
| 2010/0094981 A1 | 4/2010 | Cordray et al. |
| 2010/0095077 A1 | 4/2010 | Lockwood |
| 2010/0099396 A1 | 4/2010 | Huq et al. |
| 2010/0100930 A1 | 4/2010 | King |
| 2010/0115279 A1 | 5/2010 | Frikart et al. |
| 2010/0115606 A1 | 5/2010 | Samovskiy et al. |
| 2010/0121705 A1 | 5/2010 | Ramer et al. |
| 2010/0122083 A1 | 5/2010 | Gim et al. |
| 2010/0122087 A1 | 5/2010 | Gim et al. |
| 2010/0131618 A1 | 5/2010 | Brewis et al. |
| 2010/0131619 A1 | 5/2010 | Brewis et al. |
| 2010/0131622 A1 | 5/2010 | Brewis et al. |
| 2010/0131652 A1 | 5/2010 | Brewis et al. |
| 2010/0132040 A1 | 5/2010 | Bhagwat et al. |
| 2010/0134257 A1 | 6/2010 | Puleston et al. |
| 2010/0138293 A1 | 6/2010 | Ramer et al. |
| 2010/0138296 A1 | 6/2010 | Ramer et al. |
| 2010/0138908 A1 | 6/2010 | Vennelakanti et al. |
| 2010/0138926 A1 | 6/2010 | Kashchenko et al. |
| 2010/0142410 A1 | 6/2010 | Huynh Van et al. |
| 2010/0145804 A1 | 6/2010 | Ramer et al. |
| 2010/0146146 A1 | 6/2010 | Welts et al. |
| 2010/0150170 A1 | 6/2010 | Lee et al. |
| 2010/0153208 A1 | 6/2010 | Ramer et al. |
| 2010/0153211 A1 | 6/2010 | Ramer et al. |
| 2010/0169179 A1 | 7/2010 | Ramer et al. |
| 2010/0186078 A1 | 7/2010 | Napoli et al. |
| 2010/0188975 A1 | 7/2010 | Raleigh |
| 2010/0188990 A1 | 7/2010 | Raleigh |
| 2010/0188991 A1 | 7/2010 | Raleigh |
| 2010/0188992 A1 | 7/2010 | Raleigh |
| 2010/0188993 A1 | 7/2010 | Raleigh |
| 2010/0188994 A1 | 7/2010 | Raleigh |
| 2010/0188995 A1 | 7/2010 | Raleigh |
| 2010/0190470 A1 | 7/2010 | Raleigh |
| 2010/0191575 A1 | 7/2010 | Raleigh |
| 2010/0191576 A1 | 7/2010 | Raleigh |
| 2010/0191604 A1 | 7/2010 | Raleigh |
| 2010/0191612 A1 | 7/2010 | Raleigh |
| 2010/0191613 A1 | 7/2010 | Raleigh |
| 2010/0191846 A1 | 7/2010 | Raleigh |
| 2010/0191847 A1 | 7/2010 | Raleigh |
| 2010/0192120 A1 | 7/2010 | Raleigh |
| 2010/0192170 A1 | 7/2010 | Raleigh |
| 2010/0192207 A1 | 7/2010 | Raleigh |
| 2010/0192212 A1 | 7/2010 | Raleigh |
| 2010/0192220 A1 | 7/2010 | Heizmann et al. |
| 2010/0197266 A1 | 8/2010 | Raleigh |
| 2010/0197268 A1 | 8/2010 | Raleigh |
| 2010/0198681 A1 | 8/2010 | Ramer et al. |
| 2010/0211458 A1 | 8/2010 | Ramer et al. |
| 2010/0211645 A1 | 8/2010 | Wang et al. |
| 2010/0217662 A1 | 8/2010 | Ramer et al. |
| 2010/0217663 A1 | 8/2010 | Ramer et al. |
| 2010/0235285 A1 | 9/2010 | Hoffberg |
| 2010/0235879 A1 | 9/2010 | Burnside et al. |
| 2010/0241595 A1 | 9/2010 | Felsher |
| 2010/0241862 A1 | 9/2010 | Garcia Morchon et al. |
| 2010/0250497 A1 | 9/2010 | Redlich et al. |
| 2010/0259719 A1 | 10/2010 | Sabeta |
| 2010/0268190 A1 | 10/2010 | Mielenz |
| 2010/0269146 A1 | 10/2010 | Britt |
| 2010/0275250 A1 | 10/2010 | Devadoss et al. |
| 2010/0280418 A1 | 11/2010 | Klose |
| 2010/0281364 A1 | 11/2010 | Sidman |
| 2010/0292556 A1 | 11/2010 | Golden |
| 2010/0293051 A1 | 11/2010 | Ramer et al. |
| 2010/0293221 A1 | 11/2010 | Sidman et al. |
| 2010/0299517 A1 | 11/2010 | Jukic et al. |
| 2010/0299522 A1 | 11/2010 | Khambete |
| 2010/0299763 A1 | 11/2010 | Marcus et al. |
| 2010/0304737 A1 | 12/2010 | Jain et al. |
| 2010/0313025 A1 | 12/2010 | Tsouri |
| 2010/0317420 A1 | 12/2010 | Hoffberg |
| 2010/0322213 A1 | 12/2010 | Liu et al. |
| 2010/0328077 A1 | 12/2010 | Stein |
| 2010/0328320 A1 | 12/2010 | Kerstna et al. |
| 2010/0331682 A1 | 12/2010 | Stein et al. |
| 2010/0331735 A1 | 12/2010 | Stein |
| 2011/0004513 A1 | 1/2011 | Hoffberg |
| 2011/0015993 A1 | 1/2011 | Ramer et al. |
| 2011/0015994 A1 | 1/2011 | Ramer et al. |
| 2011/0019627 A1 | 1/2011 | Krishnaswamy et al. |
| 2011/0029378 A1 | 2/2011 | Ramer et al. |
| 2011/0029387 A1 | 2/2011 | Ramer et al. |
| 2011/0040578 A1 | 2/2011 | Ramsey |
| 2011/0047062 A1 | 2/2011 | Kerschner et al. |
| 2011/0082520 A1 | 4/2011 | McElveen, Jr. |
| 2011/0106614 A1 | 5/2011 | Ramer et al. |
| 2011/0145076 A1 | 6/2011 | Ramer et al. |
| 2011/0145373 A1 | 6/2011 | Awad et al. |
| 2011/0145894 A1 | 6/2011 | Garcia Morchon et al. |
| 2011/0154018 A1 | 6/2011 | Edstrom et al. |
| 2011/0159902 A1 | 6/2011 | Ramer et al. |
| 2011/0167474 A1 | 7/2011 | Sinha et al. |
| 2011/0170692 A1 | 7/2011 | Konrad et al. |
| 2011/0190580 A1 | 8/2011 | Bennett et al. |
| 2011/0190581 A1 | 8/2011 | Bennett et al. |
| 2011/0190595 A1 | 8/2011 | Bennett et al. |
| 2011/0194698 A1 | 8/2011 | Asano et al. |
| 2011/0200194 A1 | 8/2011 | Goscha et al. |
| 2011/0202874 A1 | 8/2011 | Ramer et al. |
| 2011/0216674 A1 | 9/2011 | McDonald et al. |
| 2011/0217966 A1 | 9/2011 | McDonald et al. |
| 2011/0219234 A1 | 9/2011 | Bogner |
| 2011/0219419 A1 | 9/2011 | Reisman |
| 2011/0221568 A1 | 9/2011 | Giobbi |
| 2011/0230268 A1 | 9/2011 | Williams |
| 2011/0231936 A1 | 9/2011 | Williams et al. |
| 2011/0246766 A1 | 10/2011 | Orsini et al. |
| 2011/0251848 A1 | 10/2011 | Alameddine et al. |
| 2011/0251960 A1 | 10/2011 | Holla et al. |
| 2011/0258046 A1 | 10/2011 | Ramer et al. |
| 2011/0273287 A1 | 11/2011 | LaLonde et al. |
| 2011/0273568 A1 | 11/2011 | Lagassey |
| 2011/0275393 A1 | 11/2011 | Ramer et al. |
| 2011/0276673 A1 | 11/2011 | Piazza et al. |
| 2011/0277028 A1 | 11/2011 | Piazza et al. |
| 2011/0289308 A1 | 11/2011 | Sobko et al. |
| 2011/0289314 A1 | 11/2011 | Whitcomb |
| 2011/0302408 A1 | 12/2011 | McDermott et al. |
| 2011/0307710 A1 | 12/2011 | McGuire et al. |
| 2011/0312310 A1 | 12/2011 | Ramer et al. |
| 2011/0313862 A1 | 12/2011 | Ramer et al. |
| 2011/0320264 A1 | 12/2011 | Ramer et al. |
| 2011/0320265 A1 | 12/2011 | Ramer et al. |
| 2011/0320266 A1 | 12/2011 | Ramer et al. |
| 2011/0320267 A1 | 12/2011 | Ramer et al. |
| 2011/0320268 A1 | 12/2011 | Ramer et al. |

(56) References Cited

U.S. PATENT DOCUMENTS

| | | |
|---|---|---|
| 2011/0320269 A1 | 12/2011 | Ramer et al. |
| 2011/0320270 A1 | 12/2011 | Ramer et al. |
| 2011/0320271 A1 | 12/2011 | Ramer et al. |
| 2011/0320279 A1 | 12/2011 | Ramer et al. |
| 2011/0320280 A1 | 12/2011 | Ramer et al. |
| 2011/0320281 A1 | 12/2011 | Ramer et al. |
| 2011/0320282 A1 | 12/2011 | Ramer et al. |
| 2011/0321127 A1 | 12/2011 | Pitroda et al. |
| 2012/0004984 A1 | 1/2012 | Ramer et al. |
| 2012/0004985 A1 | 1/2012 | Ramer et al. |
| 2012/0004986 A1 | 1/2012 | Ramer et al. |
| 2012/0004987 A1 | 1/2012 | Ramer et al. |
| 2012/0004988 A1 | 1/2012 | Ramer et al. |
| 2012/0004989 A1 | 1/2012 | Ramer et al. |
| 2012/0004990 A1 | 1/2012 | Ramer et al. |
| 2012/0004991 A1 | 1/2012 | Ramer et al. |
| 2012/0004992 A1 | 1/2012 | Ramer et al. |
| 2012/0004993 A1 | 1/2012 | Ramer et al. |
| 2012/0004994 A1 | 1/2012 | Ramer et al. |
| 2012/0004995 A1 | 1/2012 | Ramer et al. |
| 2012/0004996 A1 | 1/2012 | Ramer et al. |
| 2012/0004997 A1 | 1/2012 | Ramer et al. |
| 2012/0004998 A1 | 1/2012 | Ramer et al. |
| 2012/0004999 A1 | 1/2012 | Ramer et al. |
| 2012/0005000 A1 | 1/2012 | Ramer et al. |
| 2012/0005001 A1 | 1/2012 | Ramer et al. |
| 2012/0005002 A1 | 1/2012 | Ramer et al. |
| 2012/0005003 A1 | 1/2012 | Ramer et al. |
| 2012/0005004 A1 | 1/2012 | Ramer et al. |
| 2012/0005005 A1 | 1/2012 | Ramer et al. |
| 2012/0005006 A1 | 1/2012 | Ramer et al. |
| 2012/0005007 A1 | 1/2012 | Ramer et al. |
| 2012/0005008 A1 | 1/2012 | Ramer et al. |
| 2012/0005009 A1 | 1/2012 | Ramer et al. |
| 2012/0005010 A1 | 1/2012 | Ramer et al. |
| 2012/0005011 A1 | 1/2012 | Ramer et al. |
| 2012/0005012 A1 | 1/2012 | Ramer et al. |
| 2012/0005013 A1 | 1/2012 | Ramer et al. |
| 2012/0005014 A1 | 1/2012 | Ramer et al. |
| 2012/0005020 A1 | 1/2012 | Ramer et al. |
| 2012/0005077 A1 | 1/2012 | Pitroda et al. |
| 2012/0005078 A1 | 1/2012 | Pitroda et al. |
| 2012/0005079 A1 | 1/2012 | Pitroda et al. |
| 2012/0005080 A1 | 1/2012 | Pitroda et al. |
| 2012/0005081 A1 | 1/2012 | Pitroda et al. |
| 2012/0005082 A1 | 1/2012 | Pitroda et al. |
| 2012/0005083 A1 | 1/2012 | Pitroda et al. |
| 2012/0005084 A1 | 1/2012 | Pitroda et al. |
| 2012/0005085 A1 | 1/2012 | Pitroda et al. |
| 2012/0005086 A1 | 1/2012 | Pitroda et al. |
| 2012/0005087 A1 | 1/2012 | Pitroda et al. |
| 2012/0005088 A1 | 1/2012 | Pitroda et al. |
| 2012/0005089 A1 | 1/2012 | Pitroda et al. |
| 2012/0005090 A1 | 1/2012 | Pitroda et al. |
| 2012/0005091 A1 | 1/2012 | Pitroda et al. |
| 2012/0005092 A1 | 1/2012 | Pitroda et al. |
| 2012/0005725 A1 | 1/2012 | Pitroda et al. |
| 2012/0005726 A1 | 1/2012 | Pitroda et al. |
| 2012/0010945 A1 | 1/2012 | Ramer et al. |
| 2012/0010946 A1 | 1/2012 | Ramer et al. |
| 2012/0010947 A1 | 1/2012 | Ramer et al. |
| 2012/0010948 A1 | 1/2012 | Ramer et al. |
| 2012/0010949 A1 | 1/2012 | Ramer et al. |
| 2012/0010950 A1 | 1/2012 | Ramer et al. |
| 2012/0010951 A1 | 1/2012 | Ramer et al. |
| 2012/0010952 A1 | 1/2012 | Ramer et al. |
| 2012/0010953 A1 | 1/2012 | Ramer et al. |
| 2012/0010954 A1 | 1/2012 | Ramer et al. |
| 2012/0010955 A1 | 1/2012 | Ramer et al. |
| 2012/0010956 A1 | 1/2012 | Ramer et al. |
| 2012/0010957 A1 | 1/2012 | Ramer et al. |
| 2012/0010958 A1 | 1/2012 | Ramer et al. |
| 2012/0010959 A1 | 1/2012 | Ramer et al. |
| 2012/0010960 A1 | 1/2012 | Ramer et al. |
| 2012/0010961 A1 | 1/2012 | Ramer et al. |
| 2012/0010962 A1 | 1/2012 | Ramer et al. |
| 2012/0010963 A1 | 1/2012 | Ramer et al. |
| 2012/0010964 A1 | 1/2012 | Ramer et al. |
| 2012/0010965 A1 | 1/2012 | Ramer et al. |
| 2012/0010966 A1 | 1/2012 | Ramer et al. |
| 2012/0010967 A1 | 1/2012 | Ramer et al. |
| 2012/0010968 A1 | 1/2012 | Ramer et al. |
| 2012/0010969 A1 | 1/2012 | Ramer et al. |
| 2012/0010970 A1 | 1/2012 | Ramer et al. |
| 2012/0010971 A1 | 1/2012 | Ramer et al. |
| 2012/0010972 A1 | 1/2012 | Ramer et al. |
| 2012/0010973 A1 | 1/2012 | Ramer et al. |
| 2012/0010974 A1 | 1/2012 | Ramer et al. |
| 2012/0010975 A1 | 1/2012 | Ramer et al. |
| 2012/0010976 A1 | 1/2012 | Ramer et al. |
| 2012/0010977 A1 | 1/2012 | Ramer et al. |
| 2012/0010978 A1 | 1/2012 | Ramer et al. |
| 2012/0010979 A1 | 1/2012 | Ramer et al. |
| 2012/0011058 A1 | 1/2012 | Pitroda et al. |
| 2012/0011253 A1 | 1/2012 | Friedman et al. |
| 2012/0015644 A1 | 1/2012 | Danford et al. |
| 2012/0016925 A1 | 1/2012 | Brown et al. |
| 2012/0027001 A1 | 2/2012 | Krishnaswamy et al. |
| 2012/0030470 A1 | 2/2012 | Jdanov et al. |
| 2012/0032945 A1 | 2/2012 | Dare et al. |
| 2012/0036010 A1 | 2/2012 | Ramer et al. |
| 2012/0036220 A1 | 2/2012 | Dare et al. |
| 2012/0036245 A1 | 2/2012 | Dare et al. |
| 2012/0036440 A1 | 2/2012 | Dare et al. |
| 2012/0036442 A1 | 2/2012 | Dare et al. |
| 2012/0036552 A1 | 2/2012 | Dare et al. |
| 2012/0041819 A1 | 2/2012 | Ramer et al. |
| 2012/0054848 A1 | 3/2012 | Salowey et al. |
| 2012/0059711 A1 | 3/2012 | Ramer et al. |
| 2012/0059718 A1 | 3/2012 | Ramer et al. |
| 2012/0066057 A1 | 3/2012 | Ramer et al. |
| 2012/0066065 A1 | 3/2012 | Switzer |
| 2012/0066198 A1 | 3/2012 | Ramer et al. |
| 2012/0066199 A1 | 3/2012 | Ramer et al. |
| 2012/0069131 A1 | 3/2012 | Abelow |
| 2012/0084544 A1 | 4/2012 | Farina et al. |
| 2012/0084545 A1 | 4/2012 | Farina et al. |
| 2012/0084562 A1 | 4/2012 | Farina et al. |
| 2012/0084566 A1 | 4/2012 | Chin et al. |
| 2012/0084838 A1 | 4/2012 | Inforzato et al. |
| 2012/0086345 A1 | 4/2012 | Tran |
| 2012/0087319 A1 | 4/2012 | Raleigh et al. |
| 2012/0088470 A1 | 4/2012 | Raleigh |
| 2012/0089699 A1 | 4/2012 | Cholas |
| 2012/0089845 A1 | 4/2012 | Raleigh |
| 2012/0094769 A1 | 4/2012 | Nguyen et al. |
| 2012/0095352 A1 | 4/2012 | Tran |
| 2012/0095357 A1 | 4/2012 | Tran |
| 2012/0095393 A1 | 4/2012 | Reinke et al. |
| 2012/0096513 A1 | 4/2012 | Raleigh et al. |
| 2012/0096524 A1 | 4/2012 | Kovalan |
| 2012/0101831 A1 | 4/2012 | Pitroda et al. |
| 2012/0101832 A1 | 4/2012 | Pitroda et al. |
| 2012/0101833 A1 | 4/2012 | Pitroda et al. |
| 2012/0101834 A1 | 4/2012 | Pitroda et al. |
| 2012/0101835 A1 | 4/2012 | Pitroda et al. |
| 2012/0101836 A1 | 4/2012 | Pitroda et al. |
| 2012/0102143 A1 | 4/2012 | Mandre |
| 2012/0105199 A1 | 5/2012 | Sanders |
| 2012/0105201 A1 | 5/2012 | Sanders |
| 2012/0105214 A1 | 5/2012 | Sanders |
| 2012/0109667 A1 | 5/2012 | Pitroda et al. |
| 2012/0109668 A1 | 5/2012 | Pitroda et al. |
| 2012/0109669 A1 | 5/2012 | Pitroda et al. |
| 2012/0109670 A1 | 5/2012 | Pitroda et al. |
| 2012/0109671 A1 | 5/2012 | Pitroda et al. |
| 2012/0109672 A1 | 5/2012 | Pitroda et al. |
| 2012/0109673 A1 | 5/2012 | Pitroda et al. |
| 2012/0109674 A1 | 5/2012 | Pitroda et al. |
| 2012/0109851 A1 | 5/2012 | Sanders |
| 2012/0110602 A1 | 5/2012 | Sanders |
| 2012/0112531 A1 | 5/2012 | Kesler et al. |
| 2012/0116790 A1 | 5/2012 | Pitroda et al. |
| 2012/0116959 A1 | 5/2012 | Pitroda et al. |

(56) References Cited

U.S. PATENT DOCUMENTS

| | | |
|---|---|---|
| 2012/0118947 A1 | 5/2012 | Lyons et al. |
| 2012/0122528 A1 | 5/2012 | Lyons et al. |
| 2012/0122529 A1 | 5/2012 | Lyons |
| 2012/0122558 A1 | 5/2012 | Lyons et al. |
| 2012/0129503 A1 | 5/2012 | Lindeman et al. |
| 2012/0130811 A1 | 5/2012 | Ramer et al. |
| 2012/0130812 A1 | 5/2012 | Ramer et al. |
| 2012/0131685 A1 | 5/2012 | Broch et al. |
| 2012/0134291 A1 | 5/2012 | Raleigh |
| 2012/0150629 A1 | 6/2012 | Ramer et al. |
| 2012/0158607 A1 | 6/2012 | Burns et al. |
| 2012/0159147 A1 | 6/2012 | Ando |
| 2012/0159438 A1 | 6/2012 | Plate |
| 2012/0159578 A1 | 6/2012 | Chawla et al. |
| 2012/0169468 A1 | 7/2012 | Butler et al. |
| 2012/0169469 A1 | 7/2012 | Butler et al. |
| 2012/0169474 A1 | 7/2012 | Butler et al. |
| 2012/0182123 A1 | 7/2012 | Butler et al. |
| 2012/0185390 A1 | 7/2012 | Palnitkar et al. |
| 2012/0190386 A1 | 7/2012 | Anderson |
| 2012/0191860 A1 | 7/2012 | Traversat et al. |
| 2012/0192249 A1 | 7/2012 | Raleigh |
| 2012/0195206 A1 | 8/2012 | Raleigh |
| 2012/0195222 A1 | 8/2012 | Raleigh |
| 2012/0195223 A1 | 8/2012 | Raleigh |
| 2012/0196565 A1 | 8/2012 | Raleigh |
| 2012/0197709 A1 | 8/2012 | Kendall et al. |
| 2012/0197724 A1 | 8/2012 | Kendall |
| 2012/0197792 A1 | 8/2012 | Raleigh |
| 2012/0201133 A1 | 8/2012 | Raleigh |
| 2012/0203677 A1 | 8/2012 | Raleigh |
| 2012/0204245 A1 | 8/2012 | Ting et al. |
| 2012/0206243 A1 | 8/2012 | Butler et al. |
| 2012/0208496 A1 | 8/2012 | Raleigh |
| 2012/0209750 A1 | 8/2012 | Raleigh |
| 2012/0210130 A1 | 8/2012 | Buer et al. |
| 2012/0210391 A1 | 8/2012 | Raleigh |
| 2012/0210401 A1 | 8/2012 | Pepin et al. |
| 2012/0212596 A1 | 8/2012 | Mathur |
| 2012/0214441 A1 | 8/2012 | Raleigh |
| 2012/0215831 A1 | 8/2012 | Urbach |
| 2012/0216225 A1 | 8/2012 | Britt |
| 2012/0222123 A1 | 8/2012 | Williams et al. |
| 2012/0232367 A1 | 9/2012 | Allegri et al. |
| 2012/0232945 A1 | 9/2012 | Tong |
| 2012/0232970 A1 | 9/2012 | Kara |
| 2012/0233679 A1 | 9/2012 | Shedrinsky |
| 2012/0235503 A1 | 9/2012 | Kesler et al. |
| 2012/0238255 A1 | 9/2012 | Ramer et al. |
| 2012/0240183 A1 | 9/2012 | Sinha |
| 2012/0240196 A1 | 9/2012 | Bhagwat et al. |
| 2012/0240236 A1 | 9/2012 | Wyatt et al. |
| 2012/0242501 A1 | 9/2012 | Tran et al. |
| 2012/0245438 A1 | 9/2012 | Bernini et al. |
| 2012/0245464 A1 | 9/2012 | Tran |
| 2012/0253847 A1 | 10/2012 | Dell'Anno et al. |
| 2012/0254401 A1 | 10/2012 | Adams et al. |
| 2012/0254474 A1 | 10/2012 | Brown et al. |
| 2012/0259978 A1 | 10/2012 | Petersen et al. |
| 2012/0259981 A1 | 10/2012 | Lewinski et al. |
| 2012/0261479 A1 | 10/2012 | Moore et al. |
| 2012/0266221 A1 | 10/2012 | Castelluccia et al. |
| 2012/0266251 A1 | 10/2012 | Birtwhistle et al. |
| 2012/0271380 A1 | 10/2012 | Roberts et al. |
| 2012/0277543 A1 | 11/2012 | Homchowdhury et al. |
| 2012/0278101 A1 | 11/2012 | Homchowdhury et al. |
| 2012/0284416 A1 | 11/2012 | Li et al. |
| 2012/0293324 A1 | 11/2012 | Rao et al. |
| 2012/0294195 A1 | 11/2012 | Raleigh |
| 2012/0297464 A1 | 11/2012 | Busch et al. |
| 2012/0319823 A1 | 12/2012 | Butler et al. |
| 2012/0323717 A1 | 12/2012 | Kirsch |
| 2012/0323786 A1 | 12/2012 | Kirsch |
| 2012/0324067 A1 | 12/2012 | Hari et al. |
| 2012/0324242 A1 | 12/2012 | Kirsch |
| 2012/0324562 A1 | 12/2012 | Bansal et al. |
| 2012/0330109 A1 | 12/2012 | Tran |
| 2012/0330829 A1 | 12/2012 | Raleigh |
| 2013/0003613 A1 | 1/2013 | Raleigh |
| 2013/0005299 A1 | 1/2013 | Raleigh |
| 2013/0005322 A1 | 1/2013 | Raleigh |
| 2013/0006729 A1 | 1/2013 | Raleigh |
| 2013/0006780 A1 | 1/2013 | Raleigh |
| 2013/0007837 A1 | 1/2013 | King |
| 2013/0010945 A1 | 1/2013 | McDonald et al. |
| 2013/0012178 A1 | 1/2013 | Ramer et al. |
| 2013/0014263 A1 | 1/2013 | Porcello et al. |
| 2013/0016636 A1 | 1/2013 | Berger et al. |
| 2013/0024254 A1 | 1/2013 | Libenson et al. |
| 2013/0024257 A1 | 1/2013 | Libenson et al. |
| 2013/0024262 A1 | 1/2013 | Libenson et al. |
| 2013/0024267 A1 | 1/2013 | Libenson et al. |
| 2013/0024364 A1 | 1/2013 | Shrivastava et al. |
| 2013/0024371 A1 | 1/2013 | Hariramani et al. |
| 2013/0024381 A1 | 1/2013 | Dala et al. |
| 2013/0024382 A1 | 1/2013 | Dala et al. |
| 2013/0031201 A1 | 1/2013 | Kagan et al. |
| 2013/0034230 A1 | 2/2013 | Takahashi |
| 2013/0040703 A1 | 2/2013 | Raleigh |
| 2013/0042117 A1 | 2/2013 | Birtwhistle et al. |
| 2013/0045710 A1 | 2/2013 | Raleigh |
| 2013/0053657 A1 | 2/2013 | Ziarno et al. |
| 2013/0054820 A1 | 2/2013 | Reisman |
| 2013/0054962 A1 | 2/2013 | Chawla et al. |
| 2013/0055315 A1 | 2/2013 | Reisman |
| 2013/0055347 A1 | 2/2013 | Chawla et al. |
| 2013/0060703 A1 | 3/2013 | Dala et al. |
| 2013/0061264 A1 | 3/2013 | Reisman |
| 2013/0061273 A1 | 3/2013 | Reisman |
| 2013/0065551 A1 | 3/2013 | Raleigh et al. |
| 2013/0066723 A1 | 3/2013 | Ramer et al. |
| 2013/0066784 A1 | 3/2013 | Dala et al. |
| 2013/0067023 A1 | 3/2013 | Joy et al. |
| 2013/0067526 A1 | 3/2013 | Reisman |
| 2013/0069780 A1 | 3/2013 | Tran et al. |
| 2013/0072770 A1 | 3/2013 | Rao et al. |
| 2013/0072807 A1 | 3/2013 | Tran |
| 2013/0090938 A1 | 4/2013 | Fishman et al. |
| 2013/0095459 A1 | 4/2013 | Tran |
| 2013/0097086 A1 | 4/2013 | Dala et al. |
| 2013/0102963 A1 | 4/2013 | Marsh et al. |
| 2013/0108046 A1 | 5/2013 | Andersen |
| 2013/0109412 A1 | 5/2013 | Nguyen et al. |
| 2013/0110008 A1 | 5/2013 | Bourget et al. |
| 2013/0132109 A1 | 5/2013 | Mruthyunjaya et al. |
| 2013/0147622 A1 | 6/2013 | LaLonde et al. |
| 2013/0154851 A1 | 6/2013 | Gaskill et al. |
| 2013/0159021 A1 | 6/2013 | Felsher |
| 2013/0169432 A1 | 7/2013 | Ozgul et al. |
| 2013/0172691 A1 | 7/2013 | Tran |
| 2013/0176115 A1 | 7/2013 | Puleston et al. |
| 2013/0178718 A1 | 7/2013 | Tran et al. |
| 2013/0197322 A1 | 8/2013 | Tran |
| 2013/0198245 A1 | 8/2013 | Kagan et al. |
| 2013/0204450 A1 | 8/2013 | Kagan et al. |
| 2013/0205022 A1 | 8/2013 | Kagan et al. |
| 2013/0227288 A1 | 8/2013 | Konrad et al. |
| 2013/0231574 A1 | 9/2013 | Tran |
| 2013/0231711 A1 | 9/2013 | Kaib |
| 2013/0247194 A1 | 9/2013 | Jha et al. |
| 2013/0288656 A1 | 10/2013 | Schultz et al. |
| 2013/0297973 A1 | 11/2013 | Hyland et al. |
| 2013/0304489 A1 | 11/2013 | Miller |
| 2013/0310896 A1 | 11/2013 | Mass |
| 2013/0343584 A1 | 12/2013 | Bennett et al. |
| 2013/0346108 A1 | 12/2013 | Kamen et al. |
| 2014/0025321 A1 | 1/2014 | Spanier |
| 2014/0055284 A1 | 2/2014 | Tran et al. |
| 2014/0062718 A1 | 3/2014 | LaLonde et al. |
| 2014/0081665 A1 | 3/2014 | Holmes |
| 2014/0085104 A1 | 3/2014 | Rao et al. |
| 2014/0088434 A1 | 3/2014 | Roth |
| 2014/0088436 A1 | 3/2014 | Roth |
| 2014/0112367 A1 | 4/2014 | Roth |

(56) References Cited

U.S. PATENT DOCUMENTS

| | | |
|---|---|---|
| 2014/0113553 A1 | 4/2014 | Brukalo et al. |
| 2014/0114600 A1 | 4/2014 | Roth |
| 2014/0121476 A1 | 5/2014 | Tran et al. |
| 2014/0129338 A1 | 5/2014 | Nguyen et al. |
| 2014/0153719 A1 | 6/2014 | Kalpin et al. |
| 2014/0162563 A1 | 6/2014 | Mastrototaro |
| 2014/0171856 A1 | 6/2014 | McLaughlin et al. |
| 2014/0180140 A1 | 6/2014 | Alpert |
| 2014/0181949 A1 | 6/2014 | Hunter |
| 2014/0185805 A1 | 7/2014 | Andersen |
| 2014/0187177 A1 | 7/2014 | Sridhara et al. |
| 2014/0194702 A1 | 7/2014 | Tran |
| 2014/0195922 A1 | 7/2014 | Kovalan |
| 2014/0200477 A1 | 7/2014 | Andersen |
| 2014/0203915 A1 | 7/2014 | Puleston et al. |
| 2014/0207486 A1 | 7/2014 | Carty et al. |
| 2014/0221959 A1 | 8/2014 | Gray et al. |
| 2014/0222684 A1 | 8/2014 | Felsher |
| 2014/0228904 A1 | 8/2014 | Rao et al. |
| 2014/0245384 A1 | 8/2014 | Shieh et al. |
| 2014/0249429 A1 | 9/2014 | Tran |
| 2014/0249844 A1 | 9/2014 | Liberty et al. |
| 2014/0266787 A1 | 9/2014 | Tran |
| 2014/0273824 A1 | 9/2014 | Fenner et al. |
| 2014/0276571 A1 | 9/2014 | Ludolph |
| 2014/0281484 A1 | 9/2014 | Kurkowski et al. |
| 2014/0288947 A1 | 9/2014 | Simpson et al. |
| 2014/0288952 A1 | 9/2014 | Smith et al. |
| 2014/0292490 A1 | 10/2014 | Butler et al. |
| 2014/0297642 A1 | 10/2014 | Lum et al. |
| 2014/0298022 A1 | 10/2014 | Proennecke et al. |
| 2015/0006905 A1 | 1/2015 | Avanzi |
| 2015/0026767 A1 | 1/2015 | Sweet et al. |
| 2015/0045022 A1 | 2/2015 | Prechner et al. |
| 2015/0045055 A1 | 2/2015 | Prechner et al. |
| 2015/0046183 A1 | 2/2015 | Cireddu |
| 2015/0058619 A1 | 2/2015 | Sweet et al. |
| 2015/0061840 A1 | 3/2015 | Butler et al. |
| 2015/0066538 A1 | 3/2015 | Dantsker et al. |
| 2015/0069831 A1 | 3/2015 | Kesler et al. |
| 2015/0088334 A1 | 3/2015 | Bowers et al. |
| 2015/0088550 A1 | 3/2015 | Bowers et al. |
| 2015/0089590 A1 | 3/2015 | Krishnan et al. |
| 2015/0094111 A1 | 4/2015 | Kim et al. |
| 2015/0099941 A1 | 4/2015 | Tran |
| 2015/0100890 A1 | 4/2015 | Kosmiskas et al. |
| 2015/0105631 A1 | 4/2015 | Tran et al. |
| 2015/0117408 A1 | 4/2015 | Kedalagudde et al. |
| 2015/0117645 A1 | 4/2015 | Carlson et al. |
| 2015/0125832 A1 | 5/2015 | Tran |
| 2015/0129666 A1 | 5/2015 | Butler et al. |
| 2015/0130593 A1 | 5/2015 | Mats et al. |
| 2015/0135338 A1 | 5/2015 | Moskal |
| 2015/0138089 A1 | 5/2015 | Angerbauer et al. |
| 2015/0142462 A1 | 5/2015 | Vaidya et al. |
| 2015/0143356 A1 | 5/2015 | Charlton et al. |
| 2015/0148697 A1 | 5/2015 | Burnes et al. |
| 2015/0149096 A1 | 5/2015 | Soykan |
| 2015/0164323 A1 | 6/2015 | Holtzclaw |
| 2015/0164372 A1 | 6/2015 | Navab et al. |
| 2015/0180920 A1 | 6/2015 | Hunter |
| 2015/0206408 A1 | 7/2015 | LaLonde et al. |
| 2015/0207622 A1 | 7/2015 | Andersen |
| 2015/0207626 A1 | 7/2015 | Neftel et al. |
| 2015/0211941 A1 | 7/2015 | Roth |
| 2015/0250393 A1 | 9/2015 | Tran |
| 2015/0263907 A1 | 9/2015 | Negishi |
| 2015/0269825 A1 | 9/2015 | Tran |
| 2015/0302234 A1 | 10/2015 | Mats et al. |
| 2015/0304403 A1 | 10/2015 | Kovalan |
| 2015/0310203 A1 | 10/2015 | Shieh et al. |
| 2015/0310228 A1 | 10/2015 | Benz et al. |
| 2015/0324681 A1 | 11/2015 | Mats et al. |
| 2015/0341785 A1 | 11/2015 | Young et al. |
| 2015/0343144 A1 | 12/2015 | Altschul et al. |
| 2015/0347682 A1 | 12/2015 | Chen et al. |
| 2015/0356104 A9 | 12/2015 | Kagan et al. |
| 2015/0356255 A1 | 12/2015 | Simpson et al. |
| 2015/0356264 A1 | 12/2015 | Bernini et al. |
| 2015/0359467 A1 | 12/2015 | Tran |

OTHER PUBLICATIONS

Ross, David Andrew. "Securing IEEE 802.11 wireless LANs." (2010). Ph.D. Thesis Queensland University (2010).

Fischer, Martin. "Enhancing the ReMoteCare prototype by adding an SNMP proxy and video surveillance." (2008). University of Techn., Sydney.

Pankakoski, Veikko. "Experimental design for a next generation residential gateway." (2010). M.S. Thesis Aalto University (2010).

\* cited by examiner

SYSTEM AND METHOD FOR SECURE RELAYED COMMUNICATIONS FROM AN IMPLANTABLE MEDICAL DEVICE

CROSS REFERENCE TO RELATED APPLICATION

The present application is a Continuation of U.S. patent application Ser. No. 15/948,667, filed Apr. 9, 2018, now U.S. Pat. No. 10,305,695, issued May 28, 2019, which is a Continuation of U.S. patent application Ser. No. 14/968,336, filed Dec. 14, 2015, now U.S. Pat. No. 9,942,051, issued Apr. 10, 2018, which is a Continuation of U.S. patent application Ser. No. 14/214,077, filed Mar. 14, 2014, now U.S. Pat. No. 9,215,075, issued Dec. 15, 2015, which is a non-provisional of and claims benefit of priority under 35 U.S.C. § 119(e) from U.S. Provisional Patent Application No. 61/799,720, filed Mar. 15, 2013, the entirety of which are expressly incorporated herein by reference in their entirety.

FIELD OF THE INVENTION

The present invention relates to the field of implantable medical devices, and more particularly implantable medical devices having wireless data communications transceivers.

BACKGROUND OF THE INVENTION

The present invention relates generally to systems and methods for providing secure and private communication channels for implantable medical devices using public communication networks and potentially insecure devices as intermediaries.

Implantable and programmable personal medical devices are becoming common. In some cases, these represent applications ("apps") for smartphones. In other cases, regulated medical devices communicate through commercial off the shelf technologies. In both these cases, it is possible for provide communications to be intercepted, revealing potentially personal or confidential information. Further, it may be possible to modify communications, leading to misdiagnosis, improper treatment, or other harm.

For example, a smartphone app or the platform on which a smartphone app executes may include security vulnerabilities, even if the app is digitally signed. For example, of the medical device is a defibrillator, this could be reprogrammed to fail to generate a required discharge, or to discharge in a harmful or lethal pattern.

It is therefore desirable to make use of ubiquitous consumer technologies for communications, while isolating the privacy and security risks inherent in such technologies.

Øyvind Børthus and Tomas Mikael Engh, "Privacy protection in a mobile Biomedical Information Collection Service", (Master's Thesis), Agder University College, Grimstad Norway (May 2005), expressly incorporated herein in its entirety, presents FIG. 1 which indicates a problem which persists to this day. How does one secure the communication from the patient to a provider, and from the provider to the patient, where the data communicated is private, and corruption of that data may be life-threatening? Børthus and Engh do not consider security of the "handheld device" as an issue to be addressed.

The use of a mobile wireless sensor gives the patient the possibility of being at home and doing his or hers normal daily activities while being monitored, but it also creates the need for new mechanisms for privacy protection. Fensli, R., E. Gunnarson, and T. Gundersen (2005) "A Wearable ECG-recording System for Continuous Arrhythmia Monitoring in a Wireless Tele-Home-Care Situation," presented at The 18th IEEE International Symposium on Computer-Based Medical Systems, Dublin, Ireland. For the patient to stay in his normal environment gives several benefits for both the patient and the quality of the monitoring. The patient will be more relaxed and the recordings will not be affected by the stressful situation at a hospital.

A mobile wireless sensor is a compact electronic electrode attached to a patient that can measure different biomedical signals. In this scenario we are using a sensor for electrocardiogram (ECG) recordings as an example. This sensor will continuously measure and wirelessly transmit sampled ECG-recordings using a built-in RF-radio transmitter. The RF-radio receiver converts the ECG-samples by the use of a microcontroller before transmitting the ECG-samples to a standard personal digital assistant (PDA). The sensor measures ECG-signals with a sampling frequency up to 1000 samples per second. Crawford, M. H. et al. (1999) "ACC/AHA Guidelines for Ambulatory Electrocardiography: Executive summary and Recommendations" American College of Cardiology. The signal is digitalized with 10-bit resolution, requiring up to 10 kb/s of bandwidth plus overhead to transmit to the PDA. The range of the RF-radio signal is up to 10 meters. The transmitter chip used by the sensor described in Fensli et al. is a RF-transmitter CC1050 from ChipCon, operating at 869.700 MHz, with a bit rate of up to 76.8 kbit/s. The sensor will transmit continuously, and will be attached to the patient for 3 days to a week at a time. The sensor is a disposable unit, and will only be used once.

A PDA is used to receive the information from the sensor of Fensli et al. and will often have 400 to 600 MHz processor, 64 to 128 MB of internal memory and a memory card with capacity of more than 2 GB for storing data. The PDA has both a short range wireless RF-radio device and a GPRS card installed. The PDA is an "intelligent" unit, using automatic arrhythmia detection algorithms for analyzing the signals from the sensor and decides if the recordings are within normal values. As long as the signals are within normal values the PDA will regularly send an extract of the recordings to an electronic health register (EHR) connected to the Internet by the use of GPRS communication. If an abnormal ECG activity is encountered, the PDA will store 1 minute of the ECG recordings and then transmit the recordings to the EHR server.

There are several security and privacy threats relevant to this scenario. From a medical standpoint it is very important that the PDA only receives data from the correct sensor, and not from other devices in the same area. Keeping the integrity of the data is also very important to avoid false alarms or incorrect normal signals. The data must also be protected in such a way that possible attackers cannot get access to personal information about the patient.

For the transmission of data from the PDA to the EHR, and between users in the national health network many of the same threats applies. Integrity, security and privacy must be protected when sending electronic messages containing sensitive medical and personal information. The electronic messages contain a lot more sensitive information than the data packets sent from the sensor and thus require a higher level of security protection. Non repudiation is especially important when sending messages regarding medication and diagnosis.

Bluetooth is a short range radio standard designed for low power consumption. On Jun. 14, 2002 the Bluetooth standard was published as IEE 802.15.1. Subsequent versions have been published. Bluetooth operates in the unlicensed industrial, scientific and medical (ISM) band at 2.4 to 2.485 GHz, using a spread spectrum, frequency hopping, full-duplex signal at a nominal rate of 1600 hops/sec. Bluetooth SIG (2004) "Specification of the Bluetooth System". The adaptive frequency hopping (AFH) was designed to reduce interference between wireless technologies using the 2.4 GHz spectrum. The AFH detects other devices and avoid the frequencies used and can take advantage of the available frequencies. The AFH hops among 79 frequencies at 1 MHz intervals to give high interference immunity. The range of Bluetooth devices range from 1 to 100 meters depending on the device class used. Class 1 devices use a power of 100 mW giving it a range of up to 100 meters, class 2 uses 2.5 mW and have a range of up to 10 meters, and class 3 uses 1 mW and have a range of up to 1 meter. Class 2 is the most commonly used. Version 1.2 has a gross data rate of up to 1 Mbit/s and Version 2.0 with Enhanced Data Rate (EDR) has a gross data rate of up to 3 Mbps. The effective transfer rates are respectively 723.1 kbit/s and 2.1 Mbit/s. Bluetooth devices communicate in small groups of up to 8 devices, called a piconet. One device plays the "master" and the rest (up to 7) devices are "slaves". Data can be transferred between master and 1 slave at any given time, and the master switches between slaves in a round robin fashion. Simultaneous transmission from master to multiple slaves is possible, but rarely used.

A Bluetooth device will transmit the following sets of information on demand: Device name; Device class; List of services; and Technical information. Any device can perform an inquiry to find other devices with which to connect, and any device can be configured to respond to such inquiries. If the device trying to connect knows the address to the device, it will always respond to inquiries with the information mentioned above if requested for it. Use of the devices services may require pairing or owner accept, but the connection itself can be established by any device and held until it goes out of range. All devices have a unique 48-bit address, but these are generally not shown in inquiries and instead user friendly "Bluetooth names" are used. These names can be set by the user and most devices come with a standard name set by the manufacturer. All devices also have a 24-bit class identifier, providing information about what class of device it is, for example mobile phone, headset or computer.

Bluetooth devices can be paired to establish a trusted connection. By user input (a pin code) they can learn a shared secret key known as a "passkey". A device can then cryptographically authenticate the identity of another device. With some devices, like wireless earphones, it is impossible for the user to enter a pin code, and the device has a fixed pin code, which can be entered into the peer device. Trusted devices can also encrypt information they transmit so no one can "listen in". The encryption can be turned off, and the passkey is stored in the device's memory, and not in the Bluetooth chip itself. The trusted connection can be canceled by either device at any time. Devices will generally require pairing or user input before it allows a remote device to use its services.

In order to communicate with other Bluetooth devices a device must be able to interpret certain Bluetooth profiles. These profiles define the possible applications. 24 profiles are defined and adopted by the Bluetooth SIG, for example: Generic Access Profile (GAP) which provides the basis for all other profiles. This profile describes which features must be implemented in all Bluetooth devices, generic procedures for discovering and linking to devices, and basic user-interface terminology; Basic Imaging Profile (BIP). This profile is designed for sending images between devices and includes the ability to resize, and convert images to make them suitable for the receiving device; and Human Interface Device Profile (HID) provides support for devices such as mice, joysticks, keyboards, etc.; Advanced Audio Distribution Profile (A2DP). Also referred to as the AV profile, it is designed to transfer a stereo audio stream like music from an MP3 player to a headset or car radio.

On the link layer Bluetooth uses the SAFER+ algorithm for authentication and key generation, and E0 stream cipher for encrypting packets. The link layer security is independent of possible application layer security. The SAFER+ (Secure and Fast Encryption Routine) algorithm is a block cipher with block size of 128 bits, and a default key size of 128 bits. Wikipedia.org "SAFER" en.wikipedia.org/wiki/SAFER. The cipher uses 8 rounds with 4 stages; a key-mixing stage, a substitution layer, another key-mixing stage, and finally a diffusion layer. The E0 is a stream cipher. Wikipedia.org "E0 (cipher)", en.wikipedia.org/wiki/E0_(cipher). It generates a sequence of pseudorandom numbers and combines it with the data using a XOR operator. The key length is usually 128 bits, but may vary. For each iteration E0 generates a bit using 4 shift registers of different length (25, 31, 33, 39 bits), and two internal states, each 2 bits long. For each clock cycle, the registers are shifted and the two states are updated with the current state, the previous state and the values in the shift registers. Four bits are then extracted from the shift registers and added together. Then the algorithm XORs that sum with the value in the 2-bit register. The first bit of the result is output for the encoding. E0 is divided in three parts: 1. Payload key generation; 2. Key stream generation; and 3. Encoding.

The setup of the initial state in Bluetooth uses the same structure as the random bit stream generator. We are thus dealing with two combined E0 algorithms. Using the 128-bit key, Bluetooth address on 48 bits and the 26-bit master counter an initial 132-bit state is produced at the first stage. The output is then processed by a polynomial operation and the resulting key goes through the second stage, which generates the stream used for encoding. The key is a multiple of 2 varying from 8 to 128-bits length. 128 bit keys are generally used. These are stored into the second stage's shift registers. 200 pseudorandom bits are then produced, and the last 128 bits are inserted into the shift registers. It is the stream generator's initial state.

Shaked and Wool showed (Shaked, Y. and A. Wool (2005) "Cracking the Bluetooth PIN" Shaked, Yaniv, and Avishai Wool. "Cracking the bluetooth pin." In Proceedings of the 3rd international conference on Mobile systems, applications, and services, pp. 39-50. ACM, 2005; www.eng.tau.ac.il/~yash/shaked-wool-mobisys05/index.html (May 2, 2005)) that the PIN code used by some devices to add security can be easily broken, even on an old computer. They described a passive attack, in which an attacker can find the PIN used during the pairing process. They used less than 0.3 seconds to crack a 4-digit pin, as used by most devices using a pin code, on a Pentium III 450 MHz computer and even faster on a new 3 GHz Pentium IV. If two Bluetooth devices perform pairing in a hostile area, they are vulnerable to this attack. Lu, Meier, and Vaudenay (Lu Y., W. Meier, and S. Vaudenay (2005) "The Conditional Correlation Attack: A Practical Attack on Bluetooth Encryption" Crypto'05, Santa Barbara. CABA "Standards and protocols" www.caba.org/standard/zigbee.html (Jan. 18, 2006)) presented an attack on the E0 stream cipher. Using a conditional correlation attack developed and optimized against Bluetooth two-level E0 they attack a recently detected flaw in the resynchronization of E0. Their best attack finds the original encryption key for two-level E0 using the first 24 bits of 223.8 frames and with 238 computations. This is the fastest and so far only practical known-plaintext attack on Bluetooth encryption.

ZigBee Alliance was incorporated in August 2002, and announced the ZigBee standard in December 2004. The ZigBee standard was released public in June 2005. Other wireless transfer methods are focusing on transferring large amount of data as fast as possible, but ZigBee is going the other direction. It focuses on low powered devices with a need for security and sending small amounts of data. The ZigBee standard was created to "enable reliable, cost-effective, low-power, wirelessly networked, monitoring and control products based on an open global standard" ZigBee Alliance "Our Mission". www.zigbee.org/en/about/(online May 25, 2006). The most common devices that use ZigBee are industrial automation, remote metering, embedded sensors, medical devices, smoke and intruder alarms, interactive toys, building automation and home automation. ZigBee operates in the European 868 MHz ISM band with one channel, the American and Australian 915 MHz ISM band with 10 channels or the 2.4 GHz ISM band with 16 channels. The data rate is 250 kbit/s in the 2.4 GHz band, 40 kbit/s in the 915 MHz band, and 20 kbit/s in the 868 MHz band. ZigBee Alliance (2004) "ZigBee Specification v1.0"; Kinney, P. (2003) "ZigBee Technology: Wireless Control that Simply Works", Kinney Consulting LLC, Chair of IEEE 802.15.4 Task Group, Secretary of ZigBee BoD, Chair of ZigBee Building Automation Profile WG. Transmission range is typical between 10 and 75 meters. The ZigBee protocol supports up to 65,536 nodes. It has handshaking for transfer reliability.

The ZigBee stack architecture is based on the standard seven-layer c is controlling the access to the radio channel. The mechanism used is called CSMA-CA. The MAC layer also transmits beacon frames, synchronization, and provides reliable transmission mechanisms. The network layer has 3 main functions: join and leave networks, apply security, and route frames to their destinations. In a coordinator device, the network layer has the responsibility to start a new network and discover what kind of application services nearby devices. It also assigns addresses to newly assigned devices. The network layer supports star, cluster three and mesh topology. As mentioned above, the APL layer consists of Application Support sub-layer (APS), ZigBee Device Object (ZDO) and manufacturer-defined applications. The APS is responsible for maintaining the tables for binding i.e. the ability to match two devices and forward the messages between two devices. The ZDO define the role of a device in the network (network coordinator, coordinator, or end device), initiate and/or respond to binding requests, and establish a secure connection.

ZigBee has several different security mechanisms (ZigBee Alliance (2005) "ZigBee Security specification overview"), and are found in the MAC layer, NWK layer and the APS layer. Among them are freshness, integrity, authentication, and encryption. The freshness checks prevent replay attacks. It uses incoming and outgoing freshness counters that are reset every time a new key is created. The integrity checks prevent anyone from modifying the message, and supports up to 128-bit message integrity. Authentication is handled either in the network level or the device level. The network level authentication is achieved when using a common network key. This will prevent attacks from outsiders, and it has very little memory cost. The device level authentication is achieved when using unique link keys between pair of devices. This prevents attacks from both outsiders and insiders, but has a higher memory cost. ZigBee supports 128 bit AES encryption. This encryption can be used either at network level or device level, and is handled the same way as authentication. The encryption can be turned on or off without impacting the freshness, integrity or authentication. ZigBee can also add security to frames. ZigBee Security can add headers to the data frames at the MAC, NWK, and APS layers. ZigBee supports 3 types of topologies: Star, Cluster tree and Mesh.

In a star topology the network is controlled by a PAN coordinator (network controller). All end devices can only talk to the coordinator. The coordinator is almost always in a listening mode, except when new end devices are trying to connect. The star topology supports up to 65,536 end devices. It is a very simple layout and has low latency. Øyen, G.E. (2006) "ZigBee and IEEE 802.15.4: A brief introduction". In a cluster tree topology the tree structure is rooted at the PAN coordinator. The coordinator initiates the network, and the children (end devices) routes through parents in a hierarchy. It uses a multi-hop topology to increase the network range. The cluster tree topology is not ideal for network devices that require low latency. The idea with mesh topology is that messages can be routed from any source to any destination. The way this is done is that every FFD is functioning as a router for all its neighbors. Like cluster tree topology, the mesh topology uses multi-hop topology to increase the network range. It has high reliability, since the messages can go many routes. If one or more of FFD disconnects, the messages still gets to the destination, but uses another route than it normally does. This way it is self-configuring. Since this topology depends on the routers, it may not be ideal for battery driven networks, as the routers will have relatively large power consumption.

Only one Zigbee coordinator (ZC) is required in each ZigBee network. It is the most capable device in the network, and initiates the formation. It is the root of the network tree, and might bridge to other networks. It acts as a PAN coordinator (FFD) and as a router when the network is formed. The ZC also acts as a repository for security keys. The coordinator is also assumed to be the trust center, which is responsible for allowing new devices into the network and for distributing keys. It is possible for the trust center to be a dedicated device. The Zigbee Router (ZR) is an optional component in a ZigBee network. The routers associate with the ZC or with other previously associated ZR. The ZR acts as a coordinator (FFD) and is used as a local address allocation/de-allocation device. It is used in multi-hop routing of messages. The ZR also looks after its own Zigbee End Device (ZED). The ZED contains very little functionality. It is limited to communicate with its coordinator. The ZED is not allowed to associate or participate in routing. It requires the least amount of memory and is therefore cheaper than ZC or ZR. It has low power consumption since its parent puts it to sleep.

When a new device is installed in the network, it will initiate queries to discover already active ZigBee devices in the network. The request is either an IEEE address request, which is unicast, or a NWK address request, which is broadcast. When the unicast request is sent, it assumes the NWK address is known. When the broadcast request is sent, it carries the known IEEE address as payload. The response on these queries is dependent on the three device types mentioned above: ZED, ZR and ZC. The ZED responds to the query by sending its own IEEE or NWK address. The ZR responds to the query by sending its own IEEE or NWK as well as the IEEE and NWK address of all the other devices connected to the ZR. The ZC responds to the query by sending its own IEEE or NWK as well as the IEEE and NWK address of all the other devices connected to the ZC.

There are 3 different key types used in ZigBee; master key, link key and network key. The master key is used as basis for long term communication between devices, and can be either factory installed or be set up over the air or using out-of-band mechanisms. The link key is used for security between two devices. The link key is also used to authenticate devices to the coordinator device. The network key is used for security in a network. The link and network keys can be factory installed, be set up using a symmetric key-key exchange handshake or be sent from the trust center.

A wide range of ZigBee transceivers that are suited for use in a wireless sensor are available on the commercial market, from suppliers like ChipCon, CompXs, Helicomm Inc. and others. Newer models can come with built in hardware support for data encryption and authentication using AES on the link layer. An example of such a chip is the ChipCon CC2510. ChipCon "CC2510 Product Information" www-.chipcon.com/index.cfm?kat_id=2&subkat_id=12&dok_id=258 (online May 24, 2006). The CC2510 is a powerful 2.4 GHz ISM band System-on-Chip designed for low-power and low-voltage wireless communication applications. This chip includes a dedicated 128-bit AES coprocessor to minimize the MCU usage when encrypting. It also has a dedicated DMA controller which moves data from a peripheral (in our case the sensor) to the memory with almost no intervention from the MCU. This way the MCU workload is reduced to a minimum. The chip has a 32 kB of programmable flash memory and 4 kB of RAM. This chip is developed to be energy efficient and have a low unit cost.

The ZigBee device installed in the PDA will most likely be an SD or CF card. Since our PDA must have a GPRS card, which usually is a CF card, the ZigBee card will be an SD card. An example of a ZigBee SD card is produced by C-Guys. C-GUYS www.c-guysusa.com (online May 24, 2006). They are a company that specializes in developing different SD and SDIO devices, such as SD controllers, memory cards, adapters and card readers. One of their products is a ZigBee SDIO card for use in PDA. The SDIO card is using the standard ZigBee frequency, the 2.4 GHz ISM band, has 250 kbps data rate and 10-meter range.

GSM offers several security services (Schiller, J. (2003) Mobile Communications, second edition, Addison-Wesley, pages 93-156), and they are found either in the SIM card or the AuC (authentication center, a separate system in the network that contains the algorithms for authentication and the keys for encryption). The SIM card stores personal data and a secret key Ki, and is only accessed with a four-digit PIN number. After MS authenticates itself, the MS and BTS (base transceiver station) encrypts all voice and data. There are 3 types of algorithms: A3 for authentication, A5 for encryption and A8 for generation of the cipher key. The algorithms are very weak, but it is possible for the network providers to use stronger algorithms for encryption or user can provide stronger end-to-end encryption. To encrypt the messages, a key Kc is created by using the individual key Ki and a random number by generated by the A8 algorithm. The Kc key is calculated both in the MS (SIM) and the network, and is not transmitted over the air interface.

GPRS (general packet radio service) is a packet-oriented operation in the GSM system, often called 2.5G, since the technology lies somewhere between 2G and 3G (2nd and 3rd generation mobile technology). en.wikipedia.org/wiki/GPRS (May 24, 2006). The idea behind GPRS is Wikipedia.org "GPRS" that all or some GSM-channels (time slots) are combined to one channel with higher capacity. Schiller, J. (2003) Mobile Communications, second edition, Addison-Wesley, pages 93-156. While GSM was primarily designed for voice transmission, GPRS is a more data-oriented transmission. The transmission is packet-oriented so that many users can transfer data when they need it, and don't use bandwidth when they have nothing to send. This type of transmission is especially designed for frequent transmission of small volumes of data, e.g., typical web requests or web response. The overall goal is the provision of a more effective and cheaper packet transfer for typical Internet applications that rely solely on packet transfer. The ISP is usually taking charge for the data volume transferred instead of charging for the connection time. Andersen P. B. og R. Johnsen "Mobiltelefon—Ikke bare prat" in (Ed.) Kunnskapsforlagets Årbok 2000 fag.grm.hia.no/ragnarj/mobile_syst/tradlos_komm.pdf. By doing it this way, the user is "always on", and no connection has to be set up for the transfer.

For each new GPRS radio channel, the GSM can locate between one and eight time slots within a TDMA frame. Schiller, J. (2003) Mobile Communications, second edition, Addison-Wesley, pages 93-156. All time slots can be shared by the active users. It is possible to get a transfer rate to 170 kbit/s if you have max slots and are using the fastest coding, but a more realistic bit rate is 30-80 kbit/s. Wikipedia.org "GPRS" en.wikipedia.org/wiki/GPRS (May 24, 2006). CS-4 is the fastest coding scheme, but the least robust. This coding is available near the Base Transceiver Station (BTS). CS-1 is the slowest coding scheme but is most robust and is available when the Mobile Station (MS) is further away from the BTS. The GPRS operators usually reserves at least one-time slot per cell to guarantee a minimum data rate. Users can specify a QoS-profile themselves. This determines the service precedence (high, normal, low), reliability class and delay class of the transmission and user data throughput. The latency of GPRS is incurred by channel access delay, coding for error correction, and transfer delay in the fixed and wireless parts of the network. Due to these parts involved, the latency is very high, even with small packet sizes. A round trip is often higher than 1 sec, even with packets as small as 128-bytes. Table 2 shows some examples of the delay classes with different service data units (SDU) sizes. A MS (Mobile Station) that are using GPRS are considered a part of the internet and are assigned a private IP address. The operator translates the IP address into global addresses at the GGSN (Gateway GPRS support node) using a NAT (Network Address translation). The advantage of this approach instead of giving the MS an "ordinary" IP address is to protect the MS against attacks. The private IP addresses are not routed through the internet, so it is impossible to reach an MS from the internet. Other security mechanisms are the same as GSM.

EDGE (enhanced data rates for GSM evolution) is a digital enhancement of GSM, and the next step towards 3G and UMTS (EDGE is also called 2.75G, Wikipedia.org, "2.75G" en.wikipedia.org/wiki/2.75G (Mar. 23, 2006)). EDGE is using an enhanced modulation scheme and other techniques to get data rates up to 384 kbit/s using the same carrier size and frequencies as GSM. EDGE does not require any changes in the GSM core networks, but the base stations have to be upgraded. Wikipedia.org "EDGE" en.wikipedia.org/wiki/EDGE (May 24, 2006). Besides better data rate, the most important addition to GSM is CAMEL (customized application for mobile enhanced logic). CAMEL is an intelligent network support, and the services offered are especially effective when a subscriber is roaming between international network operators. Meskauskas, P., "Customised Applications for Mobile Enhanced Logic (CAMEL)". Examples are no-prefix dialing and seamless MMS messages from other countries. EDGE is backward compatible with GPRS, and will use GPRS as transmission in those areas without EDGE support. Norway's largest telecommunication company, Telenor, has very good national EDGE coverage (Telenor Dekningskart telenormobil.no/dekning-innland/index.do (online May 25, 2006) www.telenor.no/bedrift/produkter/mobil/merom_umts_edge.html), and offers a download rate of 100-200 kbit/s and upload rate of 50-75 kbit/s.

UMTS (universal mobile telecommunication system) is a third generation mobile technology used in Europe and Japan, and the 3G successor of GSM. Wikipedia.org "UMTS" en.wikipedia.org/wiki/UMTS (May 23, 2006). To avoid very high implementation cost, UMTS try to reuse as much GSM/GPRS technology and infrastructure as possible. It is especially designed for high-speed services like video telephony. All signals use the same frequency band, a 5 MHz wide band licensed to network operators. The signals are multiplied with a chipping sequence which is unique to each user. If someone tries to tap the signal, it would appear as noise to him if he doesn't know the spreading code. In its initiation phase, UMTS has a theoretical bit rate of 384 kbit/s in high mobility situations, and up to 2 Mbit/s in stationary user environments. UMTS Forum, "What is UMTS?" www.umts-forum.org/servlet/dycon/ztumts/umts/Live/en/umts/What+is+UMTS_index (online May 25, 2006). It takes twice as many base stations as GSM to achieve the same coverage, and to get fully fledged UMTS features including Video on Demand, a base station need to be set up every 1-1.5 km. Some of the downsides of UMTS (as it is today) are: very poor coverage, poor battery life on the MS, impossible to provide complete UMTS features in rural areas, and lack of consumer demand for 3G.

Hash functions are the most versatile of all cryptographic primitives. Bishop, M.

(2003) Computer Security Art and Science, Addison-Wesley. It can be used for encryption, authentication, and a simple digital signature. The typical use of a hash function is digital signatures. The idea behind hashing is to take a long string of bits (or bytes) as input, run a hash function, and produce a fixed length hash sum. Mao, W. (2004) Modern Cryptography Theory & Practice, Bristol, Prentice Hall. If you have a message (m) and a hash (h), you are signing h(m) instead of signing m. The reason for signing h(m) is that the message (m) are usually very large, up to millions of bits, but the hash functions are usually between 128 and 256 bits, thus making it much faster and more effective. One of the practical problems with selecting a hash function, is that there's only a couple methods to choose from Wikipedia.org "Cryptographic Hash Function" en.wikipedia.org/wiki/Cryptographic_hash_function (Apr. 25, 2006); the SHA family and MD5. There are a couple of alternatives, but they have not been tested thoroughly enough to trust them. A typical hash function is shown below. MD5 is a cryptographic hash function used to verify data integrity. Rivest, R. (1992), MIT laboratory for Computer Science and RSA Data security, Inc. April 1992. It was developed by Ronald Rivest in 1991 to replace MD4, because MD4 proved to have some security weakness. When using MD5, the message is split into blocks of 512 bits. Answers.com "MD5" www.answers.com/topic/md5#after_ad1 (online May 25, 2006). The last block is padded, and includes the length of the message. MD5 has 128-bit hash value that is split into four words of 32 bits, each with a compression function h' with four rounds. Each round mix the message block and the state, with a combination of addition, XOR, AND, OR and rotation operations on 32-bit words. This way each message word is used four times. After the four rounds of the h' function, the input state and the result are added together to produce the output of h'. The structure of operating 32-bits words is very efficient on 32-bits CPUs.

One of the basic ideas behind hash functions is that it is collision resistant. As of 2006, there were no known attacks on the MD5 function, but a collision of the compression function occurred in 1996. For modern applications, the 128-bit hash size is insufficient, and it is possible to find real collisions in about 264 evaluations of the hash function. This made security experts to recommend a replacement. One of them was SHA-1. SHA (Secure Hash Algorithm, Wikipedia.org "SHA Hash functions" en.wikipedia.org/wiki/SHA (May 6, 2006)) is a set of cryptographic hash functions. The first standard was just called SHA, but is now referred to as SHA-0. It was developed in 1993 by NSA (National Secure Agency) and published as a US government standard. It was found a weakness in this function, and NSA developed a fix which they published as an improved version called SHA-1.

SHA-1 (National Institute of Standards and Technology (1995) "Secure Hash Standard" www.itl.nist.gov/fipspubs/fip180-1.htm (online May 25, 2006)) is the successor of SHA-0 (and MD5) (Wikipedia.org "SHA Hash functions" en.wikipedia.org/wiki/SHA (May 6, 2006)), and was developed in 1995. It is used in a wide area of security applications, like TLS, SSL, PGP, SSH, S/MIME, and IPSec. SHA-0 and SHA-1 is based on the same principles as MD4 and MD5, and produces a 160-bit message digest with a maximum size of 264 bits. It is, unfortunately, 2-3 times slower than MD5. SHA-1 has a 160-bit state consisting of five 32-bit words. It uses four rounds that consist of a mixture of 32-bit operations. SHA-1 uses a linear recurrence to stretch the 16 words of a message block to the 80 words it needs, to ensure that each message bit affects the mixing function at least a dozen times.

The main problem with SHA-1 is the 160-bit result size. Collisions can be generated in only 280 steps, but it is reported that it can be generated in as few as 263 steps. Schneier, B. (2005), "New Cryptanalytic Results Against SHA-1" www.schneier.com/blog/archives/2005/08/new-_cryptanalyt.html (Aug. 17, 2005).

3TDES has following specification: Three 56-bit DES keys=168 bits+parity bits=192 bits. The effectiveness is counted as only 112 bits because of the exposure to the man-in-the-middle attacks. The best know attack on the 3TDES requires 232 known plaintexts, 2113 steps, 290 single DES encryptions and 288-bit memory. 3TDES is no longer considered a very good encryption method. It is being replaced by its successor, AES with its better security mechanisms. AES has a larger block size, longer keys, freedom from crypto analytic attacks, and proves to be up to six times faster than 3TDES.

Advanced Encryption Standard (AES, Wikipedia.org "Advanced Encryption Standard" en.wikipedia.org/wiki/Advanced_Encryption_Standard (May 24, 2006)), also known as Rijndael is a block cipher. In 2000 NIST, National Institute of Standards and Technology, chose Rijndael as the new encryption standard for the US government. NIST selected the Rijndael algorithm in front of 4 other competitors based on the combination of security, performance, efficiency, ease of implementation and flexibility. Rijndael is a block cipher and uses a substitution-linear transformation network with 10, 12 or 14 rounds, depending on the key and block size. The key and block size can be individually specified to 128, 192 or 256-bits. A data block to be encrypted by Rijndael is split into an array of bytes, and each encryption operation is byte-oriented. Only block size of 128-bits is adopted in the AES standard. The AES does not describe how to handle and distribute keys, and need a secure key management infrastructure to maintain its high level of security. AES is about 6 times faster than 3DES in software implementations.

AES is a block cipher with a fixed block size of 128 bits and a variable key size of 128, 192 or 256 bits. The 128-bit message input block is segmented into 16 bytes. The data structure for their internal representation is a 4×4 matrix. Like the DES algorithm, AES comprises a plural number of iterations of a basic unit of transformation: "round". Depending on the size of the key, AES uses 10, 12 or 14 rounds. A round transformation in AES is denoted by: Round (State, RoundKey). State is a round-message matrix, and is treated as both input and output and a length of 128 bits; RoundKey is a round-key and is derived from the input-key via key schedule. All round-keys are 128-bits, also when the encryption key is 192 or 256-bits. The key schedule is an algorithm for computing the sub-keys for each round in a product cipher from the encryption (or decryption) key. The execution of a round will cause the elements in of State to change value. For encryption the State input to the first round is the plaintext message matrix, and the output from the last round is the cipher text message matrix. For decryption they are respectively cipher text and plaintext message matrix. Each round, except the last round, consists of 4 stages: 1. SubBytes; 2. ShiftRows; 3. MixColumns; and 4. AddRoundKey. All rounds are identical with the exception of the final round, which does not include the MixColumns transformation. The round transformations are invertible for the purpose of decryption.

The SubBytes function provides a non-linear substitution on each byte of State. In the SubBytes step, each byte in the array is updated using an 8-bit S-box. A substitution box (or S-box) is a basic component of symmetric key algorithms, and takes some number of input bits, m, and transforms them into some number of output bits, n. This operation provides the non-linearity in the cipher. The S-box used is derived from the inverse function over $GF(2^8)$, known to have good non-linearity properties. Non-linearity is an important property for a block cipher to prevent differential cryptanalysis. The ShiftRows step operates on the rows of the state; it cyclically shifts the bytes in each row by a certain offset. For AES, the first row is left unchanged. Each byte of the second row is shifted one to the left. Similarly, the third and fourth rows are shifted by offsets of two and three respectively. In this way, each column of the output state of the ShiftRows step is composed of bytes from each column of the input state. In the MixColumns step, the four bytes of each column of the state are combined using an invertible linear transformation. The MixColumns function takes four bytes as input and outputs four bytes, where each input byte affects all four output bytes. Each column is treated as a polynomial over $GF(2^8)$ and is then multiplied modulo $x^4+1$ with a fixed polynomial $c(x)=3 \times 3+ \times 2+x+2$. ShiftRows and MixColumns are intended to achieve a mixture of the bytes positioned in different places of a plaintext message block. In the AddRoundKey step, the subkey is combined with the state. For each round, a subkey is derived from the main key using the key schedule; each subkey is the same size as the state. The subkey is added by combining each byte of the state with the corresponding byte of the subkey using bitwise XOR. This stage provides necessary secret randomness to the message distribution. To decrypt, the 4 functions of each round are inverted, and implemented in reverse order. The AddRoundKey is its own inverse and the same for both encryption and decryption. Three different key lengths, 128, 192, and 256 are supported by AES, making it possible to choose stronger security or better efficiency. All key lengths are secure enough to be used for most levels of classified information. Only for extreme security requirements is it required to use 192 or 256-bit key lengths. The American National Security Agency has conducted a research on the strength of the AES algorithm (CNSS (2003) "CNSS Policy No. 15, Fact Sheet No. 1. National Policy on the Use of the Advanced Encryption Standard (AES) to Protect National Security Systems and National Security Information") stating: "The design and strength of all key lengths of the AES algorithm (i.e., 128, 192 and 256) are sufficient to protect classified information up to the SECRET level. TOP SECRET information will require use of either the 192 or 256-bit key lengths."

Public Key Infrastructure (PKI) is a policy to establish a secure method for information exchange. Bishop, M. (2003) Computer Security Art and Science, Addison-Wesley. It is also a set of integrated services and administrative tools to create and manage applications based on public keys. This includes cryptographic methods, the use of digital certificates, certification authorities, and the system to manage the process. There are two key elements in PKI: Public Key Cryptography and Certification Authorities (CA). Public Key Cryptography is a form of cryptography and uses a pair of cryptographic keys designed as a private key and a public key, which are related mathematically. The private key is kept secret by the user and the public key may be widely distributed. Generally, if user Bob shall send a message to user Alice, Bob will contact Alice and ask for her public key. Alice sends Bob her public key, and Bob uses it to encrypt his message. Bob will then send Alice the message, encrypted with Alice's public key, and the only way to decrypt the message is to use Alice's private key. Børthus, B and Tomas, E. (2005), "Public Key Infrastructure for Windows Server 2003".

Some examples of public key techniques are: Diffie-Hellmann, DSS, ElGamal, RSA, and various Elliptic Curve techniques. Wikipedia.org "Public Key Infrastructure" (May 26, 2006).

A CA is responsible for establishing and vouching for the identity of certificate holders. A CA also revokes certificates if they are no longer valid and publishes certificate revocation lists (CRLs) to be used by certification verifiers. The certificates are issued by a CA based on information provided in the certification request and settings contained in a certification template. A certification template is the set of rules and settings that are applied against incoming certificate requests. The most common digital certificates in PKI use the X.509 Digital Certificate format and usually contain the following: The user's public key; The user's identity, such as name and e-mail address; The validity period of the certificate; The digital signature of the issuer, which attest to the validity of the binding between the user's public key and the user's identifier information. There are different levels of certificates based on the need for functions. As a general rule, the higher level of the certificate, the stricter are the policies for verifying. PKI supports hashing to keep the integrity of the data.

Smart cards are pocket sized plastic cards with embedded integrated circuits. There are 2 broad categories of cards; memory cards and microprocessor cards. The standardization of smart card systems is an ongoing process. One of the standards most referred to is the ISO-7816 standard. A memory card contains non-volatile memory that can store information and perhaps some specific non-programmable security logic. An example of a memory card is a prepaid phone card. They can also be used as a high security alternative to magnetic stripe cards. Memory cards can only perform fixed operations. Microprocessor cards contain memory and microprocessor components. These cards can process data on the card and can used for a variety of applications. Microprocessor cards can provide secure access to networks, be used as SIM card in mobile phones and as electronic wallets. Smart cards are engineered to be tamper resistant and are very suitable to hold personal digital signatures that can be used as authentication to grant access to secure networks. Hong Kong University of Science & Technology (1998) "Guide to Smart Card Technology".

The definition of VPN is "A virtual private network (VPN) is a private data network that makes use of the public telecommunication infrastructure, maintaining privacy through the use of a tunneling protocol and security procedures". VPN Consortium (2006) "VPN Technologies: Definitions and Requirements" www.vpnc.org/vpn-technologies.html. A VPN makes it possible to share resources in a secure way over an insecure public network like the Internet. There are 3 important VPN technologies used: secure, trusted and hybrid VPN. Only secure VPN is relevant to our scenario. Secure VPN uses an encrypted secure "tunnel" to transport data over a public network. Tunneling is generally done by encapsulating the private network data and protocol information within the public network transmission units so that the private network protocol information appears to the public network as data. Tunneling allows the use of the Internet, to convey data on behalf of a private network in a secure way. There are several secure VPN protocols, like IPsec, SSL and PPTP. A properly chosen, implemented, and used secure VPN protocol can provide secure communications over unsecured networks, and provide protection of confidentiality and integrity, and sender authentication to ensure privacy.

Secure authentication is very important when using a VPN solution. Authentication mechanisms can make use of what you know (pin code, password), what you have (smart card) or what you are (fingerprint, retinal scan). Wikipedia.org "Virtual private network" en.wikipedia.org/wiki/Virtual_Private_Network (May 25, 2006). The use of one of the above will give weak authentication, but the use of two will give a much stronger authentication.

DESCRIPTION OF THE INVENTION

Figure 1:
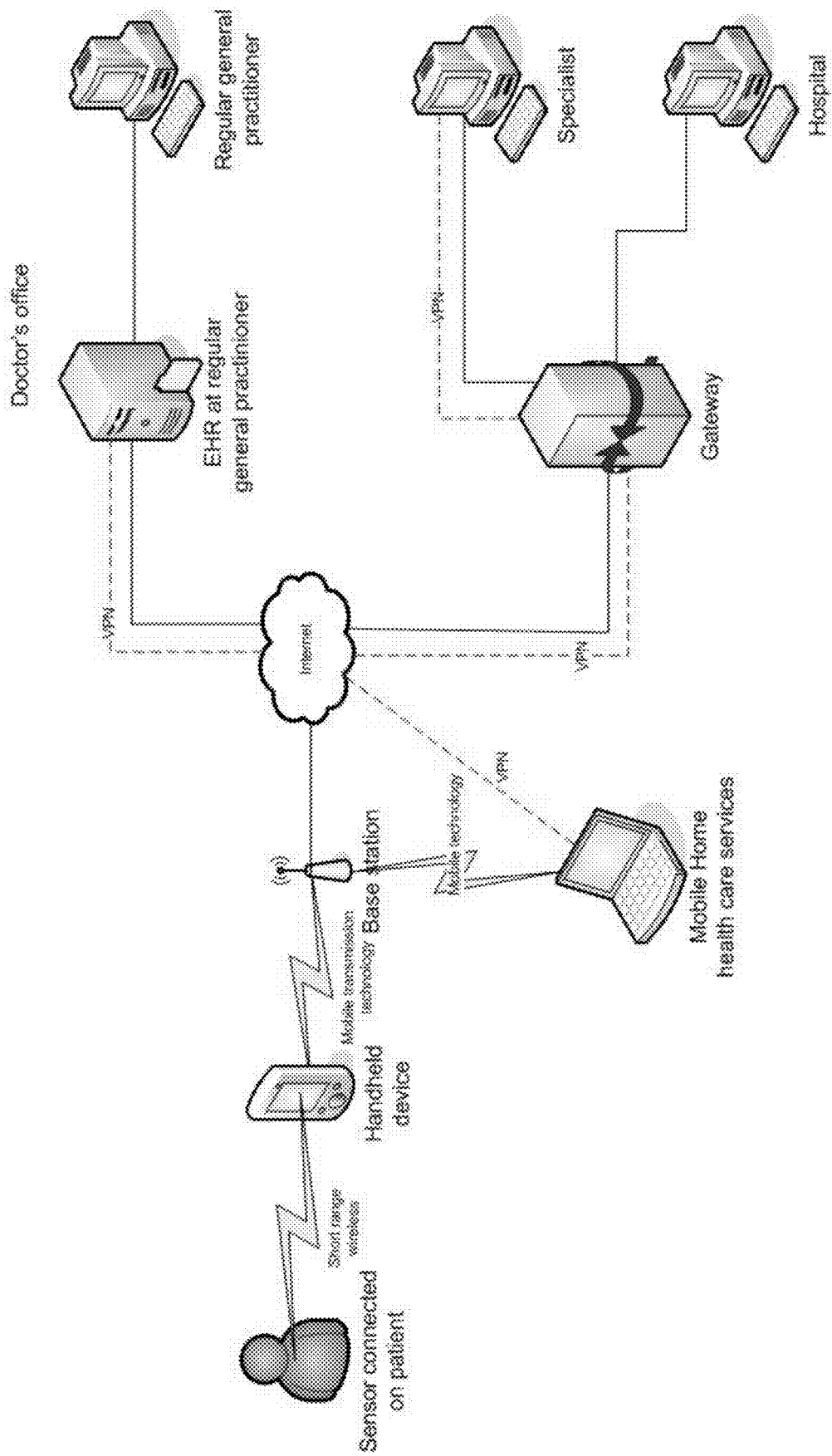
FIG. 1 shows a prior art system architecture.
Figure 2:
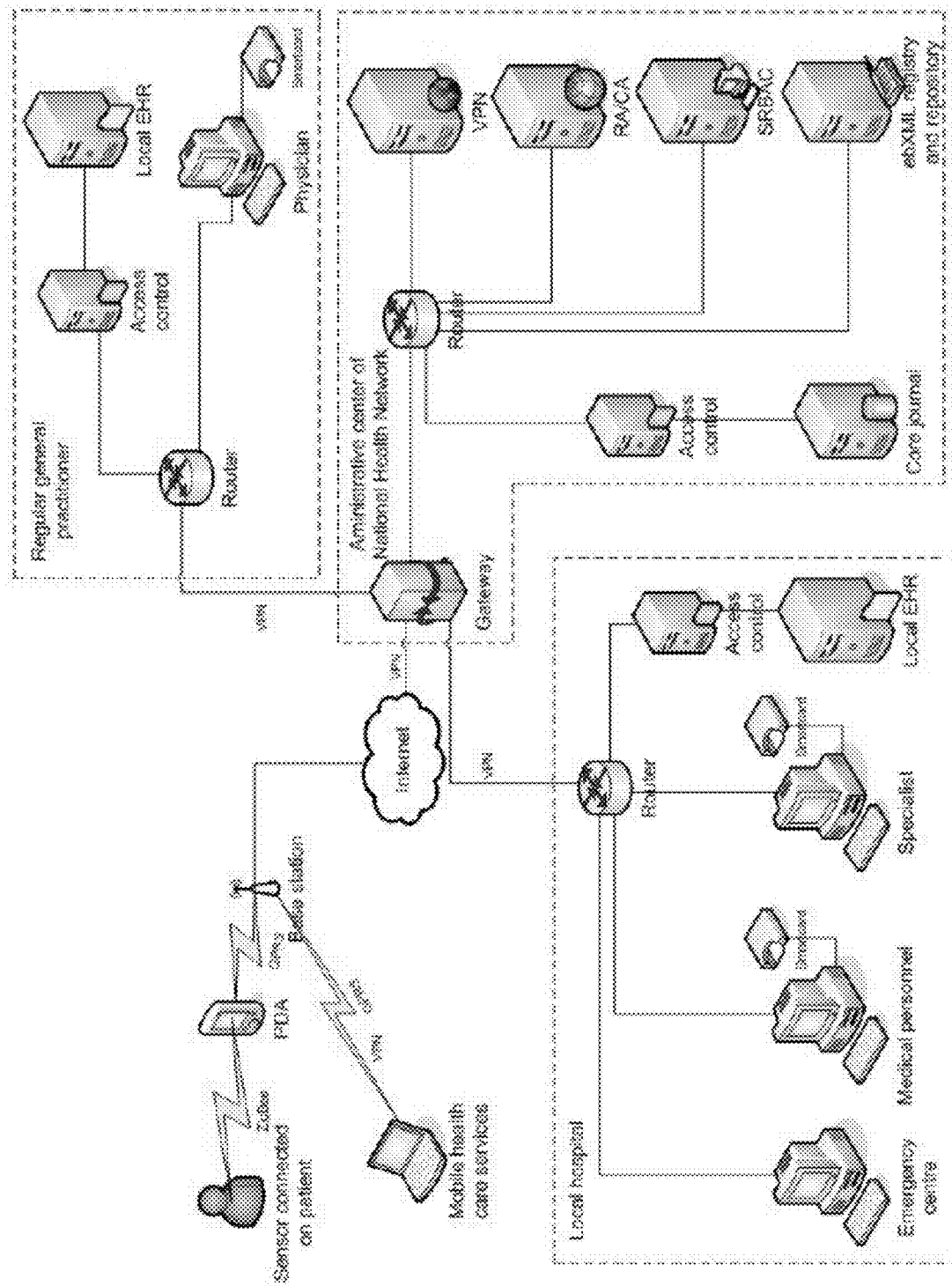
FIG. 2 shows a prior art network architecture.

The preset invention provides a medical device, which may be an implantable device, having a low power communication transceiver with limited communication range. The medical device includes its own processor configured to establish and communicate through an encrypted secure channel which tunnels over a network connection. For example, a virtual private network (VPN) is provided. This VPN then communicates with a predetermined endpoint through potentially insecure public channels and infrastructure.

The technology provides, for example, an implantable medical device, comprising: a self-contained power source (e.g., a battery, supercapacitor, fuel cell, nuclear cell, energy harvesting system, etc.); at least one programmable automated electronic processor; a wireless radio frequency digital communication radio transceiver; a digital memory; and a physiological interface adapted to at least one of receive a physiological signal, produce a physiological stimulation, produce a motion or displacement, infuse a drug, and acquire a biological sample, wherein the at least one programmable automated electronic processor is configured to communicate using a potentially insecure channel with a relay device, and through the relay device establish a secure communication tunnel to a plurality of different endpoints on a public network, and being configured to respond to a request for opening a communication channel with a respective endpoint based on a received message, the plurality of different endpoints each being associated with a respective security certificate to implement a private key infrastructure, the at least one programmable automated electronic processor being configured to verify a the respective security certificate against a certificate revocation list prior to transmitting private data or accepting receiving data as valid.

Electronic medical device may include cardiac monitors, pacemakers, defibrillators, neurological stimulators, pain control devices, artificial or assistive sensory technologies (hearing aids, optic stimulators to restore vision, etc.), insulin and other drug infusion pumps, bladder control stimulators, etc.

In one embodiment, the medical device supports an IEEE-802.11x protocol; however, these tend to be power consuming, and often have communication bandwidth and capabilities not required for a medical device. The medical device may have a strictly limited power budget, making such communications imprudent. However, in certain circumstances, an 802.11b or 802.11g communications might be appropriate. Further, in some configurations, external power might be available during communications.

In another embodiment, a Bluetooth protocol, IEEE 802.15.1 is employed. Bluetooth employs a 2.4 GHz band (2400-2480 MHz).in a frequency hopping spread spectrum protocol having 79 channels each with a bandwidth of 1 MHz. The protocol uses Gaussian frequency-shift keying (GFSK) modulation (Bluetooth 1.0), $\pi$/4-DQPSK and 8DPSK (Bluetooth 2.0+EDR) modulation supporting 1, 2 or 3-Mbits/sec communications. While Bluetooth communications employ security, this typically is only between paired communication partners or small subnets.

Other protocols may be employed; however, it is important that the protocol comprise error detection and correction, tunneling encryption, and low power. Because implantable medical electronics may endure for many years, it may be important that the endpoint of the tunneling encryption be updatable in a secure manner.

Therefore, each implantable medical device has its own digital certificate, and only through a key exchange process will the device open a communications channel. Typically, VPN's are locked to particular endpoints. However, this potentially limits availability of access to the device in emergencies, and permits a central point of failure. Meanwhile, providing a special "administrative access" mode which bypasses the VPN with a lower security level effectively reduces the net security of the device to that lower level plus any vulnerabilities in the VPN implementation.

While there are advantages in having a fully standards-based IP-SEC VPN mode of operation, the purpose of the encrypted communication is to provide privacy and security, and any vulnerability leads to a reduction in these.

In an emergency, such as a central point of failure, bankruptcy or government action to interrupt services, IP filtering, or the like, it is desirable to provide a secure and private mode of access to the device which permits both downloading of information from the device and uploading operational parameters and commands to the device. An implantable medical device typically has only a rudimentary local user interface, which may be a magnetic field, mechanical pressure, or other physical effect, but preferably there is no required local user interface at all; that is a physician or other trained and authorized medical service provided can remotely access the device, receive data from the device, and upload data to the device, without required user intervention at the device.

As discussed above, a smartphone or other internet or network-connected device serves as a relay. According to one premise, these relay devices are not themselves medical devices, and may include vulnerabilities and therefore should not be presumed secure in all aspects. For example, requiring the user to input a personal identification number (PIN) or password through a smartphone to authorize access to the device might lead to release of the PIN or password by a keystroke logger or other malicious software on the phone, or if the phone must further communicate the PIN or password, it could be intercepted in transmission. It is possible for the device to authenticate the relay device based on an authentication protocol, independent of the formation of the VPN channel to a remote endpoint, but some relay infrastructure, such as wireless access points, do not support customized apps or such authentication, and indeed, these may be in fact truly insecure and security-compromised.

Therefore, the device operates by periodically polling its environment for available communications relays, and may in fact operate in a multiprotocol manner. If it finds a suitable partner, it then selects a "best" partner (or may indeed select multiple partners), and establishes a communication link. Typically, the device will seek to establish the lowest power consumption reliable link available. Various ad hoc networking technologies may be employed to balance link reliability and power consumption.

After a link is established, the device then communicates through the link, which acts as a router, to an Internet connected resource or other resource available through the link. In order to ensure compatibility, preferably IPv4 and/or IPv6 communications protocols are employed, generally with TCP. The device seeks to communicate with a registration server or distributed registration server, in which the device authenticates the server, and the server identifies and authenticates the device. Once the handshake authentication, which may employ a Kerberos-type cryptographic protocol, is complete, a message stored in the server is processed by the server, and/or is communicated to the device, representing a request for communication. That is, for example, a service provider may have a pending request to download a data file from the device. That request identifies the service provider and other parameters of the request. The device then seeks to form a communication channel, through the link, with the identified service provider based on the identification. A token may be communicated from the registration server to the device, which is then used as part of a protocol to establish the communication channel; however, it is preferred that the mutual authentication of the device and the service provider be conducted directly through these two communication partners. The device seeks to authenticate the service provider to ensure privacy of the communication, etc. The service provider, however, seeks to authenticate the device in order to avoid uploading malicious data that may incur costs and/or lead to changes in functioning of the device that is party to the communication, or another device that is being spoofed.

Once the device and service provider establish a communication link, which will generally be encrypted and secure, e.g., a VPN, communications, up to and including a full exchange of information, may be conducted, depending on various security rules and administrative limits. A certificate exchange protocol is provided to mutually authenticate the device and service provider. The device stores a set of certificates for a set of authorized communications partners. An emergency override is provided only upon physical access to the device, such as by activating a magnetic reed switch, or generating a unique pseudo-physiological signal that can be recognized by an internal controller.

The authorized communications partners may be, for example, the manufacturer (which itself may serve as a root certificate authority), the patient's physician, the patient's hospital, an on-line service which maintains the device, etc. In some cases, multiple authorized communications partners may be required to concur on a change to be made to the device operational parameters. This serves to limit mistakes, and also control system security.

For example, an implantable pacemaker-defibrillator device maintains an EKG record for the patient for an extended duration, e.g., 1 month, as well as various events and determinations. After some period of time, for example 3 weeks, the device seeks to download its archive to free storage space and permit medical monitoring. The implantable device therefore enters a mode where it seeks suitable communications relays, and may produce a signal perceptible by the patient for the patient to make a relay available. The device uses a Bluetooth protocol to find a Bluetooth compatible device configured to accept the relay communication. For example, the user has a smartphone that has an application installed that listens for the device communications (or proactively communicate with the device). If the device fails to find a compatible device, over an acceptable period of time, it may shift to a different protocol, for example Zigbee or 802.11b/g/n. An 802.11n protocol requires a higher power mode of operation, but may permit communications over a shorter duration. After finding a suitable relay, the device handshakes to establish a link, but does not necessarily require a secure or reliable link. The device then uses the relay to commence negotiation of a virtual private network with at least one of its predetermined endpoints. The link is established based on both an address of the endpoint (i.e., IPv4 or IPv6 address), and secret information which acts as a cryptographic key, wherein the secret itself is not communicated between the partners. The authentication is mutual.

In some cases, after an analysis of the data, a medical professional or automated device may determine that the parameters of operation of the device require updating. In that case, both the treating physician/cardiologist and manufacture (or authorized service provider) may be required to concur on the proposed changes. Typically, the dual authorization is ensured by the device, and the authorization does not rely on one party to offer proof of authorization by the other. Therefore, the device uploads the proposed changes to the parameters, and then communicates with the other authorizing party the proposed changes. This dual communication paradigm may incur higher energy consumption or inconvenience, but limits the risk of collusion or breach of security.

Once the parameters are updated and dual-authorized, the device may then adopt and use the new parameters.

In some cases, it is the certificates maintained in the device that require updating. In that case, the device typically uses a public key infrastructure key hierarchy management system, to manage key importing, expiration, revocation, and use.

Since the relay device, e.g., smartphone is generally near to the patient, in some cases, there is significant incentive to trust that device and therefore increase communications and power efficiency. One way to achieve trusted operation is for the smartphone to enter a mode where the existence of malware or unpatched vulnerabilities are detectable, and therefore that in an absence of either, the local processor can be permitted access to private information and/or control over sensitive parameters. For example, the execution of a program by the smartphone can be checkpointed and compared against a set of known-good checkpoints for the same code, or the code interspersed with "generic" sequences that are also executed remotely on a reference platform, and the results compared. In this case, the results to be analyzed are not necessarily the regular output of the program, but memory pages, executing timing, and other indicia of the nature of the software environment. If unauthorized software is concurrently executing, its presence will be made known by changes in timing of execution, content or hash signatures of memory pages, etc.

The present technology seeks to exploit the known state of the art in virtual private networks. The following references are therefore cited and expressly incorporated by reference in their entirety:

Pulkkis, Göran, et al. "Security of Symbian Based Mobile Devices." Advances in Enterprise Information Technology Security (2007): 31.

Koponen, Pekka, et al. "Interfaces of consumption metering infrastructures with the energy consumers." VTT Research Notes 2542 (2010).

Ross, David Andrew. "Securing IEEE 802.11 wireless LANs." (2010). Ph.D. Thesis Queensland University (2010).

Fischer, Martin. "Enhancing the ReMoteCare prototype by adding an SNMP proxy and video surveillance." (2008). University of Techn., Sydney.

Pankakoski, Veikko. "Experimental design for a next generation residential gateway." (2010). M.S. Thesis Aalto University (2010).

5246008; 6292659; 6643650; 6700535; 6721542; 6744753; 6772331; 6789077; 6789126; 6792466; 6810363; 6813501; 6845097; 6850979; 6862594; 6868447; 6879574; 6885388; 6886095; 6898445; 6898618; 6908391; 6912657; 6916247; 6917976; 6918084; 6922725; 6925562; 6945870; 6947995; 6948066; 6950875; 6950946; 6961541; 6965868; 6968453; 6970869; 6973493; 6975205; 6980660; 6990444; 7010573; 7016966; 7028184; 7031945; 7042988; 7065574; 7065579; 7072967; 7080078; 7082200; 7084736; 7089089; 7089298; 7096137; 7103313; 7110372; 7116661; 7120667; 7121639; 7136927; 7146307; 7152942; 7155518; 7162454; 7165107; 7165824; 7167892; 7167920; 7171323; 7181572; 7181614; 7185199; 7188251; 7188282; 7197565; 7200848; 7203665; 7203753; 7206841; 7206934; 7213047; 7215775; 7216109; 7216231; 7216365; 7222187; 7243356; 7249182; 7251331; 7254608; 7260538; 7260543; 7262709; 7263560; 7263612; 7275102; 7275156; 7278034; 7278697; 7280975; 7283803; 7290132; 7293047; 7295119; 7297062; 7299007; 7302592; 7308496; 7312721; 7318049; 7318086; 7328243; 7339914; 7340214; 7340438; 7340500; 7340770; 7343350; 7346167; 7348895; 7356329; 7366901; 7370091; 7377608; 7379891; 7379913; 7383433; 7386517; 7392375; 7392387; 7395333; 7395536; 7398533; 7399043; 7401152; 7401153; 7409434; 7409569; 7412518; 7415424; 7415439; 7415537; 7418593; 7420956; 7421411; 7424285; 7426271; 7426721; 7433649; 7433773; 7444644; 7454542; 7454619; 7458082; 7461172; 7475244; 7477873; 7484225; 7487509; 7500104; 7509387; 7512649; 7516325; 7522549; 7523111; 7529713; 7533141; 7533161; 7533172; 7536177; 7536723; 7545941; 7546254; 7548946; 7549056; 7562028; 7562051; 7565328; 7565529; 7570943; 7571346; 7573855; 7574523; 7577575; 7577619; 7577620; 7577834; 7581096; 7584360; 7587196; 7590589; 7592829; 7596227; 7597250; 7599305; 7600252; 7606242; 7606570; 7607012; 7613881; 7617159; 7624143; 7630941; 7634230; 7649872; 7657255; 7657597; 7660990; 7660998; 7672662; 7680133; 7684374; 7689508; 7697894; 7698393; 7701912; 7702821; 7703073; 7707415; 7707621; 7708194; 7712111; 7712777; 7715351; 7716492; 7724717; 7730482; 7733804; 7743074; 7747980; 7748618; 7757076; 7760654; 7761863; 7761885; 7761910; 7762470; 7770008; 7774495; 7778927; 7783041; 7783777; 7783886; 7787865; 7788663; 7801058; 7801781; 7804807; 7818519; 7818811; 7822863; 7823772; 7831238; 7831752; 7831827; 7844834; 7848746; 7849140; 7853255; 7853780; 7860922; 7860923; 7864673; 7869601; 7870097; 7881667; 7886962; 7899187; 7899915; 7904074; 7907935; 7916861; 7920518; 7920534; 7920851; 7937089; 7944577; 7945959; 7950047; 7953818; 7962164; 7970894; 7974234; 7974296; 7975002; 7975051; 7978062; 7979692; 7983615; 7983835; 7986704; 7987491; 7990947; 7991764; 8000314; 8001232; 8005476; 8009608; 8013732; 8014722; 8019352; 8023425; 8028329; 8031650; 8032939; 8036195; 8037202; 8038239; 8046328; 8046504; 8050405; 8064412; 8064879; 8064926; 8068831; 8073839; 8082491; 8090399; 8103691; 8103718; 8108455; 8116734; 8117547; 8127039; 8130146; 8131645; 8135796; 8136149; 8139588; 8144725; 8145219; 8149848; 8150312; 8150372; 8150416; 8151336; 8156337; 8159985; 8160077; 8161172; 8165142; 8166296; 8166551; 8171136; 8171292; 8175528; 8179911; 8182340; 8185119; 8193930; 8195233; 8195934; 8200195; 8200700; 8204522; 8204992; 8212667; 8213907; 8214228; 8214645; 8223010; 8224893; 8225094; 8225380; 8226474; 8228861; 8229785; 8229812; 8229813; 8229888; 8233471; 8234387; 8245315; 8249028; 8249559; 8250207; 8250628; 8260274; 8260320; 8261338; 8266212; 8266438; 8266676; 8270310; 8270952; 8271800; 8271802; 8275395; 8275672; 8279067; 8280359; 8281169; 8284748; 8289886; 8290498; 8296825; 8301784; 8302167; 8305935; 8305936; 8305980; 8311214; 8311939; 8316091; 8316438; 8320879; 8321330; 8321526; 8321534; 8322607; 8326958; 8327131; 8331901; 8335222; 8335304; 8341141; 8341291; 8341292; 8345881; 8346248; 8347088; 8347093; 8351898; 8352342; 8352636;

8353052; 8355337; 8359016; 8359397; 8364961; 8369830; 8370236; 8373556; 8375202; 8379564; 8380982; 8381262; 8385240; 8385916; 8386394; 8392289; 8395498; 8396458; RE42725; RE42871; 20020069278; 20020072975; 20020075844; 20020133534; 20020143655; 20020143855; 20020143944; 20020147771; 20020147810; 20020152299; 20020161476; 20020184310; 20020184311; 20020184357; 20020184358; 20020188657; 20030002521; 20030041141; 20030065525; 20030087629; 20030093691; 20030100369; 20030100370; 20030100371; 20030100372; 20030229900; 20040019807; 20040030743; 20040030794; 20040031038; 20040031058; 20040044727; 20040064512; 20040064568; 20040064693; 20040073795; 20040088347; 20040088348; 20040088369; 20040088646; 20040098447; 20040133640; 20040148326; 20040162871; 20040198220; 20050086300; 20050109841; 20050129240; 20050141706; 20050144437; 20050233811; 20050259611; 20050261970; 20050273850; 20060002331; 20060010251; 20060010485; 20060040248; 20060041445; 20060041446; 20060041460; 20060041891; 20060062206; 20060092043; 20060095199; 20060156054; 20060167784; 20060174017; 20060208066; 20060219776; 20060234678; 20060282662; 20060291455; 20070004436; 20070022474; 20070022479; 20070025245; 20070025265; 20070060099; 20070060109; 20070060114; 20070060129; 20070060136; 20070060173; 20070061197; 20070061198; 20070061211; 20070061229; 20070061242; 20070061243; 20070061244; 20070061245; 20070061246; 20070061247; 20070061300; 20070061301; 20070061302; 20070061303; 20070061317; 20070061328; 20070061331; 20070061332; 20070061333; 20070061334; 20070061335; 20070061336; 20070061363; 20070073717; 20070073718; 20070073719; 20070073722; 20070073723; 20070087756; 20070094042; 20070097885; 20070100650; 20070100651; 20070100652; 20070100653; 20070100806; 20070118533; 20070136817; 20070143629; 20070143827; 20070143851; 20070156895; 20070168354; 20070169184; 20070171885; 20070192294; 20070192318; 20070198432; 20070198485; 20070239724; 20070260635; 20070263783; 20070288427; 20070293323; 20080009268; 20080032801; 20080033869; 20080041937; 20080052769; 20080063201; 20080076572; 20080092181; 20080095180; 20080097858; 20080098212; 20080109879; 20080141360; 20080167954; 20080183853; 20080222715; 20080229402; 20080234047; 20080242279; 20080252485; 20080256618; 20090013380; 20090016529; 20090036111; 20090046591; 20090046598; 20090046644; 20090046676; 20090046861; 20090047930; 20090047966; 20090049158; 20090060201; 20090073943; 20090088133; 20090119741; 20090119776; 20090168990; 20090199009; 20090204805; 20090204964; 20090254572; 20090254646; 20090275403; 20090281872; 20090319672; 20090320073; 20090322510; 20090327729; 20100057801; 20100076845; 20100082430; 20100082431; 20100094981; 20100095077; 20100099396; 20100100930; 20100115606; 20100121705; 20100131618; 20100131619; 20100131622; 20100131652; 20100132040; 20100138293; 20100138296; 20100138908; 20100138926; 20100142410; 20100145804; 20100146146; 20100150170; 20100153208; 20100153211; 20100169179; 20100186078; 20100188975; 20100188990; 20100188991; 20100188992; 20100188993; 20100188994; 20100188995; 20100190470; 20100191575; 20100191576; 20100191604; 20100191612; 20100191613; 20100191846; 20100191847; 20100192120; 20100192170; 20100192207; 20100192212; 20100192220; 20100197266; 20100197268; 20100198681; 20100211458; 20100211645; 20100217662; 20100217663; 20100235285; 20100235879; 20100250497; 20100269146; 20100275250; 20100281364; 20100293051; 20100293221; 20100299522; 20100299763; 20100304737; 20100317420; 20110004513; 20110015993; 20110015994; 20110019627; 20110029378; 20110029387; 20110047062; 20110106614; 20110145076; 20110159902; 20110167474; 20110194698; 20110202874; 20110216674; 20110217966; 20110219234; 20110219419; 20110230268; 20110231936; 20110246766; 20110258046; 20110273568; 20110275393; 20110276673; 20110277028; 20110289308; 20110289314; 20110302408; 20110307710; 20110312310; 20110313862; 20110320264; 20110320265; 20110320266; 20110320267; 20110320268; 20110320269; 20110320270; 20110320271; 20110320279; 20110320280; 20110320281; 20110320282; 20110321127; 20120004984; 20120004985; 20120004986; 20120004987; 20120004988; 20120004989; 20120004990; 20120004991; 20120004992; 20120004993; 20120004994; 20120004995; 20120004996; 20120004997; 20120004998; 20120004999; 20120005000; 20120005001; 20120005002; 20120005003; 20120005004; 20120005005; 20120005006; 20120005007; 20120005008; 20120005009; 20120005010; 20120005011; 20120005012; 20120005013; 20120005014; 20120005020; 20120005077; 20120005078; 20120005079; 20120005080; 20120005081; 20120005082; 20120005083; 20120005084; 20120005085; 20120005086; 20120005087; 20120005088; 20120005089; 20120005090; 20120005091; 20120005092; 20120005725; 20120005726; 20120010945; 20120010946; 20120010947; 20120010948; 20120010949; 20120010950; 20120010951; 20120010952; 20120010953; 20120010954; 20120010955; 20120010956; 20120010957; 20120010958; 20120010959; 20120010960; 20120010961; 20120010962; 20120010963; 20120010964; 20120010965; 20120010966; 20120010967; 20120010968; 20120010969; 20120010970; 20120010971; 20120010972; 20120010973; 20120010974; 20120010975; 20120010976; 20120010977; 20120010978; 20120010979; 20120011058; 20120015644; 20120016925; 20120027001; 20120030470; 20120032945; 20120036010;

20120036220; 20120036245; 20120036440; 20120036442; 20120036552; 20120041819; 20120054848; 20120059711; 20120059718; 20120066057; 20120066065; 20120066198; 20120066199; 20120069131; 20120084544; 20120084545; 20120084562; 20120084566; 20120084838; 20120086345; 20120087319; 20120088470; 20120089699; 20120089845; 20120094769; 20120096513; 20120101831; 20120101832; 20120101833; 20120101834; 20120101835; 20120101836; 20120102143; 20120105199; 20120105201; 20120105214; 20120109667; 20120109668; 20120109669; 20120109670; 20120109671; 20120109672; 20120109673; 20120109674; 20120109851; 20120110602; 20120116790; 20120116959; 20120118947; 20120122528; 20120122529; 20120122558; 20120129503; 20120130811; 20120130812; 20120131685; 20120134291; 20120150629; 20120158607; 20120159438; 20120159578; 20120185390; 20120190386; 20120191860; 20120192249; 20120195206; 20120195222; 20120195223; 20120196565; 20120197709; 20120197724; 20120197792; 20120201133; 20120203677; 20120204245; 20120208496; 20120209750; 20120210130; 20120210391; 20120210401; 20120214441; 20120215831; 20120216225; 20120222123; 20120232945; 20120232970; 20120238255; 20120240183; 20120240196; 20120240236; 20120254474; 20120259981; 20120284416; 20120294195; 20120297464; 20120323717; 20120323786; 20120324067; 20120324242; 20120324562; 20120330829; 20130003613; 20130005299; 20130005322; 20130006729; 20130006780; 20130007837; 20130010945; 20130012178; 20130014263; 20130016636; 20130024254; 20130024257; 20130024262; 20130024267; 20130024364; 20130024371; 20130034230; 20130040703; 20130045710; 20130054820; 20130054962; 20130055315; 20130055347; 20130061264; 20130061273; 20130065551; 20130066723; 20130067023; and 20130067526.

If several different applications or data need to be secured between the devices, it often makes sense to apply a suitable VPN (Virtual Private Network) technology. VPN can protect the data communication interfaces from malicious attacks by dropping all inadequate data traffic, and also provides the secure tunneling for insecure protocols and data to traverse securely over various networks. A useful information and comparison of various VPN protocols is available e.g. in NIST SP 800-77 "Guide to IPSec VPNs", Chapter 5.

Transport Layer Security (TLS)—IETF RFC5246 can cryptographically protect the information that the OSI transport layer 4 delivers. It can provide adequate security with: Payload data authentication, integrity verification and encryption; Replay protection; and Public key certificate based mutual authentication of the peers. The strength of the algorithms and key lengths are negotiated in the beginning of a secure TLS session, using a special handshake protocol. The handshakes can utilize public key certificates and cryptography (e.g. DSS, RSA) also for mutual authentication (server+client certificates), when necessary. The cryptographic key and policy negotiation messaging is rather well secured in TLS specification and most implementations. Also, the strength of the strongest user data "Cipher-Suites" are very good (AES, 3DES, etc. are supported with long keys). Also, the Datagram Transport Layer Security (DTLS)—IETF RFC4347 is a protocol that travels within the transport layer PDU. So, both TLS and DTLS can traverse NATs and provide easy and secure device data exchanges without securing the transport layer or lower layers. This allows for example any client/server applications to communicate in straightforward way. DTLS over the Datagram Congestion Control Protocol (DCCP)—IETF RFC5238 is also one possible protocol to be considered.

Security Architecture for the Internet Protocol—IPSec (IETF RFC4301-4309) is a family of protocols (of which AH and ESP are implemented at TCP/IP stack's network layer, or at least under transport layer). IPSec can provide adequate security in flexible ways using: IP header and payload data authentication, integrity verification and encryption (only ESP); Replay protection; and Public key certificate or shared secrets based mutual authentication of the peers. The IPsec architecture consists of a number of specifications: Security Architecture for the Internet Protocol (IETF RFC4301); IP Authentication Header (AH) (IETF RFC4302); IP Encapsulating Security Payload (ESP) (IETF RFC4303); Internet Key Exchange (IKEv2) Protocol (IETF RFC4306); Cryptographic Algorithms for Use in the Internet Key Exchange Version 2 (IKEv2) (IETF RFC4307); Cryptographic Suites for IPsec (IETF RFC4308); Using Advanced Encryption Standard (AES) CCM Mode with IPsec Encapsulating Security Payload (ESP) (IETF RFC4309); Cryptographic Algorithm Implementation Requirements for ESP and AH (IETF RFC4835). The tunnel mode ESP (and IKE) are used in the construction of IPSec based Virtual Private Networks (VPNs). However, IKE is a rather resource consuming protocol for secure connection establishment with its complex ISAKMP message exchanges, but it is a scalable way to establish the secure connections between different parties of the infrastructure.

An alternative approach is to utilize even stronger, lower-layer security protocol to provide the security services for SNMP. For example, RFC5590 defines an extension which allows an "external" security protocol to be used with SNMP engines. Potential external protocols include TLS and SSH (RFC4251).

A transport layer Stream Control Transmission Protocol (SCTP)—IETF RFC4960 is quite a recent, reliable protocol providing for independent message streams: May use TLS/SSL or run over IPsec; Congestion avoidance behavior; Protection against flooding attacks (lightweight mutual authentication). Delivery mechanisms include: Sequential non-duplicated delivery of messages for each independent stream and Immediate delivery (bypassing the sequential delivery).

The Secure Real-time Transport Protocol (SRTP)—IETF RFC3711 defines a RTP (Real-time Transport Protocol) profile which provides for unicast and multicast RTP data security to be used as a stream cipher: Segmented Integer Counter Mode: AES with 128-bit key as default; f8-mode: AES with 128-bit key as default; Authentication, integrity and replay protection: HMAC-SHA1 as truncated to 80 or 32-bits size; Hashing over the payload and the header including sequence number. There are several possible choices that can be used for the negotiation and derivation of cryptographic keys that SRTP will need. Alternatives include: MIKEY (RFC3830: Multimedia Internet KEYing); SDES (RFC4568: Session Description Protocol (SDP) Security Descriptions for Media Streams); ZRTP (IETF Draft: Media Path Key Agreement for Secure RTP).

Bluetooth provides a secure way to connect and exchange information between devices such as faxes, mobile phones, telephones, laptops, personal computers, printers, Global Positioning System (GPS) receivers, digital cameras, and video game consoles. It was principally designed as a low-bandwidth technology.

A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone will necessarily begin as master, as initiator of the connection; but may subsequently prefer to be slave).

The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode). The master chooses which slave device to address; typically, it switches rapidly from one device to another in a round-robin fashion. Since it is the master that chooses which slave to address, whereas a slave is (in theory) supposed to listen in each receive slot, being a master is a lighter burden than being a slave. Being a master of seven slaves is possible; being a slave of more than one master is difficult. The specification is vague as to required behavior in scatternets.

The effective range varies due to propagation conditions, material coverage, production sample variations, antenna configurations and battery conditions. In most cases the effective range of Class 2 devices is extended if they connect to a Class 1 transceiver, compared to a pure Class 2 network. This is accomplished by the higher sensitivity and transmission power of Class 1 devices.

To use Bluetooth wireless technology, a device has to be able to interpret certain Bluetooth profiles, which are definitions of possible applications and specify general behaviors that Bluetooth enabled devices use to communicate with other Bluetooth devices. These profiles include settings to parametrize and to control the communication from start. Adherence to profiles saves the time for transmitting the parameters anew before the bi-directional link becomes effective. There are a wide range of Bluetooth profiles that describe many different types of applications or use cases for devices.

Bluetooth and Wi-Fi (the brand name for products using IEEE 802.11 standards) have some similar applications: setting up networks, printing, or transferring files. Wi-Fi is intended as a replacement for cabling for general local area network access in work areas. This category of applications is sometimes called wireless local area networks (WLAN). Bluetooth was intended for portable equipment and its applications. The category of applications is outlined as the wireless personal area network (WPAN). Bluetooth is a replacement for cabling in a variety of personally carried applications in any setting and also works for fixed location applications such as smart energy functionality in the home (thermostats, etc.).

Wi-Fi is a wireless version of a common wired Ethernet network, and requires configuration to set up shared resources, transmit files, and to set up audio links (for example, headsets and hands-free devices). Wi-Fi uses the same radio frequencies as Bluetooth, but with higher power, resulting in higher bit rates and better range from the base station. The nearest equivalents in Bluetooth are the DUN profile, which allows devices to act as modem interfaces, and the PAN profile, which allows for ad-hoc networking. Bluetooth v2.1+EDR has a data rate of about 3 Mbit/s, although the practical data transfer rate is 2.1 Mbit/s. EDR uses a combination of GFSK and Phase Shift Keying modulation (PSK) with two variants, $\pi/4$-DQPSK and 8DPSK. EDR can provide a lower power consumption through a reduced duty cycle. Bluetooth v3.0+HS provides theoretical data transfer speeds of up to 24 Mbit/s, though not over the Bluetooth link itself. Instead, the Bluetooth link is used for negotiation and establishment, and the high data rate traffic is carried over a collocated 802.11 link. The main new feature is AMP (Alternate MAC/PHY), the addition of 802.11 as a high speed transport. Bluetooth Core Specification version 4.0 includes Classic Bluetooth, Bluetooth high speed and Bluetooth low energy protocols. Bluetooth high speed is based on Wi-Fi, and Classic Bluetooth consists of legacy Bluetooth protocols. Bluetooth low energy (BLE), previously known as WiBree, is a subset to Bluetooth v4.0 with an entirely new protocol stack for rapid build-up of simple links. As an alternative to the Bluetooth standard protocols that were introduced in Bluetooth v1.0 to v3.0, it is aimed at very low power applications running off a coin cell. Chip designs allow for two types of implementation, dual-mode, single-mode and enhanced past versions. The provisional names Wibree and Bluetooth ULP (Ultra Low Power) were abandoned and the BLE name was used for a while. In late 2011, new logos "Bluetooth Smart Ready" for hosts and "Bluetooth Smart" for sensors were introduced as the general-public face of BLE. General improvements in version 4.0 include the changes necessary to facilitate BLE modes, as well the Generic Attribute Profile (GATT) and Security Manager (SM) services with AES Encryption.

Many of the services offered over Bluetooth can expose private data or allow the connecting party to control the Bluetooth device. For security reasons it is necessary to be able to recognize specific devices and thus enable control over which devices are allowed to connect to a given Bluetooth device. At the same time, it is useful for Bluetooth devices to be able to establish a connection without user intervention (for example, as soon as they are in range).

To resolve this conflict, Bluetooth uses a process called bonding, and a bond is created through a process called pairing. The pairing process is triggered either by a specific request from a user to create a bond (for example, the user explicitly requests to "Add a Bluetooth device"), or it is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices. When desired, the bonding relationship can later be removed by the user.

During the pairing process, the two devices involved establish a relationship by creating a shared secret known as a link key. If a link key is stored by both devices, they are said to be paired or bonded. A device that wants to communicate only with a bonded device can cryptographically authenticate the identity of the other device, and so be sure that it is the same device it previously paired with. Once a link key has been generated, an authenticated Asynchronous Connection-Less (ACL) link between the devices may be encrypted so that the data that they exchange over the airwaves is protected against eavesdropping. Link keys can be deleted at any time by either device. If done by either device this will implicitly remove the bonding between the devices; so it is possible for one of the devices to have a link key stored but not be aware that it is no longer bonded to the device associated with the given link key. Bluetooth services generally require either encryption or authentication, and as such require pairing before they allow a remote device to use the given service. Some services, such as the Object Push Profile, elect not to explicitly require authentication or encryption so that pairing does not interfere with the user experience associated with the service use-cases. Pairing mechanisms have changed significantly with the introduction of Secure Simple Pairing in Bluetooth v2.1.

Bluetooth implements confidentiality, authentication and key derivation with custom algorithms based on the SAFER+ block cipher. Bluetooth key generation is generally based on a Bluetooth PIN, which must be entered into both devices. This procedure might be modified if one of the devices has a fixed PIN (e.g., for headsets or similar devices with a restricted user interface). During pairing, an initialization key or master key is generated, using the E22 algorithm. The E0 stream cipher is used for encrypting packets, granting confidentiality, and is based on a shared cryptographic secret, namely a previously generated link key or master key. Those keys, used for subsequent encryption of data sent via the air interface, rely on the Bluetooth PIN, which has been entered into one or both devices.

Bluetooth is susceptible to denial-of-service attacks, eavesdropping, man-in-the-middle attacks, message modification, and resource misappropriation. The present technology addresses these security limitations (except for denial-of-service attacks) by providing a security layer which tunnels through the Bluetooth link, and therefore does not rely on the Bluetooth security protocols.

Bluetooth uses the microwave radio frequency spectrum in the 2.402 GHz to 2.480 GHz range. Maximum power output from a Bluetooth radio is 100 mW for class 1, 2.5 mW for class 2, and 1 mW for class 3 devices. Even the maximum power output of class 1 is a lower level than the lowest powered mobile phones.

See:

"Bluetooth.org". Bluetooth.org. www.bluetooth.org/About/bluetooth_sig.htm.

"Bluetooth Radio Interface, Modulation & Channels". Radio-Electronics.com. www.radio-electronics.com/info/wireless/bluetooth/radio-interface-modulation.php.

"How Bluetooth Technology Works". Bluetooth SIG. Archived from the original on 17 Jan. 2008.

"Specification Documents". Bluetooth.com. 30 Jun. 2010. www.bluetooth.com/Specification%20Documents/AssignedNumbersServiceDiscovery.pdf "IEEE Std 802.15.1-2002—IEEE Standard for Information technology—Telecommunications and information exchange between systems—Local and metropolitan area networks—Specific requirements Part 15.1: Wireless Medium Access Control (MAC) and Physical Layer (PHY) Specifications for Wireless Personal Area Networks (WPANs)".
ieeexplore.ieee.org. doi:10.1109/IEEESTD0.2002.93621.
ieeexplore.ieee.org/servlet/opac?punumber=7932.

"IEEE Std 802.15.1-2005—IEEE Standard for Information technology—Telecommunications and information exchange between systems—Local and metropolitan area networks—Specific requirements Part 15.1: Wireless Medium Access Control (MAC) and Physical Layer (PHY) Specifications for Wireless Personal Area Networks (W Pans)".
ieeexplore.ieee.org. doi:10.1109/IEEESTD.2005.96290.
ieeexplore.ieee.org/servlet/opac?punumber=9980.

"Specification Documents". Bluetooth SIG. www.bluetooth.org.

"Bluetooth Core Version 3.0+HS specification". www.bluetooth.org/docman/handlers/DownloadDoc.ashx?doc_id=40560.

"Bluetooth Core Specification Addendum (CSA) 1". www.bluetooth.org/DocMan/handlers/DownloadDoc.ashx?doc_id=119993.

D. Chomienne, M. Eftimakis (20 Oct. 2010). "Bluetooth Tutorial" (PDF). www.newlogic.com/products/Bluetooth-Tutorial-2001.pdf.

Juha T. Vainio (25 May 2000). "Bluetooth Security". Helsinki University of Technology. www.iki.fi/jiitv/bluesec.pdf.

Andreas Becker (16 Aug. 2007) (PDF). Bluetooth Security & Hacks. Ruhr-Universität Bochum. gsyc.es/~anto/ubicuosa2/bluetooth_security_and_hacks.pdf.

Scarfone, K., and Padgette, J. (September 2008) (PDF). Guide to Bluetooth Security. National Institute of Standards and Technology. csrc.nist.gov/publications/nistpubs/800-121/SP800-121.pdf.

"Security Weaknesses in Bluetooth". RSA Security Conf.—Cryptographer's Track. CiteSeerX: 10.1.1.23.7357.

Ford-Long Wong, Frank Stajano, Jolyon Clulow (2005-04) (PDF). Repairing the Bluetooth pairing protocol. University of Cambridge Computer Laboratory. Archived from the original on 16 Jun. 2007. web.archive.org/web/20070616082657/www.cl.cam.ac.uk/~fw242/publications/2005-WongStaClu-bluetooth.pdf.

VPN Connectivity Overview (See Wikipedia)

A virtual private network (VPN) extends a private network and the resources contained in the network across public networks like the Internet. It enables a host computer to send and receive data across shared or public networks as if it were a private network with all the functionality, security and management policies of the private network. This is done by establishing a virtual point-to-point connection through the use of dedicated connections, encryption, or a combination of the two. The VPN connection across the Internet is technically a wide area network (WAN) link between the sites but appears to the user as a private network link—hence the name "virtual private network".

VPNs can be either remote-access (connecting an individual computer to a network) or site-to-site (connecting two networks together). In a corporate setting, remote-access VPNs allow employees to access their company's intranet from home or while traveling outside the office, and site-to-site VPNs allow employees in geographically separated offices to share one cohesive virtual network. A VPN can also be used to interconnect two similar networks over a dissimilar middle network; for example, two IPv6 networks over an IPv4 network.

VPNs typically require remote access to be authenticated and make use of encryption techniques to prevent disclosure of private information. VPNs provide security through tunneling protocols and security procedures such as encryption. Their security model provides: Confidentiality such that even if traffic is sniffed, an attacker would only see encrypted data which they cannot understand; (see Packet analyzer and Deep packet inspection); Allowing Sender authentication to prevent unauthorized users from accessing the VPN; Message integrity to detect any instances of transmitted messages having been tampered with.

Secure VPN protocols include the following:

IPSec (Internet Protocol Security) was developed by the Internet Engineering Task Force (IETF), and was initially developed for IPv6, which requires it. This standards-based security protocol is also widely used with IPv4. Layer 2 Tunneling Protocol frequently runs over IPSec. Its design meets most security goals: authentication, integrity, and confidentiality. IPSec functions through encrypting and encapsulating an IP packet inside an IPSec packet. De-encapsulation happens at the end of the tunnel, where the original IP packet is decrypted and forwarded to its intended destination.

Transport Layer Security (SSL/TLS) can tunnel an entire network's traffic, as it does in the OpenVPN project, or secure an individual connection. A number of vendors provide remote access VPN capabilities through SSL. An SSL VPN can connect from locations where IPsec runs into trouble with Network Address Translation and firewall rules.

Datagram Transport Layer Security (DTLS), is used in Cisco AnyConnect VPN or OpenConnect VPN, to solve the issues SSL/TLS has with tunneling over UDP.

Microsoft Point-to-Point Encryption (MPPE) works with the Point-to-Point Tunneling Protocol and in several compatible implementations on other platforms.

Microsoft's Secure Socket Tunneling Protocol (SSTP), introduced in Windows Server 2008 and in Windows Vista Service Pack 1. SSTP tunnels Point-to-Point Protocol (PPP) or Layer 2 Tunneling Protocol traffic through an SSL 3.0 channel.

MPVPN (Multi Path Virtual Private Network).

Secure Shell (SSH) VPN—OpenSSH offers VPN tunneling (distinct from port forwarding) to secure remote connections to a network or inter-network links. OpenSSH server provides a limited number of concurrent tunnels and the VPN feature itself does not support personal authentication. "ssh(1)—OpenBSD manual pages". man.openbsd.org; c @cb.vu, Colin Barschel. "Unix Toolbox". cb.vu; "SSH_VPN—Community Help Wiki". help.ubuntu.com.

Tunnel endpoints must authenticate before secure VPN tunnels can be established. User-created remote access VPNs may use passwords, biometrics, two-factor authentication or other cryptographic methods. Network-to-network tunnels often use passwords or digital certificates, as they permanently store the key to allow the tunnel to establish automatically and without intervention from the user.

The following steps illustrate the principles of a VPN client-server interaction in simple terms. Assume a remote host with public IP address 1.2.3.4 wishes to connect to a server found inside a company network. The server has internal address 192.168.1.10 and is not reachable publicly. Before the client can reach this server, it needs to go through a VPN server/firewall device that has public IP address 5.6.7.8 and an internal address of 192.168.1.1. All data between the client and the server will need to be kept confidential, hence a secure VPN is used. The VPN client connects to a VPN server via an external network interface. The VPN server assigns an IP address to the VPN client from the VPN server's subnet. The client gets internal IP address 192.168.1.50, for example, and creates a virtual network interface through which it will send encrypted packets to the other tunnel endpoint (the device at the other end of the tunnel). (This interface also gets the address 192.168.1.50.) When the VPN client wishes to communicate with the company server, it prepares a packet addressed to 192.168.1.10, encrypts it and encapsulates it in an outer VPN packet, say an IPSec packet. This packet is then sent to the VPN server at IP address 5.6.7.8 over the public Internet. The inner packet is encrypted so that even if someone intercepts the packet over the Internet, they cannot get any information from it. They can see that the remote host is communicating with a server/firewall, but none of the contents of the communication. The inner encrypted packet has source address 192.168.1.50 and destination address 192.168.1.10. The outer packet has source address 1.2.3.4 and destination address 5.6.7.8. When the packet reaches the VPN server from the Internet, the VPN server decapsulates the inner packet, decrypts it, finds the destination address to be 192.168.1.10, and forwards it to the intended server at 192.168.1.10. After some time, the VPN server receives a reply packet from 192.168.1.10, intended for 192.168.1.50. The VPN server consults its routing table, and sees this packet is intended for a remote host that must go through VPN. The VPN server encrypts this reply packet, encapsulates it in a VPN packet and sends it out over the Internet. The inner encrypted packet has source address 192.168.1.10 and destination address 192.168.1.50. The outer VPN packet has source address 5.6.7.8 and destination address 1.2.3.4. The remote host receives the packet. The VPN client decapsulates the inner packet, decrypts it, and passes it to the appropriate software at upper layers. Overall, it is as if the remote computer and company server are on the same 192.168.1.0/24 network.

Tunneling protocols can operate in a point-to-point network topology that would theoretically not be considered a VPN, because a VPN by definition is expected to support arbitrary and changing sets of network nodes. But since most router implementations support a software-defined tunnel interface, customer-provisioned VPNs often are simply defined tunnels running conventional routing protocols. According to the present technology, support for arbitrary and changing sets of network nodes is preferably, but not mandatorily, provided.

Depending on whether the PPVPN (Provider Provisioned VPN) runs in layer 2 or layer 3, the building blocks described below may be L2 only, L3 only, or combine them both. Multiprotocol label switching (MPLS) functionality blurs the L2-L3 identity. RFC 4026 generalized the following terms to cover L2 and L3 VPNs, but they were introduced in RFC 2547.

Mobile VPNs are used in a setting where an endpoint of the VPN is not fixed to a single IP address, but instead roams across various networks such as data networks from cellular carriers or between multiple Wi-Fi access points. Mobile VPNs have been widely used in public safety, where they give law enforcement officers access to mission-critical applications, such as computer-assisted dispatch and criminal databases, while they travel between different subnets of a mobile network. They are also used in field service management and by healthcare organizations, among other industries. Increasingly, mobile VPNs are being adopted by mobile professionals who need reliable connections. They are used for roaming seamlessly across networks and in and out of wireless-coverage areas without losing application sessions or dropping the secure VPN session. A conventional VPN cannot survive such events because the network tunnel is disrupted, causing applications to disconnect, time out, or fail, or even cause the computing device itself to crash. Instead of logically tying the endpoint of the network tunnel to the physical IP address, each tunnel is bound to a permanently associated IP address at the device. The mobile VPN software handles the necessary network authentication and maintains the network sessions in a manner transparent to the application and the user. The Host Identity Protocol (HIP), under study by the Internet Engineering Task Force, is designed to support mobility of hosts by separating the role of IP addresses for host identification from their locator functionality in an IP network. With HIP a mobile host maintains its logical connections established via the host identity identifier while associating with different IP addresses when roaming between access networks.

OpenBSD ssh manual page, VPN section

Unix Toolbox section on SSH VPN

E. Rosen & Y. Rekhter (March 1999). "RFC 2547 BGP/MPLS VPNs". Internet Engineering Task Forc (IETF). www.ietf.org/rfc/rfc2547.txt.

Secure Shell (SSH) is a cryptographic network protocol for secure data communication, remote shell services or command execution and other secure network services between two networked computers that connects, via a secure channel over an insecure network, a server and a client (running SSH server and SSH client programs, respectively). The protocol specification distinguishes between two major versions that are referred to as SSH-1 and SSH-2. SSH uses public-key cryptography to authenticate the remote computer and allow it to authenticate the user, if necessary. Anyone can produce a matching pair of different keys (public and private). The public key is placed on all computers that must allow access to the owner of the matching private key (the owner keeps the private key secret). While authentication is based on the private key, the key itself is never transferred through the network during authentication. SSH only verifies whether the same person offering the public key also owns the matching private key. Hence, in all versions of SSH it is important to verify unknown public keys, i.e. associate the public keys with identities, before accepting them as valid. Accepting an attacker's public key without validation will authorize an unauthorized attacker as a valid user.

SSH also supports password-based authentication that is encrypted by automatically generated keys. In this case the attacker could imitate the legitimate side, ask for the password and obtain it (man-in-the-middle attack). However, this is only possible if the two sides have never authenticated before, as SSH remembers the key that the remote side once used. Password authentication can be disabled. SSH is important in cloud computing to solve connectivity problems, avoiding the security issues of exposing a cloud-based virtual machine directly on the Internet. An SSH tunnel can provide a secure path over the Internet, through a firewall to a virtual machine.

The following RFC publications by the IETF "secsh" working group document SSH-2 as a proposed Internet standard.

RFC 4250, The Secure Shell (SSH) Protocol Assigned Numbers; RFC 4251, The Secure Shell (SSH) Protocol Architecture; RFC 4252, The Secure Shell (SSH) Authentication Protocol; RFC 4253, The Secure Shell (SSH) Transport Layer Protocol; RFC 4254, The Secure Shell (SSH) Connection Protocol; RFC 4255, Using DNS to Securely Publish Secure Shell (SSH) Key Fingerprints; RFC 4256, Generic Message Exchange Authentication for the Secure Shell Protocol (SSH); RFC 4335, The Secure Shell (SSH) Session Channel Break Extension; RFC 4344, The Secure Shell (SSH) Transport Layer Encryption Modes; RFC 4345, Improved Arcfour Modes for the Secure Shell (SSH) Transport Layer Protocol; RFC 4419, Diffie-Hellman Group Exchange for the Secure Shell (SSH) Transport Layer Protocol (March 2006); RFC 4432, RSA Key Exchange for the Secure Shell (SSH) Transport Layer Protocol (March 2006); RFC 4462, Generic Security Service Application Program Interface (GSS-API) Authentication and Key Exchange for the Secure Shell (SSH) Protocol (May 2006); RFC 4716, The Secure Shell (SSH) Public Key File Format (November 2006); RFC 5656, Elliptic Curve Algorithm Integration in the Secure Shell Transport Layer (December 2009).

The SSH-2 protocol has an internal architecture (defined in RFC 4251) with well-separated layers. These are:

The transport layer (RFC 4253). This layer handles initial key exchange as well as server authentication, and sets up encryption, compression and integrity verification. It exposes to the upper layer an interface for sending and receiving plaintext packets with sizes of up to 32,768 bytes each (more can be allowed by the implementation). The transport layer also arranges for key re-exchange, usually after 1 GB of data has been transferred or after 1 hour has passed, whichever is sooner.

The user authentication layer (RFC 4252). This layer handles client authentication and provides a number of authentication methods. Authentication is client-driven: when one is prompted for a password, it may be the SSH client prompting, not the server. The server merely responds to the client's authentication requests. Widely used user authentication methods include the following:

password: a method for straightforward password authentication, including a facility allowing a password to be changed. This method is not implemented by all programs.

publickey: a method for public key-based authentication, usually supporting at least DSA or RSA keypairs, with other implementations also supporting X.509 certificates.

keyboard-interactive (RFC 4256): a versatile method where the server sends one or more prompts to enter information and the client displays them and sends back responses keyed-in by the user. Used to provide one-time password authentication such as S/Key or SecurID. Used by some OpenSSH configurations when PAM is the underlying host authentication provider to effectively provide password authentication, sometimes leading to inability to log in with a client that supports just the plain password authentication method.

GSSAPI authentication methods which provide an extensible scheme to perform SSH authentication using external mechanisms such as Kerberos 5 or NTLM, providing single sign on capability to SSH sessions. These methods are usually implemented by commercial SSH implementations for use in organizations, though OpenSSH does have a working GSSAPI implementation.

The connection layer (RFC 4254). This layer defines the concept of channels, channel requests and global requests using which SSH services are provided. A single SSH connection can host multiple channels simultaneously, each transferring data in both directions. Channel requests are used to relay out-of-band channel specific data, such as the changed size of a terminal window or the exit code of a server-side process. The SSH client requests a server-side port to be forwarded using a global request.

The SSHFP DNS record (RFC 4255) provides the public host key fingerprints in order to aid in verifying the authenticity of the host.

This open architecture provides considerable flexibility, allowing SSH to be used for a variety of purposes beyond a secure shell. The functionality of the transport layer alone is comparable to Transport Layer Security (TLS); the user authentication layer is highly extensible with custom authentication methods; and the connection layer provides the ability to multiplex many secondary sessions into a single SSH connection, a feature comparable to BEEP and not available in TLS.

These are intended for performance enhancements of SSH products:

SSH-over-SCTP: support for SCTP rather than TCP as the connection oriented transport layer protocol.

ECDSA: support for elliptic curve DSA rather than DSA or RSA for signing.

ECDH: support for elliptic curve Diffie-Hellman rather than plain Diffie-Hellman for encryption key exchange.

UMAC: support for UMAC rather than HMAC for MAC/integrity.

Figure 3:
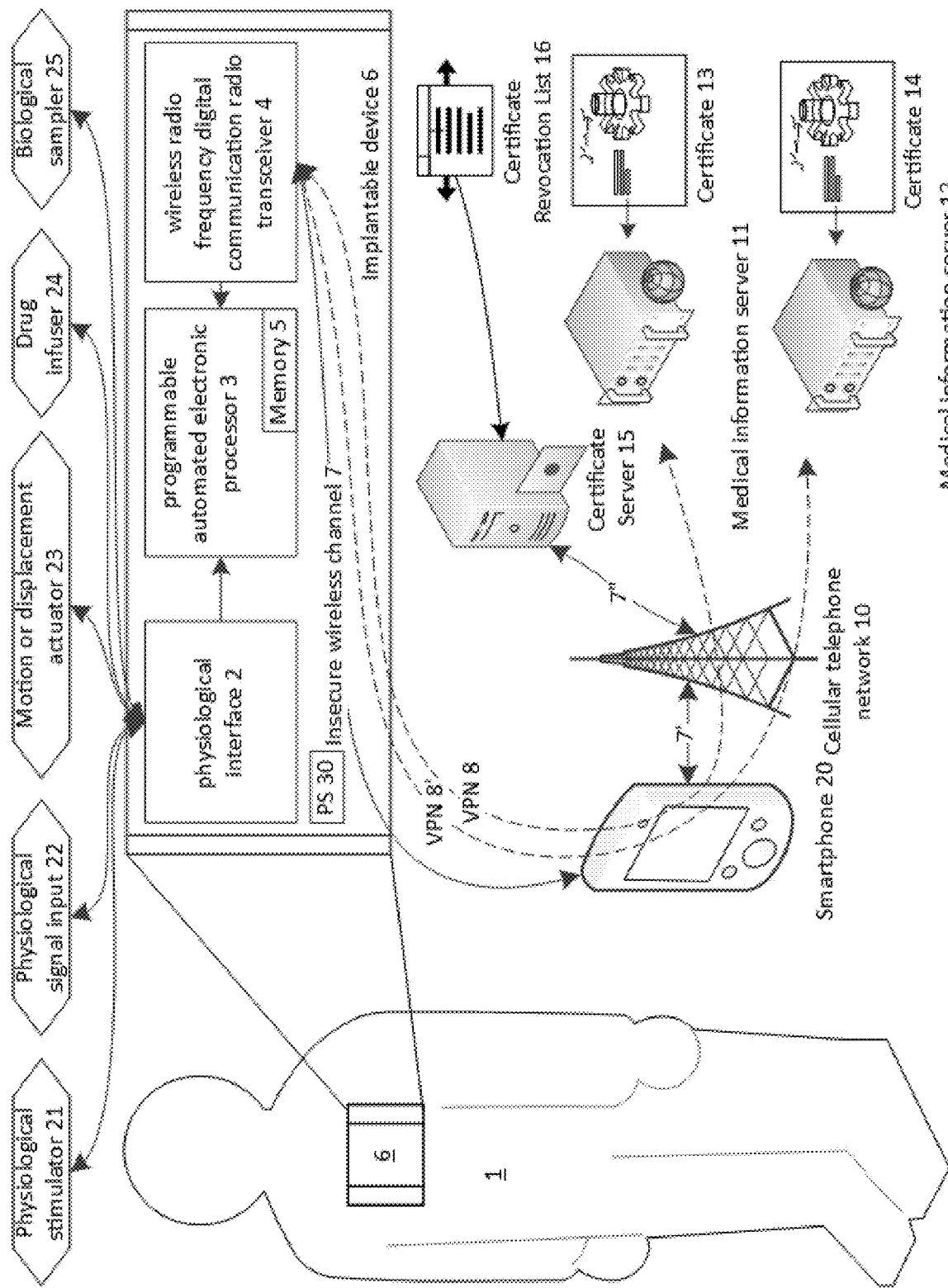
FIG. 3 shows a schematic diagram of a system according to the present invention.

FIG. 3 shows a schematic diagram of an implantable medical device 6 according to the present invention. An implantable medical device 6 is implanted into a patient 1, having a wireless radio frequency digital communication radio transceiver 4; a physiological interface 2 adapted to at least one of receive a physiological signal 22, produce a physiological stimulation 21, produce a motion or displacement 23, infuse a drug 24, and acquire a biological sample 25. The implantable medical device 6 is controlled by at least one programmable automated electronic processor 3, having a memory 5, configured to:

(a) communicate through the wireless radio frequency digital communication radio transceiver 4 over an insecure physical channel 7 with a relay device, which may be smartphone 20, and through the smartphone 20 to establish a cryptographically secure tunneling protocol communication with each of a plurality of different endpoints 11, 12 on a public network, e.g., medical information servers, the plurality of different endpoints each having a respective associated endpoint security certificate 13, 14, to implement a public key infrastructure, (b) respond to a request initiated from a respective one of the plurality of different endpoints 11, 12, to open a cryptographically secure tunneling protocol communication session 8, 9 according to the public key infrastructure with the respective one of the plurality of different endpoints 11, 12, the request being conveyed in at least one message received through the insecure physical channel 7 by the wireless radio frequency digital communication radio transceiver 4, and (c) verify the respective associated endpoint security certificate 13, 14 of the respective one of the plurality of different endpoints 11, 12, with respect to at least a certificate revocation list 16 (downloaded from a certificate server 15), prior to transmitting private medical data or accepting received medical data as valid. The smartphone communicates through a cellular network 10, which may interface to the Internet (not shown). The insecure physical channel 7 may comprise a radio frequency communication within at least one of an 870 MHz, 915 MHz, and 2.4 GHz communication band, and preferably the 2.4 MHz band. The smartphone 20 may be configured to execute a smartphone app to provide a local user interface with the at least one programmable automated electronic processor 3.

The at least one programmable automated electronic processor 3 may initiate a request to a respective one of the plurality of different endpoints 11, 12, to open a cryptographically secure tunneling protocol communication session 8, 8' according to the public key infrastructure, by sending a message over the insecure physical channel 7, which may be, e.g., a short range communication protocol such as Bluetooth®. The at least one programmable automated electronic processor 3 may encrypt information according to the Advanced Encryption Standard (AES). The at least one programmable automated electronic processor 3 may request the certificate revocation list 16 from a certificate server 15 at a certification authority through the insecure physical channel 7 with the relay device, and through the relay device (smartphone 20) to the certification server 15 through cellular communication channel 7' and communication network channel 7" according to a public key infrastructure hierarchy management system. The cryptographically secure tunneling protocol communication 8, 8' may be a virtual private network (VPN).

The implantable medical device may include a power supply 30 and a rewritable memory 5 storing computer readable instructions for controlling the at least one programmable automated electronic processor to implement the public key infrastructure stored in the rewritable memory, which are securely updatable through the insecure physical channel.

The at least one programmable automated electronic processor 3 may validate the smartphone 20 with respect to at least one of an execution checkpoint, a hash of memory contents, and an execution timing.

The figures and text herein describe methods and systems according to various aspects of the invention. It will be understood that each step described herein can be implemented by computer program instructions. These computer program instructions may be loaded onto a computer or other programmable apparatus to produce a machine, such that the instructions which execute on the computer or other programmable apparatus create means or devices for implementing the described functions or step(s). These computer program instructions may also be stored in a computer-readable memory that can direct a computer or other programmable apparatus to function in a particular manner, such that the instructions stored in the computer-readable memory produce an article of manufacture, including instruction means or devices which implement the specified functions or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the specified functions or step(s).

It will also be understood that each step or combinations of steps described herein can be implemented by special purpose hardware-based computer systems which perform the specified functions or steps, or combinations of special purpose hardware and computer instructions.

The foregoing has described systems and methods for monitoring a patient's heart. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation, the invention being defined by the claims.

What is claimed is:

1. A communication device, comprising:
a wireless network digital communication transceiver, configured to communicate with another wireless digital communication transceiver through a multi-hop mesh network comprising at least one untrusted intermediate node, according to a multi-hop mesh networking communication protocol;

an external interface, configured to at least one of receive information from a sensor, and to generate a control signal for an output device; and
at least one automated processor, configured to:
receive an identification of a remote server through the wireless network digital communication transceiver, the identification being automatically securely and reliably transmitted from an authenticated source through the at least one untrusted intermediate node;
updating the identification of the remote server, after receipt of the identification using secure and reliable communications through the at least one untrusted intermediate node;
check the remote server against a remotely-hosted certificate revocation list, using secure and reliable communications through the at least one untrusted intermediate node;
perform a secure and reliable key exchange with the remote server if a certificate of the remote server is not on the certificate revocation list, through the at least one untrusted intermediate node, secure from interception key information by the at least one untrusted intermediate node; and
establish an encrypted communication channel based on the secure and reliable key exchange with the remote server by communications through both the wireless network digital communication transceiver and the at least one untrusted intermediate node; and
communicate information between the encrypted communication channel and the external interface secure from interception and secure from undetected message modification by the at least one untrusted intermediate node.

2. The communication device according to claim 1, wherein the communicated information comprises control information for execution by the at least one automated processor.

3. The communication device according to claim 1, wherein the communicated information comprises sensor data from the external interface.

4. The communication device according to claim 1, wherein the encrypted communication channel comprises the Internet.

5. The communication device according to claim 1, wherein the wireless network digital communication transceiver comprises a wireless personal area network device.

6. The communication device according to claim 1, wherein the wireless network digital communication transceiver comprises a wireless local area network device.

7. The communication device according to claim 1, wherein the encrypted communication channel comprises a cellular communication channel.

8. The communication device according to claim 1, wherein the encrypted communication channel comprises a virtual private network.

9. The communication device according to claim 1, wherein the wireless network digital communication transceiver comprises an IEEE-802.15 transceiver and the at least one untrusted intermediate node comprises a smartphone executing an untrusted downloadable app, the untrusted downloadable app having access to communications packets of the multi-hop mesh networking communication protocol.

10. The communication device according to claim 1, wherein the at least one automated processor is configured to receive the identification of a remote server based on an initiating inbound received communication through the wireless network digital communication transceiver.

11. The communication device according to claim 1, wherein the at least one automated processor is configured to establish the encrypted communication channel based on an initiating inbound received communication through the wireless network digital communication transceiver.

12. The communication device according to claim 1, wherein the at least one automated processor is further configured to block execution of commands for control of the external interface received through the wireless network digital communication transceiver which are received outside of the encrypted communication channel.

13. A communication method, for controlling a communication device comprising:
a wireless network digital communication transceiver communicating with another wireless digital communication transceiver through a multi-hop mesh network comprising at least one untrusted intermediate node, according to a multi-hop mesh networking communication protocol;
an external interface for at least one of receiving information from a sensor, and generating a control signal for an output device; and
at least one automated processor,
the method comprising:
checking an identification of a remote endpoint for communications against a certificate revocation list;
performing a key exchange with the identified remote endpoint, if the identified remote endpoint is not the on the certificate revocation list, through the at least one untrusted intermediate node;
establishing an encrypted communication channel based on the key exchange with the remote endpoint by communications through the wireless network digital communication transceiver and the at least one untrusted intermediate node; and
communicating information between the encrypted communication channel and the external interface,
the receipt of identification, the check against the certificate revocation list, and the communicated information each using communications secure from undetected message modification by the at least one untrusted intermediate node, and
the key exchange, and the communicated information each being secure from interception of key information by the at least one untrusted intermediate node.

14. The method according to claim 13, further comprising:
receiving an identification of the remote endpoint through the wireless network digital communication transceiver; and
automatically securely transmitting the identification of the remote endpoint from an authenticated source through the at least one untrusted intermediate node.

15. The method according to claim 13, further comprising executing control information contained in the communicated information by the at least one automated processor.

16. The method according to claim 13, further comprising transmitting sensor data from the external interface in the communicated information.

17. The method according to claim 13, further comprising at least one of updating an identification of a remote endpoint and initiating the encrypted communication, based on an unsolicited inbound communication received through the wireless network digital communication transceiver.

18. The method according to claim 13, wherein:
the encrypted communication channel comprises the Internet;

the wireless network digital communication transceiver comprises at least one of a wireless personal area network device and a wireless local area network device;

the encrypted communication channel comprises a cellular communication channel;

the encrypted communication channel comprises a virtual private network;

the at least one untrusted intermediate node comprises a smartphone executing an untrusted downloadable app; and the untrusted downloadable app has access to communications packets of the multi-hop mesh networking communication protocol.

19. A non-transitory computer readable medium storing instructions for control of at least one automated processor of a communication device comprising a wireless network digital communication transceiver communicating with another wireless digital communication transceiver through a multi-hop mesh network comprising at least one untrusted intermediate node, according to a multi-hop mesh networking communication protocol, and an external interface at least one of receiving information from a sensor, and generating a control signal for an output device, the instructions comprising:

instructions for checking an identification of a remote endpoint for communications against a certificate revocation list;

instructions for performing a key exchange with the identified remote endpoint, if the identity of the remote endpoint is not on the certificate revocation list, through the at least one untrusted intermediate node;

instructions for establishing an encrypted communication channel based on the key exchange with the remote endpoint by communications through the wireless network digital communication transceiver and the at least one untrusted intermediate node; and instructions for communicating information between the encrypted communication channel and the external interface, wherein the instructions for the receipt of identification, the instructions for the check against the certificate revocation list, and the instructions for the communicating of information each define communications secure from undetected message modification by the at least one untrusted intermediate node, and wherein the instructions for performing the key exchange, and the instructions for communicating of information each define communications secure from interception of key information by the at least one untrusted intermediate node.

20. The non-transitory computer readable medium according to claim 19, further storing instructions for control of at least one automated processor for receiving an identification of the remote endpoint through the wireless network digital communication transceiver, the instructions for receiving the identification of the remote endpoint defining communications which automatically securely transmit from an authenticated source through the at least one untrusted intermediate node.

* * * * *